(12) United States Patent
Borden et al.

(10) Patent No.: US 7,136,163 B2
(45) Date of Patent: Nov. 14, 2006

(54) DIFFERENTIAL EVALUATION OF ADJACENT REGIONS FOR CHANGE IN REFLECTIVITY

(75) Inventors: Peter G. Borden, San Mateo, CA (US); Edward W. Budiarto, Milpitas, CA (US)

(73) Assignee: Applied Materials, Inc., Santa Clara, CA (US)

(*) Notice: Subject to any disclaimer, the term of this patent is extended or adjusted under 35 U.S.C. 154(b) by 435 days.

(21) Appl. No.: 10/732,436

(22) Filed: Dec. 9, 2003

(65) Prior Publication Data

US 2005/0122515 A1 Jun. 9, 2005

(51) Int. Cl.
*G01J 4/00* (2006.01)
(52) U.S. Cl. .................................... 356/369
(58) Field of Classification Search ............... 356/365, 356/366, 367, 368, 369
See application file for complete search history.

(56) References Cited

U.S. PATENT DOCUMENTS

| | | | |
|---|---|---|---|
| 4,758,092 A | 7/1988 | Heinrich et al. | 356/364 |
| 4,873,434 A | 10/1989 | See et al. | 250/235 |
| 5,530,550 A | 6/1996 | Nikoonahad et al. | 356/375 |
| 5,610,718 A * | 3/1997 | Sentoku et al. | 356/490 |
| 6,049,220 A | 4/2000 | Borden et al. | 324/765 |
| 6,072,179 A | 6/2000 | Paniccia et al. | 250/341 |
| 6,323,951 B1 | 11/2001 | Borden et al. | 356/502 |
| 6,411,389 B1 | 6/2002 | Rushford | 356/492 |
| 6,541,747 B1 | 4/2003 | Kikuchi et al. | 250/201 |
| 6,556,306 B1 | 4/2003 | Jiang et al. | 356/517 |
| 6,922,244 B1 | 7/2005 | Rosencwaig | 356/369 |

(Continued)

FOREIGN PATENT DOCUMENTS

EP 0 313 681 5/1989

(Continued)

OTHER PUBLICATIONS

H.K. Heinrich et al., "Picosecond Backside Optical Detection of Internal Signals in Flip-Chip Mounted Silicon VLSI Circuits", Microelectronic Engineering 16 (1992) Mar. pp. 313-324.

(Continued)

*Primary Examiner*—Layla G. Lauchman
*Assistant Examiner*—Michael A. Lyons
(74) *Attorney, Agent, or Firm*—Omkar K. Suryadevara

(57) ABSTRACT

A semiconductor wafer having two regions of different dopant concentration profiles is evaluated by performing two (or more) measurements in the two regions, and comparing measurements from the two regions to obtain a reflectivity change measure indicative of a difference in reflectivity between the two regions. Analyzing the reflectivity change measure yields one or more properties of one of the regions if corresponding properties of the other region are known. For example, if one of the two regions is doped and the other region is undoped (e.g. source/drain and channel regions of a transistor), then a change in reflectivity between the two regions can yield one or more of the following properties in the doped region: (1) doping concentration, (2) junction or profile depth, and (3) abruptness (i.e. slope) of a profile of dopant concentration at the junction. In some embodiments, the just-described measurements in the two regions are performed by use of only one beam of electromagnetic radiation. In several such embodiments, as reflectivity is a function of wavelength of an incident beam, three sets of measurements are made using laser beams of three different wavelengths, to obtain three reflectivity change measures (one at each wavelength). Next, the three reflectivity change measures are used to solve for each of three properties of the doped region, namely junction depth, doping concentration, and profile abruptness.

34 Claims, 40 Drawing Sheets

U.S. PATENT DOCUMENTS

| | | |
|---|---|---|
| 2002/0105636 A1 | 8/2002 | Okawauchi .................. 356/237 |
| 2002/0167326 A1 | 11/2002 | Borden et al. .............. 324/752 |

FOREIGN PATENT DOCUMENTS

| | | |
|---|---|---|
| EP | 0 566 217 A3 | 10/1993 |
| EP | 0718 595 A2 | 6/1996 |
| JP | 02102404 | 4/1990 |
| JP | 3158766 | 7/1991 |
| JP | 2000021748 | 1/2000 |

OTHER PUBLICATIONS

Chung Wah See and Mehdi Vaez-Iravani, "Differential amplitude scanning optical microscope: theory and applications", Applied Optics vol. 27, No. 13, Jul. 1, 1988, pp. 2786-2792.

ISR PCT/US04/040969, International filing date Aug. 12, 2004.

PCT/US04/040969 Written Opinion, International filing date Aug. 12, 2004.

ISR PCT/US04/041256, International filing date Aug. 12, 2004.

PCT/US04/041256 Written Opinion, International filing date Aug. 12, 2004.

Entire Prosecution History of U.S. Appl. No. 10/713,991.

* cited by examiner

```
Mathcad Professional - [Scanning xj solve.mcd]
File  Edit  View  Insert  Format  Math  Symbolics  Windows  Help
```

$Ns := 3 \cdot 10^{18}$     $k(\lambda) := 2 \cdot \frac{\pi}{\lambda}$     $\theta(\lambda) := 2 \cdot \pi \cdot \frac{c}{(\lambda \cdot 10^{-8})}$ $beta(\lambda) := \frac{(-q^2 \cdot 10^6)}{2 \cdot \left[ e0 \cdot \sqrt{e_s} \cdot m_e \cdot (\theta(\lambda))^2 \right]}$     $sinc(a,\lambda) := \frac{\sin(2 \cdot k(\lambda) \cdot n \cdot a)}{2 \cdot k(\lambda) \cdot n \cdot a}$     } 1001

$S(Nd,\lambda, z, a) := \left[ 4 \cdot beta(\lambda) \cdot \frac{(1-n)}{(1+n)^3} \right] \cdot (Nd - Ns) \cdot (1 - sinc(a,\lambda) \cdot \cos(2 \cdot k(\lambda) \cdot n \cdot z))$ $Nd := 10^{20}$
$z := 300$     } 1002
$a := 150$ Given $S(Nd, 9800, z, a) = 5.019 \cdot 10^{-3}$
$S(Nd, 8300, z, a) = 4.404 \cdot 10^{-3}$     } 1004
$S(Nd, 7300, z, a) = 3.836 \cdot 10^{-3}$

} 1003

$Find(Nd, z, a) = \begin{bmatrix} 8.028 \times 10^{19} \\ 3.99 \times 10^2 \\ 1.027 \times 10^2 \end{bmatrix}$     } 1005

Press F1 for help     AUTO    NUM    Page 6

*FIG. 10A*

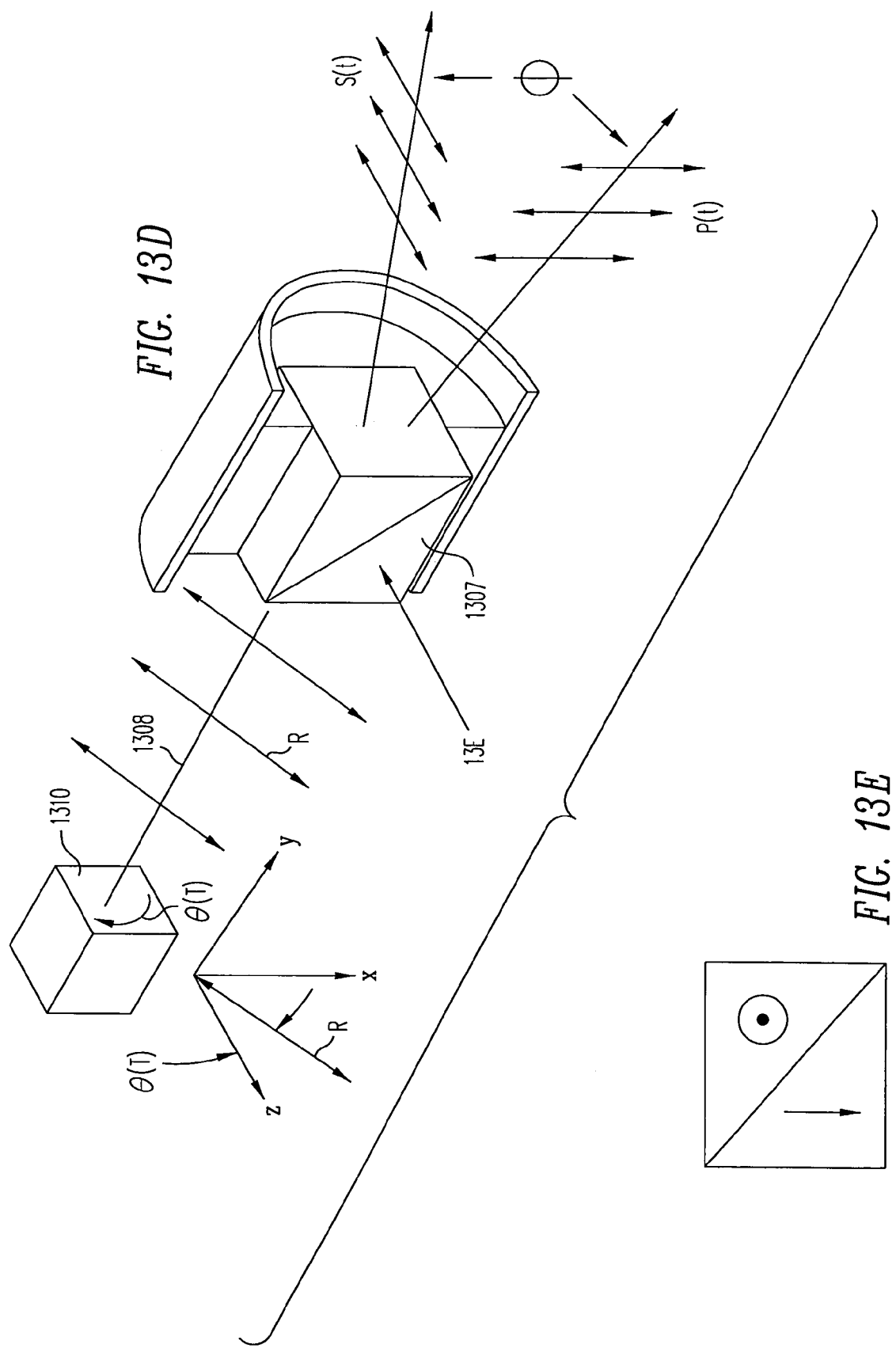

DIFFERENTIAL EVALUATION OF ADJACENT REGIONS FOR CHANGE IN REFLECTIVITY

CROSS-REFERENCE TO RELATED APPLICATION

This application is related to and incorporates by reference herein in its entirety a patent application entitled "USE OF SCANNING BEAM FOR DIFFERENTIAL EVALUATION OF ADJACENT REGIONS FOR CHANGE IN REFLECTIVITY", by the same inventors, U.S. application Ser. No. 10/731,991 filed concurrently on Dec. 9, 2003.

BACKGROUND

FIG. 1A shows a cross-sectional view of a MOS field effect transistor (FET) well known in the prior art. Such an MOS transistor typically includes source region 101s and drain region 101d, source extension region 102s and drain extension region 102d, channel 103, gate insulator 104, gate 105, and well 106, all of which are formed in semiconductor substrate 107. Additional doped layers may be present, but are not shown for simplicity. The source and drain regions 101s and 101d are heavily doped, typically with arsenic for n-type doping or boron for p-type doping. Doping levels are on the order of $10^{20}$ dopant atoms per cubic centimeter. The layers for regions 101s and 101d are typically 500–700 angstroms deep. The extension regions 102s and 102d are also heavily doped, with the same type of dopant atoms as the source and drain regions 101s and 101d, but the extension regions are shallower—typically 300 to 500 angstroms deep. FIG. 1B shows the doping profiles in the vertical directions (along the arrow A in FIG. 1A).

Extension regions 102s and 102d provide contacts to the channel region 103. The transistor operates by applying a bias to the gate 105 while grounding the well 106. For example, suppose the regions 101s, 102s, 102d and 101d are n-type, so that the majority carriers are electrons. If a positive voltage is placed on gate 105 with respect to the channel 103, no current will flow between the gate 105 and channel 103 because of the presence of thin gate insulator 104.

However, the positive voltage will attract electrons to the channel region 103, creating a thin layer of electrons (called an inversion layer) that connects source extension 102s to drain extension 102d, allowing current to flow between the source and drain. When the voltage on gate 105 is removed, the inversion layer in channel 103 ceases to exist, and the source is disconnected from the drain. In this manner, the transistor can be turned on and off.

In practice, the doping profiles for the various source and drain layers 101s, 101d, 102s and 102d are not perfectly abrupt (box-like). They are usually formed by diffusion processes that may involve several thermal cycles, causing the profiles to be somewhat rounded. For example, FIG. 1B shows two profiles 112A and 112B for the source extension 112s, following the arrow A in FIG. 1A. Line 112A shows a relatively abrupt profile and line 112B shows a less abrupt profile. Such variation in abruptness (between lines 112A and 112B) may be encountered in different semiconductor wafers under fabrication because each step in the fabrication process has a certain tolerance. Variation in individual process steps or the cumulative variation of a series of process steps can cause a loss of abruptness in the profile (e.g. may go from line 112A to line 112B). In addition, junction depth and peak doping concentration may vary depending on process properties, such as, for example, variation in annealing temperature. For example, profile 112B forms a deeper diffused profile than profile 112A, but at a smaller peak doping concentration.

The performance of the transistor is affected by the final doping profile after annealing. Profile depth, peak concentration, and profile abruptness are carefully controlled because they directly contribute to short-channel effects and speed of the transistor. A deeper and less abrupt profile in the vertical direction creates a higher off-state leakage current that leads to increased power consumption. A smaller peak doping concentration increases the resistance component between the source/drain region and the transistor channel, leading to a greater voltage drop between the source 101s and drain 101d (FIG. 1A). This voltage drop reduces the ability of the transistor to drive the next stage, reducing the speed of the circuit.

A wide variety of methods are available in the prior art to characterize doped layers in semiconductors. However, such methods are unable (to the Applicants' knowledge) to provide this characterization in a small measurement size of less than 10 μm in diameter, and to do so without damage or contact to the layer being measured. These limitations require measurement on product wafers (as opposed to test or reference wafers) with doped areas formed in fine patterns, and effectively eliminate destructive methods such as Secondary Ion Mass Spectrometer (SIMS) and Scanning Capacitance Microscopy (SCM) from considerations.

Inference of doped layer properties is possible using electrical probing of transistors. However, this procedure requires physical contact of probes to a completed transistor structure. Moreover, this procedure is impractical in the middle of a process wherein the doped layers are being formed and the transistor is still incomplete. The time between performance of source/drain process steps and the first opportunity to electrically probe the completed structure can be days or weeks, greatly reducing the ability to implement real-time process control using electrical probing.

Borden et. al. have described methods for measurement of junction depth in U.S. Pat. Nos. 6,323,951 and 6,049,220. Moreover, U.S. Pat. Nos. 5,966,019 and 5,883,518 by Borden describe splitting of a laser beam into two parts of orthogonal polarization, and interference of reflection of the two orthogonal polarization components to form a signal indicative of semiconductor material properties. The just-described four patents are all incorporated by reference herein in their entirety as background.

Jiang et al. describe (in U.S. Pat. No. 6,556,306 which is incorporated by reference herein in its entirety as background) a method for determining the index of refraction of a thin film at a desired angular frequency. Jiang et al. disclose (in the abstract) generating an input desired-frequency pulse and an output detectable probe pulse. According to Jiang et al. a thin film is moved in and out of the path of the input pulse, creating an output pulse that alternates between a transmitted signal created when the film intercepts the input pulse path, and a reference signal, created when the sample is outside the input pulse path. The output pulse modulates the probe pulse, which is then detected with a photodetector and the difference between the transmitted signal and the reference signal is calculated. The above steps are repeated over a plurality of delay times between the input pulse and the probe pulse until a complete field waveform of the differential signal is characterized. The index of refraction is calculated by Jiang et al. as a function of a ratio between the differential signal for the thin film and the reference signal.

Heinrich et al. describe (in U.S. Pat. No. 4,758,092 which is incorporated by reference herein in its entirety as background) a method and means for optical detection of charge density modulation in a semiconductor. Heinrich et al. describe passing a polarized coherent light beam onto an interferometer which establishes two polarized beams. The two polarized beams are focused on a silicon device under test with one beam focused on or near an active device and one beam providing a reference. After passing through the device under test the two beams are reflected off a metal layer and back through the device under test where they are recombined by the beam splitter. However, the charge carriers affect the index of refraction of silicon, and by modulating the electrical charge in the active device a small modulation occurs in the index of refraction. The modulation affects the phase delay of the one beam near the active device in relation to the reference beam, and hence when the beams are recombined at the beam splitter they interfere and convert the relative phase modulation into an amplitude modulation which can be detected with a photodiode.

Heinrich et al. also state that the position of a single optical beam can be spatially modulated over a silicon wafer surface to detect stationary charge densities in one area relative to a reference area. The reference area may contain no charge density variation thereby giving an absolute reference value.

SUMMARY FOR SEVERAL EMBODIMENTS OF THE INVENTION

A semiconductor wafer having at least two regions of different reflectivities on a front surface thereof is evaluated in accordance with the invention by generating a beam of substantially monochromatic electromagnetic radiation of a predetermined wavelength $\lambda$, illuminating each of the two regions on the front surface with the beam either simultaneously or sequentially, while continuously measuring intensity of a portion of the beam reflected by the illuminated region during uninterrupted rhythmic movement, by use of a photodetector sensitive to the wavelength $\lambda$. In some embodiments (also called "beam splitting embodiments"), the two regions are illuminated simultaneously by splitting the beam (which is linearly polarized) into two beams of S and P polarization each of which illuminates one of the regions. In alternative embodiments (also called "beam scanning" embodiments), the beam is scanned between the two regions, to alternately illuminate each region.

In the beam scanning embodiments, the signal sensed by the photodetector varies synchronously at the predetermined frequency f at which the beam is being oscillated between the two regions. In the beam splitting embodiments, the intensity of the S and P polarized beams is modulated over time at a predetermined frequency f, such that the two regions are alternately illuminated. In the beam splitting embodiments, the signal detected by the photodetector also varies synchronously at the predetermined frequency f and in a phase-sensitive manner. In beam splitting embodiments as well as in beam scanning embodiments, the amplitude of fluctuation (i.e. the time varying component) of an analog electrical signal being sensed by the photodetector is thereafter used as a measure of change in reflectivity between the two regions, e.g. in process control. In some embodiments the measurement is performed on a test structure that is fabricated at the same time as (and using the same processes as) active devices in the wafer.

Although in a number of beam splitting embodiments of the type described above, a single beam is being split, in other embodiments two beams that are coaxial are split, and the S and P polarization components of each beam are incident on a test structure and form concentric spots thereon. While both beams are incident on and reflected by each region in the test structure, one of the beams is not modulated and reflection of this beam is filtered out by an optical element present in the path of the reflected beams, and the other beam is incident on and detected by the photodetector in the above-described manner. In certain applications involving pre-anneal low-dose implants, the use of two beams enhances the reflectivity of, for example, a doped region due to creation of carriers by the additional beam. Therefore, the difference in reflectivity measured by (i.e. the amplitude of fluctuation of the electrical signal generated by) the photodetector is larger, and any deviation therein is easier to detect. In other applications involving post-annealed samples, the use of two beams also enhances the sensitivity of the measurement to other properties of the doped layer such as oxide charge and defect densities, due to creation of excess carriers by the additional beam.

In yet another beam splitting embodiment, two beams are used in the above-described manner, except that only one beam is split and this beam is unmodulated, whereas the other beam is not spit and has an oscillating intensity.

BRIEF DESCRIPTION OF THE DRAWINGS

FIG. 10A illustrates a screenshot of a commercially-available software program Mathcad 2001i Professional which is programmed in accordance with certain embodiments of the invention to solve three simultaneous nonlinear equations for the determination of the following three properties: peak ($N_d$) of the dopant profile, depth ($z_j$) of the dopant profile, and abruptness (a) of the dopant profile using three amplitude measurements at three wavelengths.

FIG. 13D illustrates, in a close up perspective view, the use of Wollaston prism in some embodiments to generate two beams of mutually perpendicular polarizations from a single beam of rotating linear polarization that in turn is generated by a half-wave plate from a beam of linear polarization incident thereon.

FIG. 13E illustrates, in a side view in the direction 13E in FIG. 13D, the optic axes of two wedges of the Wollaston prism of FIG. 13D.

FIG. 13O illustrates a hardware configuration for an embodiment of the type illustrated in FIG. 13A using a rotating half-wave plate (1204) and a Wollaston prism (1214) to illuminate the doped and undoped regions (without movement along a line of the type illustrated in FIG. 3A).

DETAILED DESCRIPTION OF SEVERAL EMBODIMENTS OF THE INVENTION

Figure 1A:
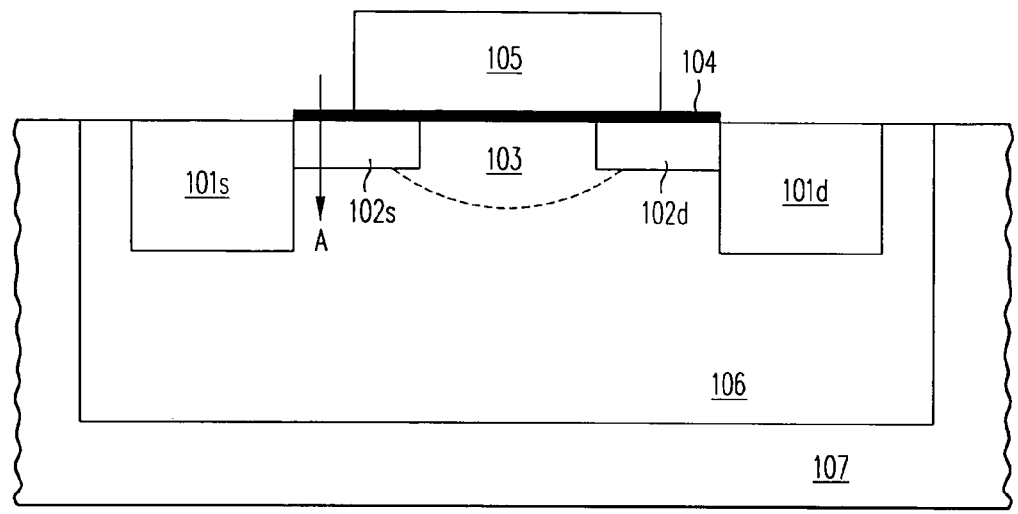
FIG. 1A shows, in a cross-sectional diagram through a prior art semiconductor wafer, the structure of a MOS field effect transistor.
Figure 1B:
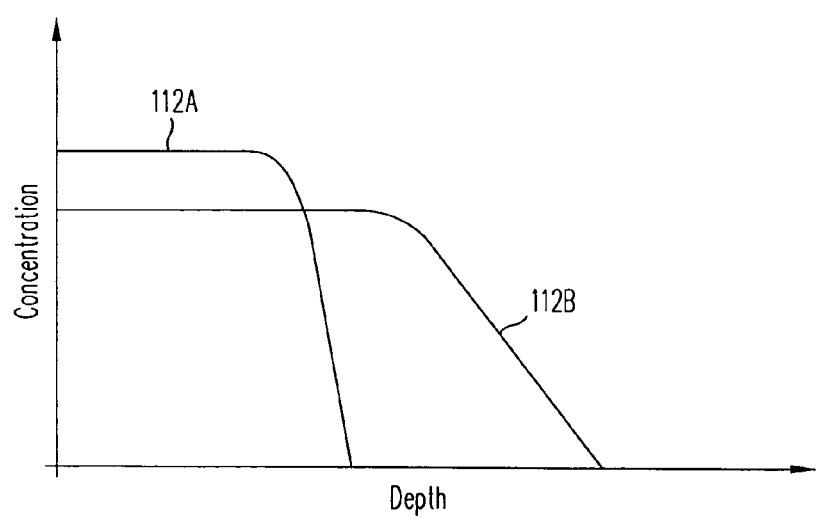
FIG. 1B shows, in graphs, the doping profile of the prior art semiconductor wafer, along arrow A of FIG. 1A through extension layer 102s.

During fabrication of a semiconductor wafer in accordance with the invention, a test structure 210 (FIG. 2B) is also simultaneously fabricated (as per act 201 in FIG. 2A), using the same processes that are used to form integrated circuits (e.g. IC portion 220) in the wafer. The only difference between regions of the test structure 210 and regions of the integrated circuit portion 220 is in dimensions. Specifically, the test structure 210 is designed to have dimensions sufficiently large to accommodate the presence of a beam 219 of electromagnetic radiation as described next. For example, a doped region 211 in the test structure may be a square with a side of the same size as the spot diameter. Making the doped region 211 of the test structure larger than the spot diameter accommodates error in alignment of the beam relative to the region.

Note that a doped region 211 in such a test structure may made smaller than the beam spot in some embodiments (e.g. the doped region's diagonal may be same as the spot diameter), although the signal measured in such embodiments is not as sensitive to a change in properties between regions. Note also that the specific active device 220 that is being fabricated in the wafer is not a critical aspect of the invention, as long as a structure 210 to be tested is formed at the same time as and in the same manner as the active device 220 (or portions thereof).

Figure 2A:
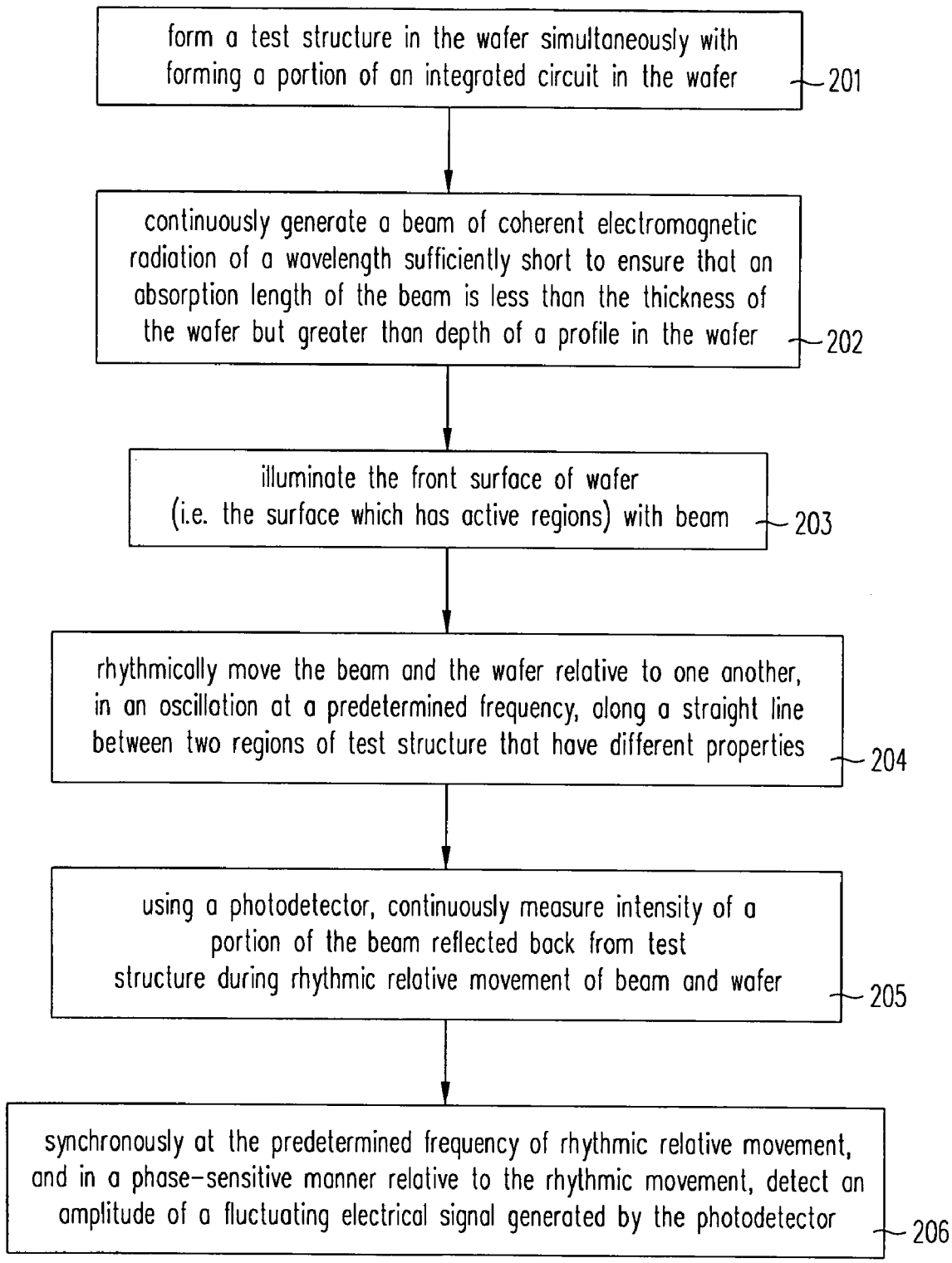
FIG. 2A illustrates, in a flow chart, acts performed in several embodiments of the invention.
Figure 2B:
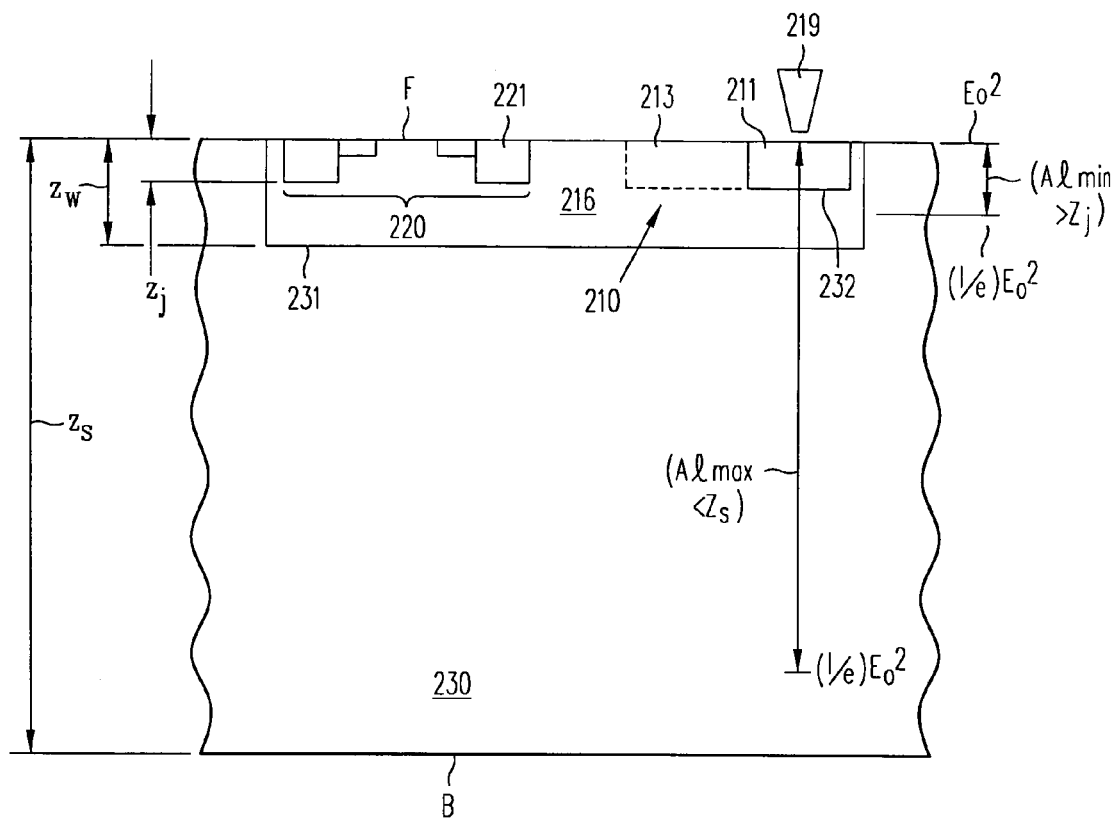
FIG. 2B illustrates, in a cross-sectional view, the relative dimensions of absorption length Al, wafer thickness $z_s$, well depth $z_w$ and depth $z_j$ of an interface between doped region 211 and well region 216.

In accordance with the invention, the above-described wafer is evaluated during semiconductor wafer fabrication by use of a laser (or other such coherent light source) to generate a beam 219 (FIG. 2B) of substantially (or even precisely) monochromatic electromagnetic radiation of a predetermined wavelength λ (as per act 202 in FIG. 2A) and illuminating a front surface F of the wafer using the continuously generated beam (as per act 203 in FIG. 2A). For the oscillating beam embodiments, beam 219 could be polarized or unpolarized depending on the embodiment.

Illumination of the front surface F in all embodiments described herein allows the incident electromagnetic radiation to immediately reach (and be reflected from) regions of interest, such as doped regions, undoped regions, metallic regions or other such regions that are being fabricated at the front surface F of the wafer, without having to pass through most of the wafer's thickness. This is in contrast to prior art illumination of the wafer's bottom surface as disclosed by Heinrich et al. in U.S. Pat. No. 4,758,092. Illumination of the bottom surface as suggested by Heinrich et al. requires the incident beam to travel all the way through the thickness of a wafer to reach a metal layer (at the front surface) which reflects the energy incident thereon, and the reflected energy travels back all the way through the wafer thickness a second time. The need to travel throughout the thickness of the wafer has two disadvantages (a) any defect in the substrate affects the measurement (especially since substrates are manufactured with a larger tolerance for defects), and (b) to ensure that the reflected energy can be meaningfully measured it is necessary that a probe beam of a large wavelength (e.g. 1.3 μm) be used, as mentioned by Heinrich et al. at column 3, lines 61–62).

The predetermined wavelength λ of beam 219 (FIG. 2B) in accordance with the invention is selected to be sufficiently short to ensure that an absorption length Al of the beam in the wafer is less than the thickness $z_s$ of the wafer. The term "absorption length" is used to indicate a length (also called "penetration depth") at which the original intensity $E_o^2$ of beam 219 falls to $(1/e)E_o^2$. Therefore, more than a majority (about 63%) of the energy $E_o^2$ incident on a front surface F of the wafer does not even reach the bottom surface B of the wafer, when absorption length is less than wafer thickness. The same is true in the reverse direction, i.e. more than a majority (about 63%) of all energy in fact reflected by bottom surface B of the wafer does not even emerge outside the front surface F of the wafer. Furthermore, the energy reflected by the bottom surface B is not equal to the energy incident thereon, because of reduction due to reflectivity of the bottom surface B.

In some embodiments with absorption length less than wafer thickness (e.g. if absorption length is 690 μm and wafer thickness is 700 μm), then approximately 26% of the total energy incident on front surface F is transmitted to and becomes incident on bottom surface B, and therefore approximately 7.8% (of the total incident energy on front surface F) is reflected by bottom surface B, and therefore about 2.8% (of the total incident energy on front surface F) reaches front surface F and only about 2% (of the total incident energy on front surface F) emerges outside of the front surface F.

Use of beam 219 having absorption length Al less than wafer thickness $z_s$ in many embodiments of the invention ensures that most of the energy reflected by the wafer, other than from the front surface F, is reflected by regions and interfaces that are physically located between the front and bottom surfaces, e.g. regions 211 and 216 (FIG. 2B) that are formed in substrate 230 during semiconductor wafer fabrication. Therefore, use of such a short wavelength beam ensures that any portion of the incident beam 219 that may be reflected by the bottom surface B is limited to a negligible percentage (e.g. less than 10%) of the total energy reflected from the wafer. For example, if the total reflected energy is 30% of the incident energy, the bottom surface contribution is limited to less than 3%. Minimizing the contribution of bottom surface B by an order of magnitude, based on appropriately selecting the wavelength (and hence the absorption length) minimizes the contribution from one or more defects typically present in the substrate, if they happen to be in a path to and from bottom surface B.

Reducing the absorption length (and hence the wavelength) provides only diminishing returns (i.e. marginal benefits) beyond a certain point which depends on a number of factors that may be different in each embodiment, such as the signal to noise ratio (SNR) and cost (e.g. of the laser). Therefore, in some embodiments, the absorption length Al is selected to be no smaller than depth $z_j$ of a junction (or other profile) of a region formed during semiconductor wafer fabrication. Hence, any value for the absorption length in the range (junction depth<absorption length<wafer thickness) may be selected. Therefore, the maximum absorption length is $Almax<z_s$ and the minimum absorption length is $Almin>z_j$.

In one embodiment, junction depth $z_j$ is in a range of 500–800 angstroms and wafer thickness is 700 μm. In this embodiment, beam 219 having a wavelength λ of 1.04 μm can be selected for probing as described herein, because such a beam has an absorption length Al=700 μm. As noted above, when using such a beam, the contribution of the bottom surface to the energy being reflected from the wafer is a negligible percentage (about 2.4%) of the total energy incident on the front surface. To eliminate any contribution from the bottom surface and any intervening defect, beam 219 may be selected to be of an absorption length Al which is less than or equal to one-half the wafer thickness, i.e. less than or equal to 350 μm. In such a case, the energy being reflected by the wafer is primarily reflected from the front surface F and from regions of interest in the vicinity of front surface F.

For example, if beam 219 having a wavelength λ of 980 nm is selected for probing as described herein, its absorption length Al=100 μm is significantly less than 350 μm which is the one-half wafer thickness. In this example, only about 4.8% of the incident energy reaches half way into the substrate 230, and only 0.2% reaches the bottom surface. The incident energy of this wavelength is therefore practically extinguished in just reaching the bottom surface, with no likelihood of any portion of the 0.2% being able to return back to the front surface and emerging therefrom. Hence, the only energy emerging from the front surface is energy that is reflected by the front surface itself and energy that is reflected from the interfaces and regions that occur close to the front surface F, such as the interface 231 between well 216 and substrate 230, and interface 232 between region 211 and well 216, as well as regions therebetween such as well 216 and region 211.

In numerous embodiments of the type described herein, beam 219 is selected to have a wavelength λ of anywhere in the range 400 nm to 1.04 μm, wherein the lower limit is set by the absorption length being greater than junction depth (or profile depth) permitted by current technologies for Ultra Shallow (US) junctions, and the upper limit is set by the absorption length being less than the wafer thickness. Note that a beam of wavelength λ of 1.1 μm or greater cannot be used as described herein because its absorption length of 1500 μm is more than twice the wafer thickness of 700 μm (noted above). Note that beam 219 can have any power depending on the embodiment, e.g. between 5 mW and 100 mW. Note that beam 219 can be generated by a conventional laser diode, such as a Fiber Bragg Grating (FBG) stabilized AlGaAs laser with a wavelength of 980 nm and a power of 100 mW (part # 26-8052-100) available from JDS Uniphase, San Jose, Calif.

Figure 2C:
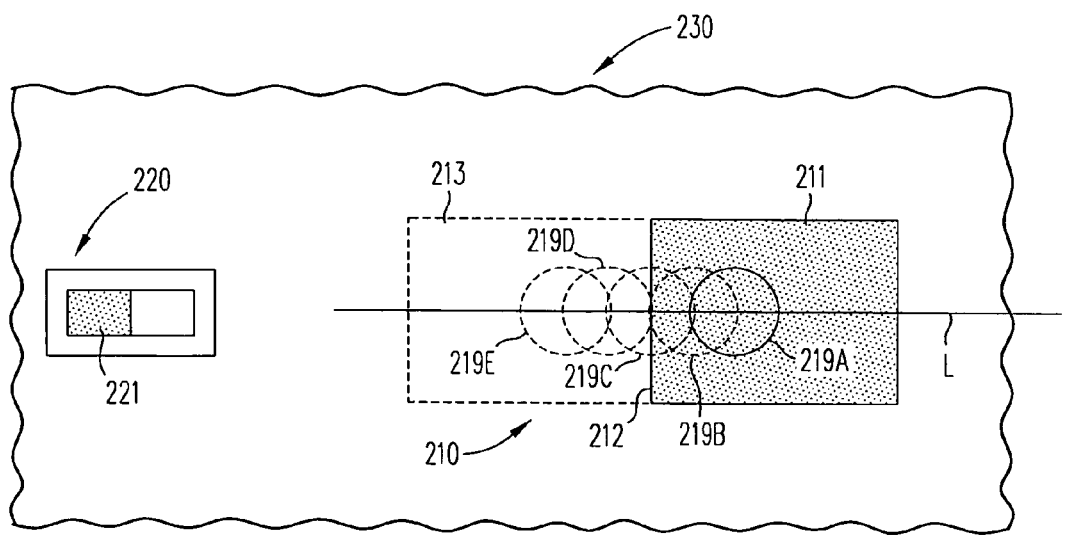
FIG. 2C illustrates, in a plan view, multiple positions of the incident beam (one position shown solid and four other positions shown dotted) during oscillating movement along a straight line L between the doped region 211 and the undoped region 213 of a test structure 210; also shown in FIG. 2C is an integrated circuit 220 formed simultaneous with test structure 210.
Figure 2D:
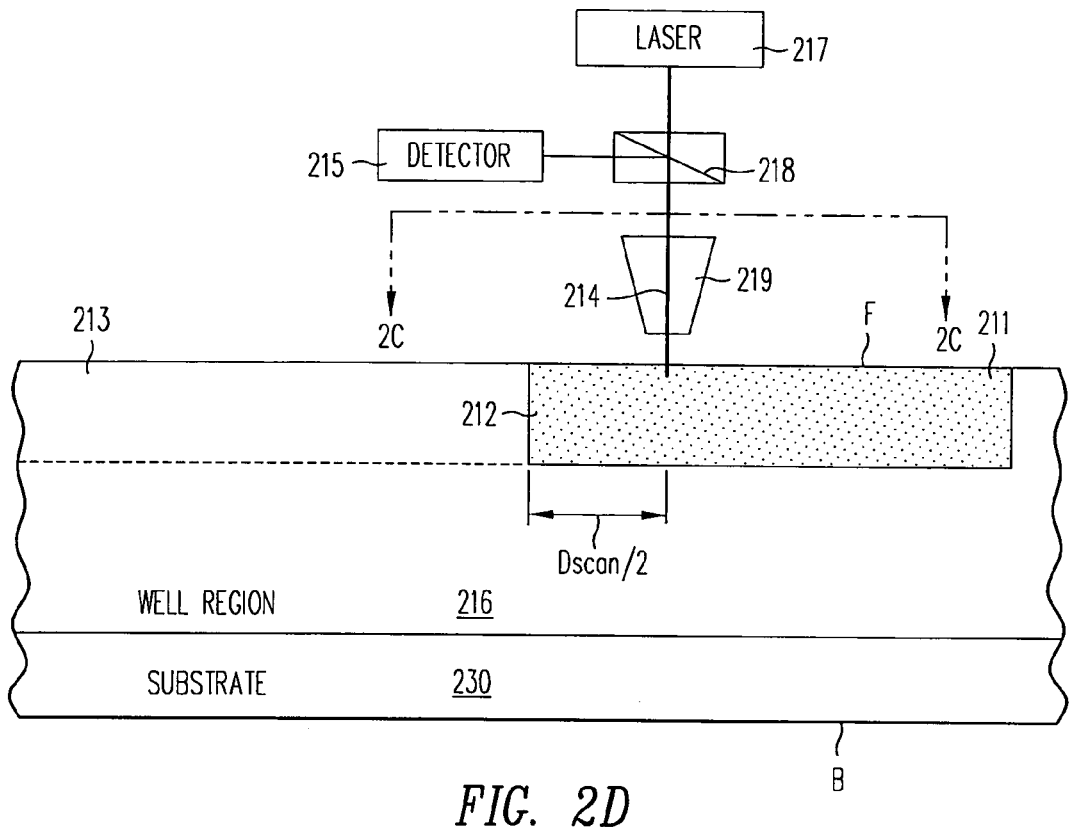
FIGS. 2D–2H illustrate, in a cross-sectional side view along line L of FIG. 2C, multiple positions of the incident beam of FIG. 2C.
Figure 2E:
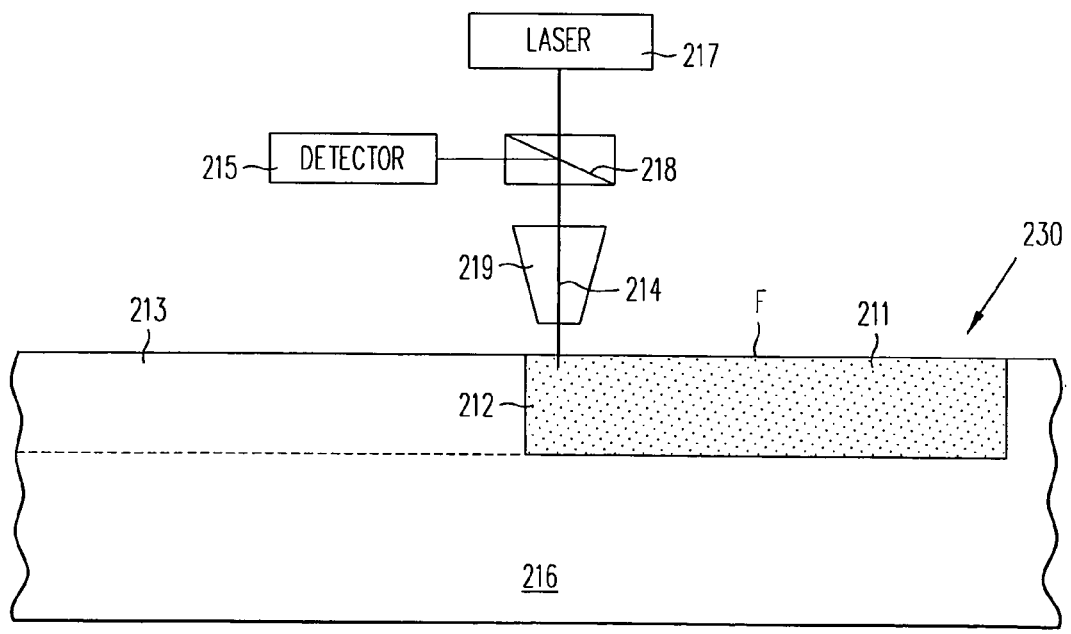
Figure 2F:
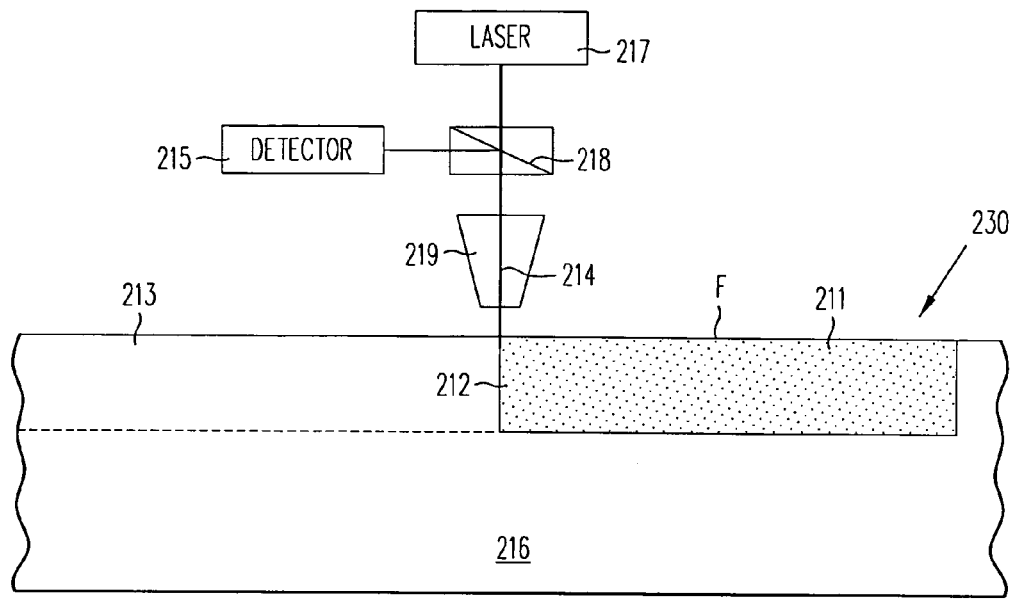
Figure 2G:
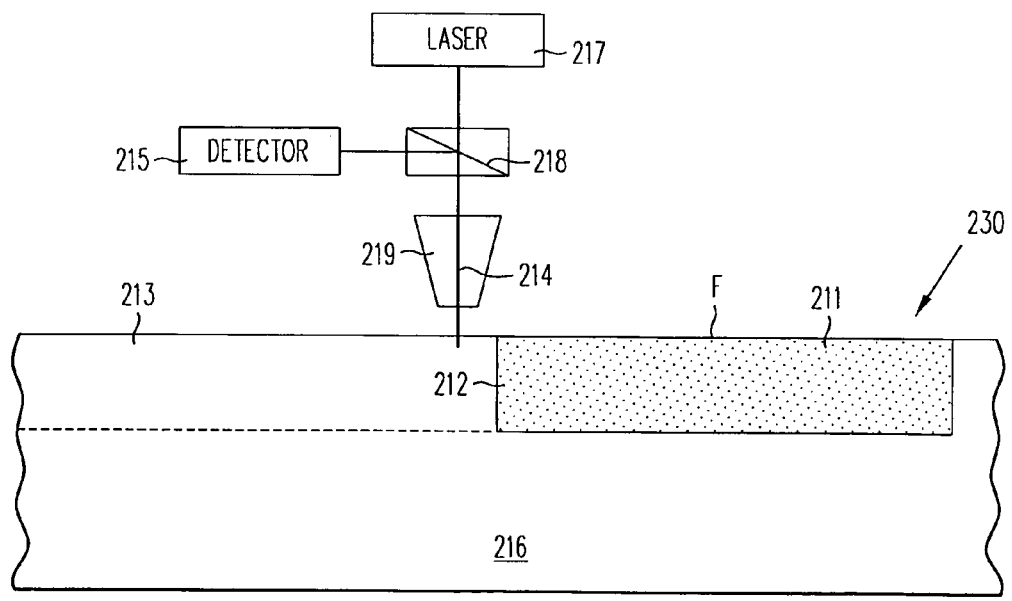

Beam 219 (FIG. 2B) of the type described above forms a spot on a front surface F of a wafer being evaluated, and such a spot (shown at position 219A in FIG. 2C) is moved relative to the wafer (see act 204), in a physical oscillation at a predetermined frequency f between two regions of a test structure, e.g. doped region 211 and undoped region 213 (FIG. 2C). In the just-described example, region 213 is formed of the same material as and is coextensive with a well region 216, and for this reason, region 213 is shown by a dashed line in FIGS. 2B and 2C. Beam 219 may be initially located at position 219A over a doped region 211 (FIG. 2C) and during act 204 the beam is moved continuously from position 219A to a symmetric position 219E over undoped region 213, transitioning through positions 219B, 219C and 219D therebetween along a straight line L. As shown in FIG. 2C, regions 211 and 213 are adjacent to one another and share a common boundary 212.

Note that only three intermediate positions are illustrated in FIG. 2C for clarity, although an innumerable number of such positions are present between positions 219A and 219E due to the continuous movement. Positions 219A and 219E are extreme end positions at which movement of the beam 219 is reversed. Therefore, after position 219E is reached, movement is reversed and the beam returns back to position 219A after transitioning through positions 219D, 219C and 219B. Side views of the five positions 219A–219E (FIG. 2C) are illustrated in the respective FIGS. 2D–2H.

Although certain embodiments require relative motion between a beam and the wafer, in alternative embodiments of the type described in reference to FIGS. 13–17, there is no relative motion. Instead, the intensity of a beam to be incident on a region of the wafer is modulated, e.g. by use of a rotating half-wave plate and a Wollaston prism in a path of the beam towards the wafer, or by modulating a laser driver that drives a laser that in turn generates the beam. Therefore, in some embodiments that modulate the beam's intensity, there is no relative motion between the beam and the wafer.

Referring back to FIGS. 2D–2H, during relative motion between the two regions 211 and 213, intensity of a portion of the beam reflected by the illuminated region is continuously measured (as per act 203) by a photodetector sensitive to the wavelength λ of the incident beam. Note that the intensity of the radiation being reflected changes during the relative motion, because the difference in reflectivity at the two end positions is the same as the difference in reflectivity between the two regions. At a central position between the two end positions, the beam is exactly 50% in each of the two regions and the reflectivity should be an average of the two reflectivities. In practice, reflectivity at the central location may significantly deviate from the average due to presence of discontinuities that may be inherent in the boundary between the two regions. At any other intermediate position, the reflectivity is a weighted average of the area of the two regions illuminated by the incident beam.

Therefore, during relative movement between the wafer and the beam (between the two end positions 219A and 219E in FIG. 2B), a photodetector 215 that is sensitive to the portion of the beam reflected from the wafer generates a continuous analog electrical signal. The generated electrical signal has a magnitude that varies with time, at the predetermined frequency f of relative movement between the beam and the wafer. As per act 205 in FIG. 2A, an amplitude of fluctuation (i.e. the time varying component) of the electrical signal is synchronously detected at frequency f of the relative movement, e.g. by use of a lock-in amplifier.

Note that in all embodiments of the invention, a beam that is incident on the wafer is generated continuously, and the beam is used to continuously illuminate the test structure. The continuous illumination of the test structure distinguishes this invention from the disclosure of Jiang et al. (in U.S. Pat. No. 6,556,306) which appears to require the use of pulses. Applicants note that Jiang appears to use the term "desired frequency" to mean a specific range of frequencies, e.g. GHz–THz (column 1 lines 8–27 and column 3, line 66), instead of a monochromatic beam. Applicants further note that Jiang uses a pulse, and a pulse normally has a frequency spread that is a significant multiple (e.g. 3 terahertz) of the center frequency (e.g. 1 terahertz). For either or both reasons, Jiang's pulse is not monochromatic (in the same sense that this term is used herein to describe a laser-generated beam which is used in some embodiments of Applicants' invention).

The amplitude of fluctuation (i.e. the time varying component) of the electrical signal generated by the photodetector is also referred to herein as a reflectivity change measure. The reflectivity change measure indicates a difference in reflectance between the two regions, and is thereafter used (1) to obtain a measure of a change in one or more properties between the two regions (based on modeling or previously collected data); or (2) to perform process control (by comparison with predetermined limits and changing a process parameter if outside a range).

In some embodiments, the just-described measurements (at the innumerable positions between and including end positions 219A and 219E) are performed by use of at least one beam of electromagnetic radiation that is incident normal to a surface F of the wafer (FIG. 2D), and a reflected portion of this beam is detected. FIGS. 2D–2H depict a beam splitter 218 that is shown to be in-line with the incident beam 219, to indicate that specular reflection from surface F in a direction opposite to the direction of incidence is being measured (wherein both directions are along a line 214 normal to the surface F). Beam splitter 218 passes a laser beam that is generated by laser 217 through to wafer 230. Beam splitter 218 splits off a portion (e.g. 50%) of the beam reflected by wafer 230 to a detector 215. For this reason, beam splitter 218 is also referred to elsewhere herein as "detection system beam splitter". Detection system beam splitter 218 is non-polarizing in many embodiments of the type described herein. Detector 215 is offset from the line of incidence and reflection 214 in the usual manner.

Figure 2H:
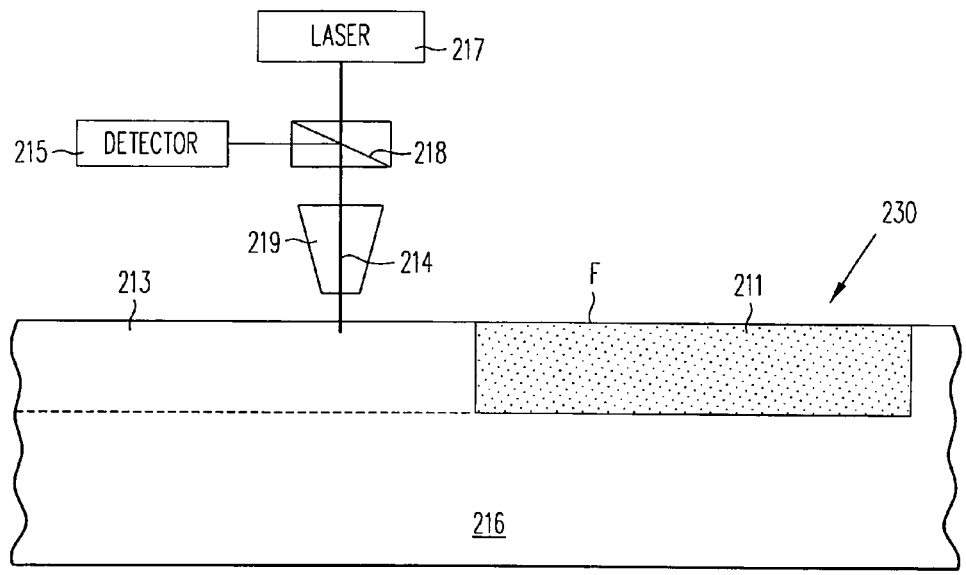
Figure 2I:
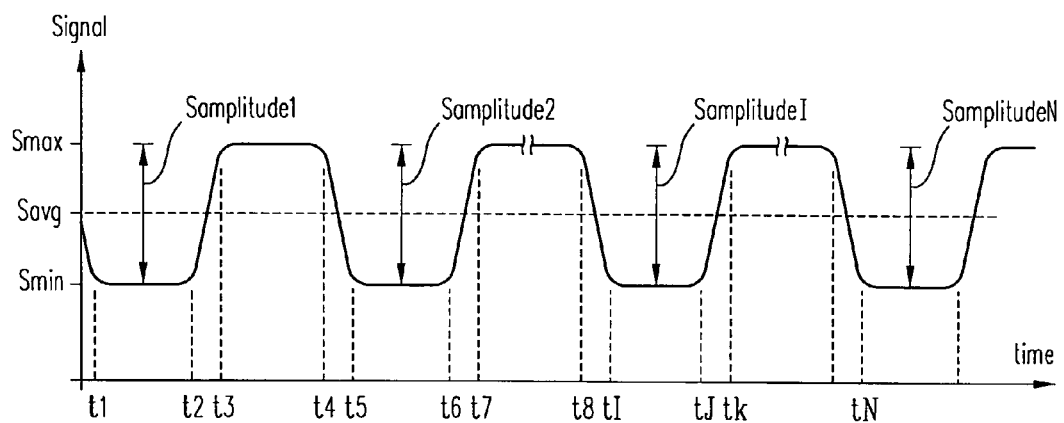
FIG. 2I illustrates, in a graph, a plot of an analog electrical signal along the y-axis as a function of time t along the x-axis, wherein signal on the y-axis is generated by a photodetector sensitive to a wavelength of the beam of FIG. 2C in response to oscillating movement thereof, as illustrated in FIGS. 2D–2H.

The above-described measurements are performed by the detector 215 continuously and sequentially (i.e. one after another), during relative motion between the beam 219 and the wafer 230, to generate an analog electrical signal of the type illustrated in FIG. 2I. An amplitude of fluctuation of the signal Samplitude is obtained as an average over a number of cycles N, by use of a lock-in device. The amplitude of fluctuation Samplitude (FIG. 2I) indicates a change in reflectivity between the two regions.

Detecting the amplitude of fluctuation (instead of making an individual reflectivity measurement in a region) eliminates the need to determine a constant present in the individual reflectivity measurement (as a baseline Smin in the analog electrical signal). Specifically, the electrical signal varies between Smin and Smax as illustrated in FIG. 2I. For example, signal that is being measured by detector 215 is at its minimum Smin between time t1 and t2 (FIG. 2I) when the beam 219 is incident wholly within the doped region 211 (FIG. 2D) and signal reaches its maximum Smax between time t3 and t4 (FIG. 2I) when the beam 219 is incident wholly within the undoped region 213 (FIG. 2H). An amplitude Samplitude of fluctuation of the periodic signal is detected using a phase-sensitive lock-in technique to isolate the ac (alternating current) component as compared to a dc (direct current) component. Specifically, the difference Smax−Smin=Samplitude is measured by the lock-in device, and eliminates the need to calibrate the effect of Smin which is present as a baseline in the electrical signal S.

Normally, the Samplitude in each of a number of cycles is the same, i.e. Samplitude1=Samplitude2=SamplitudeI=SamplitudeN. However, in some embodiments, Samplitude in each cycle is not individually detected and instead Samplitude is averaged (e.g. by the lock-in device) over a number of cycles N, i.e. Samplitude=(Samplitude1+Samplitude2+ . . . SamplitudeI+ . . . SamplitudeN)/N. Depending on the signal to noise ratio (SNR), the number N can be one hundred or more (e.g. oscillate 100–200 times between the two regions) although in some embodiments that have a very high SNR the cycles may be as few in number as a handful (say 5–10 times).

As the incident laser beam 219 (FIG. 2F) crosses the boundary 212, beam 219 may encounter a slight discontinuity at boundary 212 in the form of a thin oxide or a dislocation in the semiconductor crystal. Due to the high sensitivity of this technique, this slight discontinuity at boundary 212 can create a spike in the analog electrical signal generated by photodetector 215. Such a spike may be present in signal (FIG. 2I), for example, between times t2 and t3 and also between times t4 and t5 (spikes are not shown in FIG. 2I).

Presence of spikes can be detected by tuning a lock-in amplifier to twice the frequency f of relative movement, and such spikes are used in some embodiments to indicate to the user a property of boundary 212. However, in most embodiments of the type described herein, the spikes are filtered out of signal which is otherwise fluctuating at the frequency f of relative motion. Specifically, in some embodiments, the spikes are treated as anomalies in signal from the photodetector, and are eliminated by applying a filter, in the form of a series of electrical gates. The gates are synchronized to twice the frequency f of relative movement, and the filtered signal is thereafter provided to the lock-in amplifier (for synchronous detection at the frequency of relative motion).

Relative motion between beam 219 and wafer 230 of the type illustrated in FIGS. 2C–2H can be accomplished in any manner, e.g. in one embodiment an optical bench (carrying the laser and the photodetector) is moved relative to a stage (carrying the wafer) which is kept stationary, while in another embodiment the stage is moved while the bench is kept stationary, while in still another embodiment the stage and the bench are both moved. The stage and/or bench can be reciprocated using a piezoelectric actuator of the type well known in the art. See stage 1218 attached to a piezoelectric actuator 1219 of FIG. 12 (described below) which is coupled to receive an electrical signal fluctuating at the frequency f at which the lock-in detector is operated to determine Samplitude.

Figure 2J:
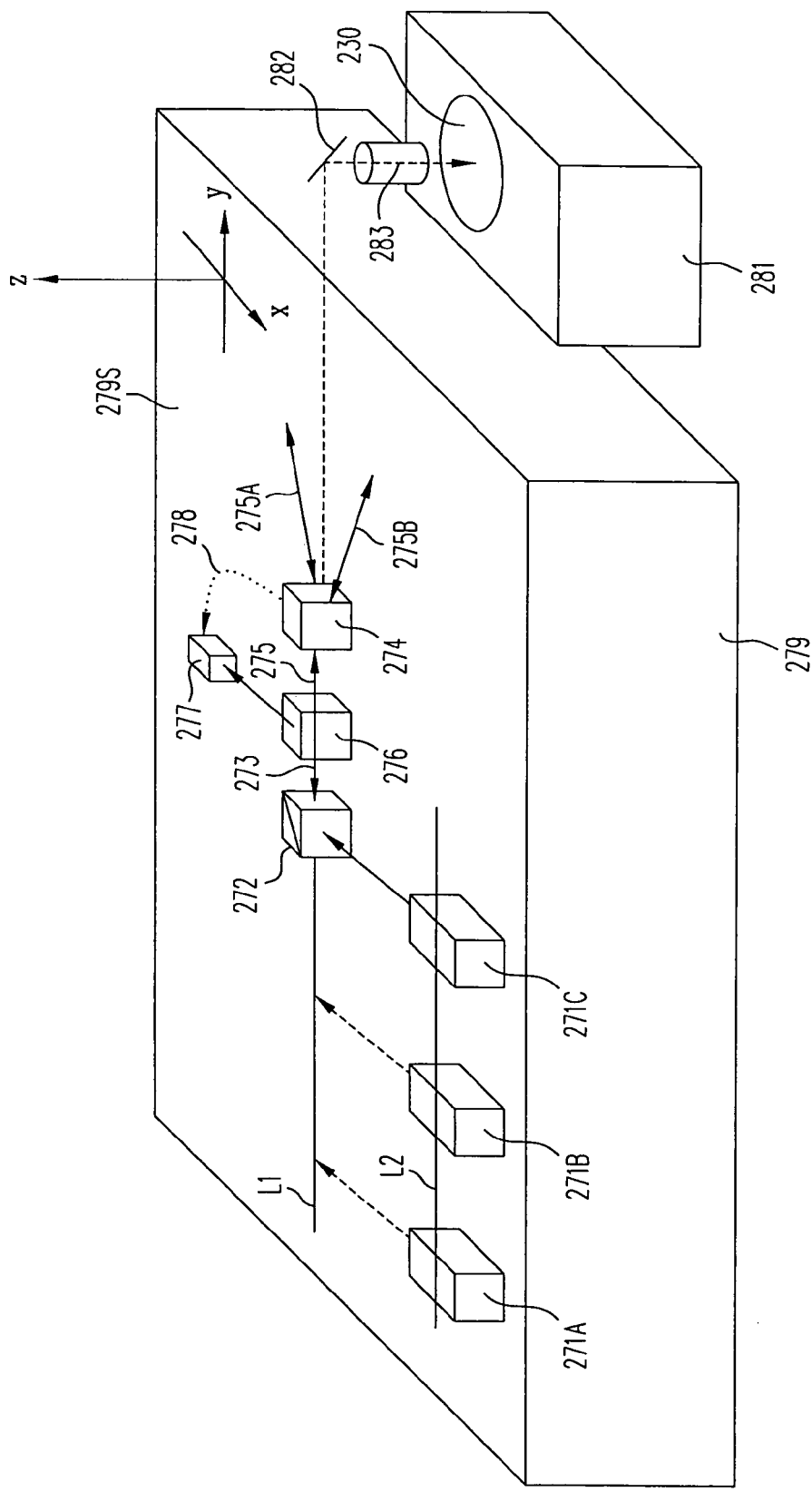
FIG. 2J illustrates, in a perspective three dimensional view, the relative positions of various optical components in an embodiment that uses three lasers for three measurements, uses an acousto-optic beam deflector for causing relative motion between the beam and the wafer, and a lock-in amplifier that uses a frequency of oscillation of the beam deflector to measure amplitude of a signal generated by the photodetector.

In certain embodiments, neither a stage nor a bench is moved (relative to ground), and instead a beam that passes therebetween is scanned relative to the wafer, e.g. between positions 275A and 275B in FIG. 2J. In such embodiments, the beam can be scanned using a beam deflector 274 in a path of the beam. A beam deflector is a device that takes an incoming beam traveling in a certain direction, and causes that beam to change its direction in a periodic manner about its original un-deviated direction. Beam deflector 274 can be, for example a scanning galvanometer mirror or an acousto-optic deflector, although any other optical device that can oscillate a beam in space can be used in other embodiments. FIG. 2J illustrates a beam deflector 274 that receives a beam 275 along the y axis from a dichroic mirror 272 (after passing through a beam splitter), and mirror 272 in turn receives the beam from one of lasers 271A–271C along the x axis. Beam deflector 274 oscillates beam 275 between positions 275A and 275B that are both within the x-y plane. One example of beam deflector 274 is an acousto-optic beam deflector.

In this embodiment, optical bench 279 has a planar surface 279S that is parallel to the just-described x-y plane, and the above-described optical elements illustrated in FIG. 2J are mounted on surface 279S. Note that in this embodiment, lasers 271A–271C are mounted on surface 279S, adjacent to one another, along three positions on a line L2 that is parallel to the y axis. Moreover, mirror 272 is translatable between three locations that are opposite to the three laser positions. The three locations of mirror 272 are along another line L1 that is parallel to the y axis and therefore parallel to line L2. Moreover, beam deflector 274 is located in a path of beam 275, along line L1. Finally, a beam splitter 276 is also located along line L1, between mirror 272 and beam deflector 274.

As noted above, there are multiple ways to move a beam across the doped and undoped regions. One method uses the wafer stage to move the wafer back-and-forth under the measuring beam while the beam and detector remain stationary. The stage is oscillated over a distance sufficiently large to cover both the doped and undoped regions; for example a scan distance of 10 µm is sufficient in some embodiments. The frequency f of oscillation of the stage can be, for example, 100 hertz (one hundred oscillations per second).

The specific frequency f that is used in any given embodiment depends on a number of factors, such as the type of mechanism used to implement oscillation, the delay (also called "latency") in electronics (e.g. lock-in amplifier) used to detect an electrical signal fluctuating at frequency f, the duration available for each measurement and the number of cycles to be used therein. Note that any frequency in the range of 1 Hz to 20,000 Hz can be used. For example, if the modulation frequency is 1000 Hz, and if at least 10 cycles are required by the lock-in amplifier to generate a reflectance measurement, then 10 milliseconds are required to perform each reflectance measurement. In one example, the throughput is 30 wafers per hour, or 120 seconds per wafer, with each wafer having a measurement taken in at least ten regions.

Note that instead of oscillating the stage, an optical bench carrying all the optical elements can itself be oscillated, although the mass of the optical bench is at least an order of magnitude larger than the mass of a stage. Another method uses an acousto-optic deflector to oscillate the laser beam slightly about the propagation axis. In most embodiments, the photodetector stays stationary since it is sufficiently large to capture the reflected radiation from the end points of oscillation. Note however, that in a few embodiments, the photodetector may also be oscillated, along with the laser beam, e.g. if the photodetector is smaller than the amplitude of oscillation (i.e. the distance between the two endpoints thereof).

A sound-wave traveling inside an optical crystal, e.g. GaAs, sets-up a diffraction grating for a light beam traveling in the perpendicular direction to the sound wave. The diffraction grating deflects the light beam at an angle proportional to the frequency of the sound-wave. Scanning of the light beam is achieved either by changing the sound-wave frequency at the predetermined frequency f or by modulating the amplitude of the sound-wave at the predetermined frequency f. As a slight variation, both the stage and the acousto-optic deflector are operated simultaneously at different frequencies, and the signals at the sum and/or difference frequency is detected by the lock-in amplifier.

Referring to FIG. 2J, in several embodiments there are additional elements located after beam deflector 274, such as the following devices: an objective lens 283, wafer 230 which is being evaluated, and a stage 281 on which the wafer is mounted. Depending on the relative orientations of the stage 281 and the bench 279, there may be additional optical elements such as a mirror 282 therebetween. Note that stage 281 can be used to move wafer 230 relative to the oscillating beam in the x, y and z directions. Specifically, stage 281 can be used to move wafer 230 in the vertical direction along the z axis to adjust focus, and in a horizontal plane to adjust the position of a test structure relative to the incident beam from mirror 282 that in turn receives the oscillating beam from acousto-optic deflector 274 and sends it to objective lens 283.

Moreover, beam positions 275A and 275B are shown exaggerated in FIG. 2I, and it is to be understood that they are sufficiently close so that the reflected beam passes back through the same optical elements (such as objective lens 283 and beam deflector 274) and is incident on a beam splitter 276 that deflects a portion of the reflected light to a photodetector 277. Note that a signal indicative of the frequency f of oscillation of deflector 274 is supplied to/from (depending on the embodiment) a lock-in amplifier to which photodetector 277 is coupled, as illustrated by the dashed arrow 278.

Note that in most embodiments of the invention, a beam that is incident on the wafer is same as the beam that is generated by a laser. Specifically, there is no intermediate secondary source for the incident beam, which is opposite to the teaching of Jiang et al. because Jiang et al. require an emitter 14 to be excited by a pulse P1 (from an optical source 12.

Similarly, in most embodiments of the invention, the portion of the reflected beam from wafer 230 that is detected by photodetector 277 is directly converted to electrical signal indicative of the properties of wafer 230. Specifically, there is no intermediate optical element such as an electro-optic sensor that is utilized in conjunction with a second beam to facilitate the detection of the probe beam. This detection method is in contrast to the teaching of Jiang et al. because Jiang et al. require the probing pulse to be detected via its interaction with a second pulse P2 in an electro-optic sensor 32 made of a 2 mm thick <110> ZnTe crystal.

A specific laser of FIG. 2J that is to be used in a measurement of the type described herein is selected in some embodiments by appropriately positioning dichroic mirror 272 along the y axis, at a predetermined location opposite to the selected laser. In FIG. 2J, mirror 272 is illustrated as being located opposite to laser 271C, although mirror 272 may be moved (along a rail that is not shown) to another location opposite to laser 271B or to yet another location opposite to laser 271A, thereby to select the wavelength to be used in illuminating the front surface of the wafer.

Instead of moving a single mirror 272, in an alternative embodiment three mirrors (not shown) are rigidly mounted relative to the respective lasers, and each mirror is used to reflect a beam only when its respective laser is turned on, by using dichroic mirrors with different transition or cut-off wavelengths. For example, when laser 271B is in use, lasers 271A and 271C are turned off, and a mirror 272B (not shown) located opposite to laser 271B reflects the beam from laser 271B along the y axis, while a corresponding mirror 272C (FIG. 2J) in the path of such a beam simply passes this beam therethrough. In one example of such embodiment, lasers 271A, 271B, and 271C must be arranged in the order of decreasing wavelength, i.e. laser 271A has the longest wavelength ($\lambda 1$), laser 271C has the shortest wavelength ($\lambda 3$), and laser 271B has a wavelength in between ($\lambda 2$). And then mirror 272B is designed to reflect wavelength $\lambda 2$ but transmit wavelength $\lambda 1$, whereas mirror 272C is designed to reflect wavelength $\lambda 3$ and transmit both wavelengths $\lambda 1$ and $\lambda 2$. Mirror 272A, being the first one in the series, could be chosen to reflect all wavelength.

In several embodiments of the type described above, a beam that is oscillated forms spots at positions 309*a* and 309*b* (FIG. 3A) on the wafer at two different times which occur at the two ends of beam oscillation along a straight line L. A scanning distance Dscan between the spot positions 309*a* and 309*b* is selected to be sufficiently large so that the spots do not overlap one another (at the extreme ends of the oscillation). Therefore, the scanning distance Dscan is selected to be (in these embodiments) greater than a diameter of the two spots, namely Bdiameter. Moreover, in these embodiments line L is selected to be perpendicular to a boundary 302 between doped region 301 and undoped region 303. Note that since the undoped region 303 is co-extensive with body 306, and for this reason region 303 is shown not hatched in FIGS. 3A and 3B.

Figure 3A:
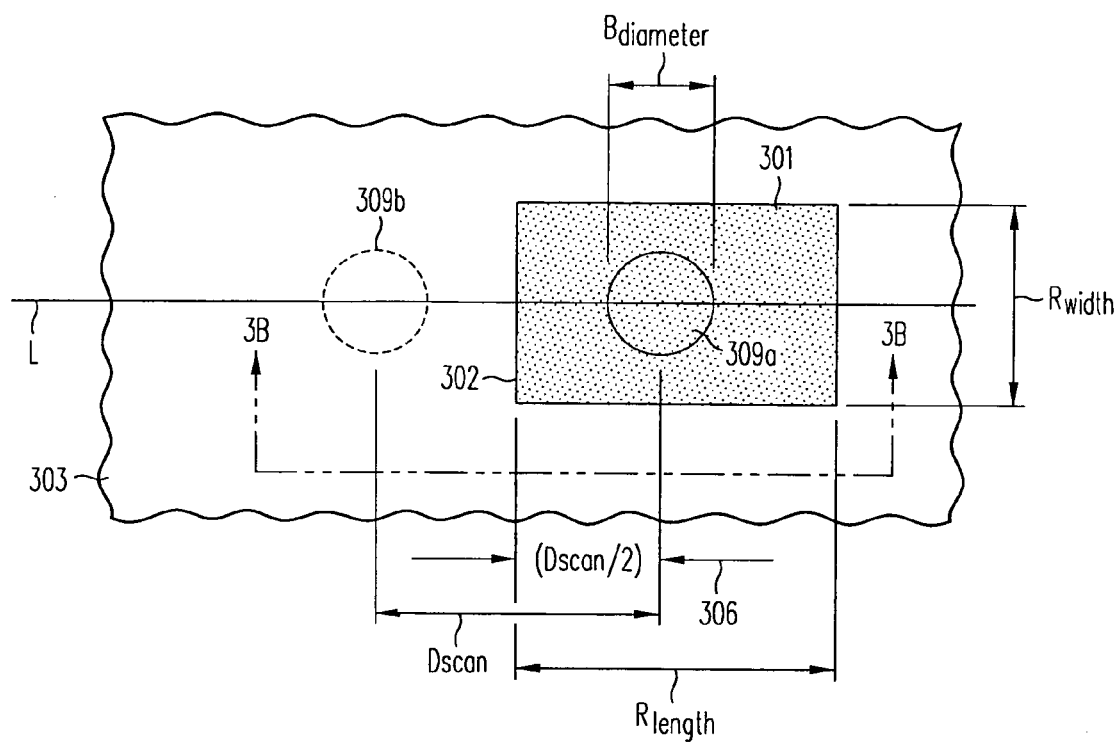
FIGS. 3A and 3B illustrate various dimensions of the test structure relative to the beam incident thereon for use by a method of the type described herein.

The width and length of doped region 301 of a test structure as shown in a plan view in FIG. 3A (see dimensions Rwidth and Rlength) are selected to be sufficiently large for region 301 to completely enclose the spot at position 309*a* (which is formed at an extreme end of oscillation, as described in the previous paragraph). Specifically, Rwidth and Rlength are selected to be greater than the Bdiameter. Such a test structure is used in some embodiments wherein dimensions of regions of transistors of integrated circuits are much finer than Bdiameter. In all other respects doped region 301 is identical to other doped regions that are normally formed as portions of integrated circuits that are to be diced from the wafer for use in the normal manner.

For example, depth of the doped region 301 (see $z_j$ in FIG. 3B and in FIG. 6E) is same as a corresponding depth of such integrated circuit doped regions (such as junction depth of source/drain regions or channel regions of a transistor). Note that the term "junction depth" is used to indicate the distance from the front surface to which dopants have been implanted in case of a junction (i.e. distance of interface 304 (FIG. 3B) from front surface F) whereas the term "profile depth" is used in a more generic situation to indicate a corresponding depth for any implant or other region that may or may not form a pn junction.

Any number of test structures may be formed and evaluated to obtain a measure of corresponding properties of the regions to be evaluated (e.g. one test structure may be formed for evaluating source regions whereas another test structure may be formed for evaluating well regions). Furthermore, there may be any number of test structures in relation to the number of integrated circuits (e.g. there may be a couple of test structures for each integrated circuit to evaluate the source and well regions therein, or a pair of test structures may be used to evaluate the source and well regions of a group of integrated circuits).

As noted above, an analog electrical signal is generated by a photodetector, and this signal has a number of characteristics that depend on the various dimensions of the test structure and on the frequency of oscillation f. For example, the duration tmax for which the signal remains at its maximum value S1 is determined by the duration for which a spot at position 309*b* remains completely within undoped region 303 (at any time between t1 and t2 in FIG. 3C). As soon as a portion of the beam falls across the boundary 302 (as the beam is moved in a direction from left to right along line L) into the doped region 301, signal starts dropping (at time t2 in FIG. 3C).

The drop in signal continues while the beam straddles the boundary 302, until the beam has completely crossed the boundary 302 (at time t3). Thereafter, signal remains steady at its minimum value S2 while the beam reaches its extreme end of oscillation at spot position 309*a*, reverses the direction of oscillation to approach boundary 302 (along line L in the direction from right to left). At this time, signal starts to rise, and continues to rise while the beam straddles the boundary 302, until the beam has completely crossed the boundary 302 (at time t5). Then signal remains steady at the maximum value S1 while a spot at position 309*b* formed by the beam is completely enclosed in region 303.

Figure 3B:
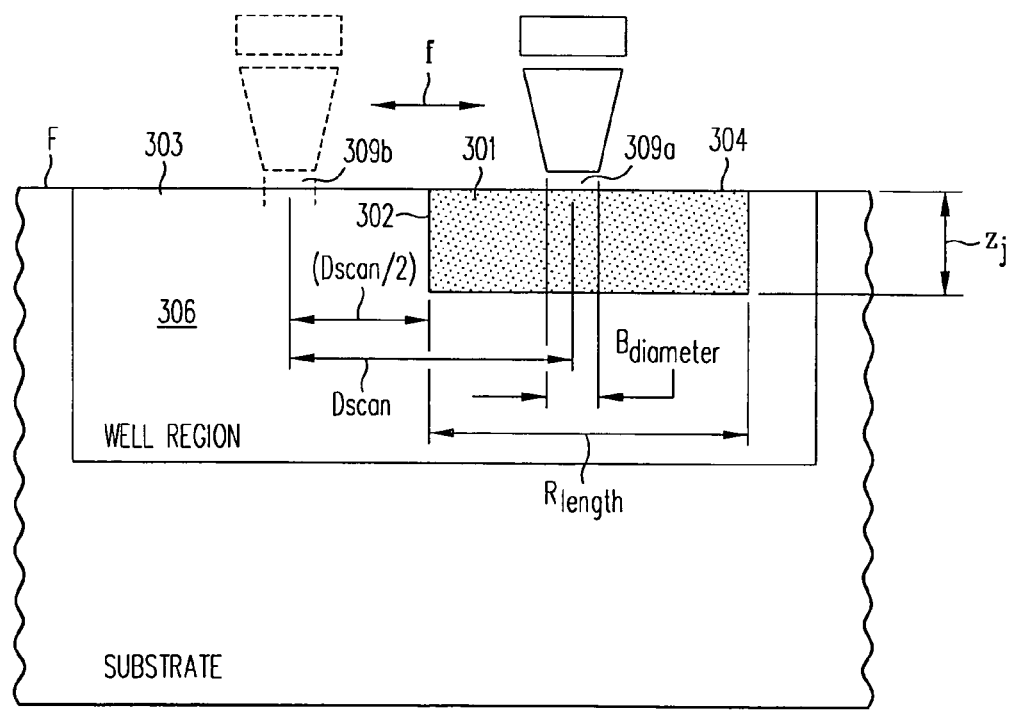
Figure 3C:
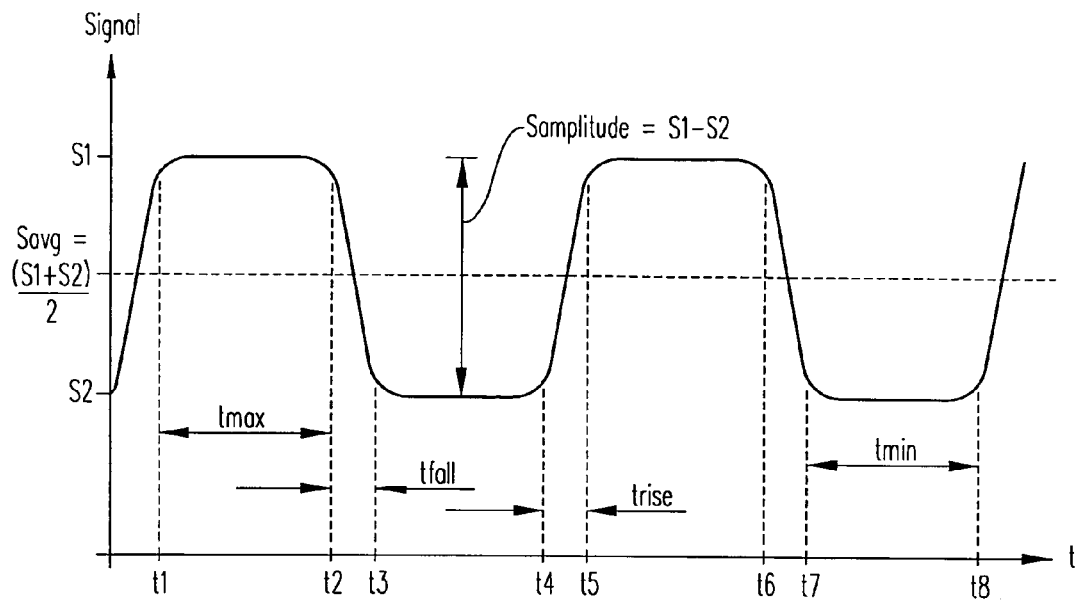
FIG. 3C illustrates, in a graph, the continuous nature of the signal sensed by the photodetector, including the durations tmax and tmin for which the signal remains steady and the durations tfall and trise during which the signal falls and rises respectively.
Figure 3D:
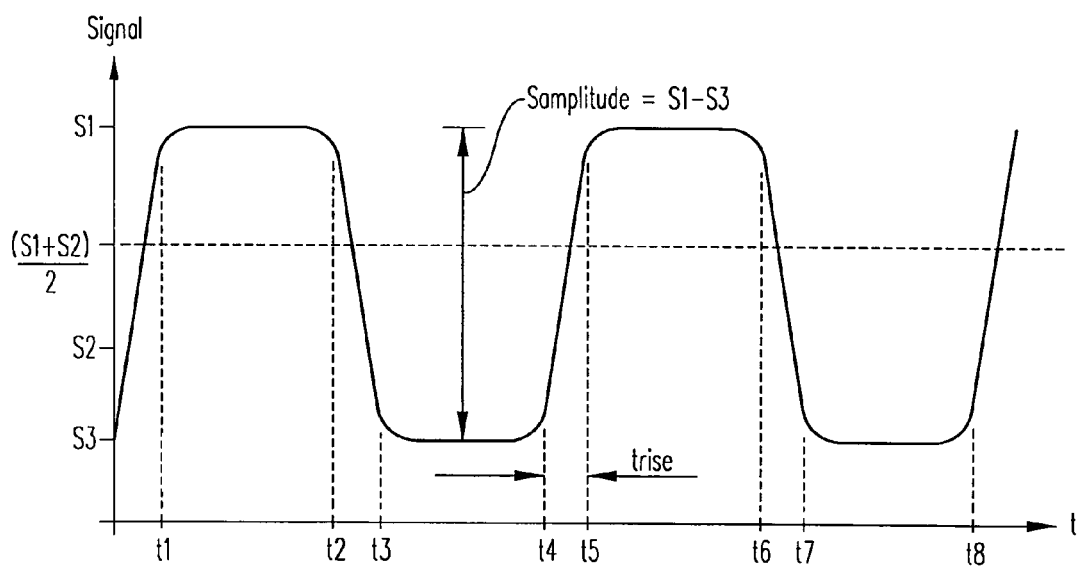
FIG. 3D illustrates, in a graph, an increase in amplitude of the analog fluctuating electrical signal of FIG. 3C which can happen in case of higher dopant concentration and/or deeper profile depth (e.g. $z_j$<700 micrometers), and/or longer wavelength of probe beam as compared to a structure which generates the signal of FIG. 3C.
Figure 8A:
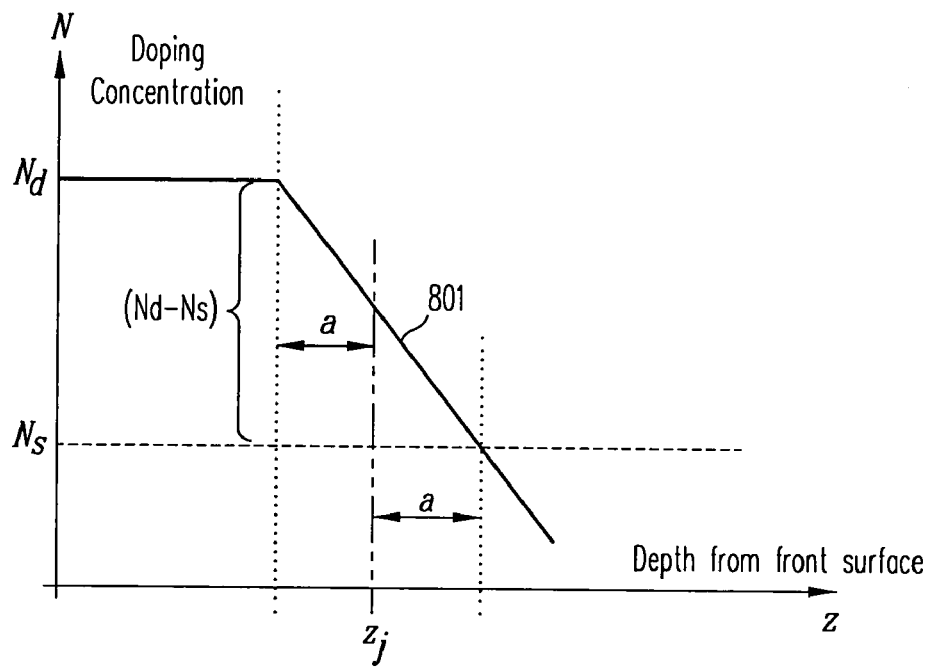
FIG. 8A shows a simplified graph of doping concentration (N) as a function of depth (z) from a front surface of a wafer in a test structure, which resembles actual doping profile in real samples in the same wafer.
Figure 8B:
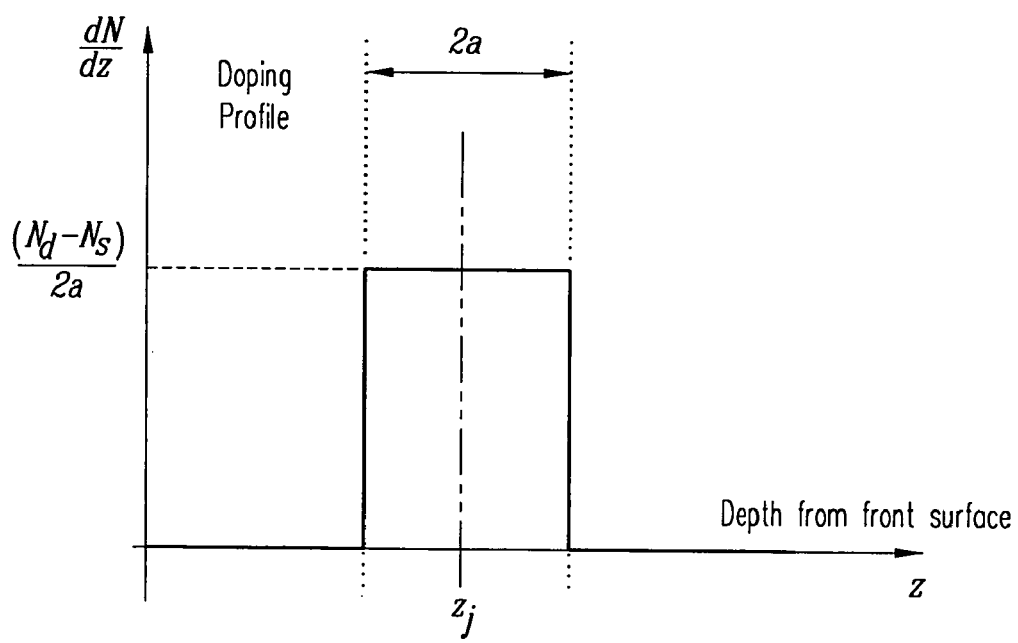
FIG. 8B shows the derivative of the graph in FIG. 8A.

Samplitude=S1−S2 indicates a difference in reflectivity between the two regions 301 and 303, and is used in some embodiments to obtain a property of the wafer. For example, the just-described reflectivity change measure (i.e. Samplitude) is compared with certain preset maximum and minimum limits on such a reflectivity change measure (which may be predetermined from a reference wafer or from a model), assuming all other properties remain the same. In such a case, an increase in Samplitude (as shown in FIG. 3C) from a structure known to be good (as shown in FIG. 3B) can indicate any of (a) higher doping concentration, (b) deeper profile depth, and (c) less abrupt doping profile. In another example, a total of three values of the reflectivity change measure (in the form of Samplitude) are obtained using each of three laser beams of different wavelengths. The three values of the reflectivity change measure are used to obtain measures of peak ($N_d$) of the dopant profile, depth ($z_j$) of the dopant profile, and abruptness (a) of the dopant profile. A model of these three properties that is used in some embodiments is illustrated in FIGS. 8A and 8B and described below.

Figure 3E:
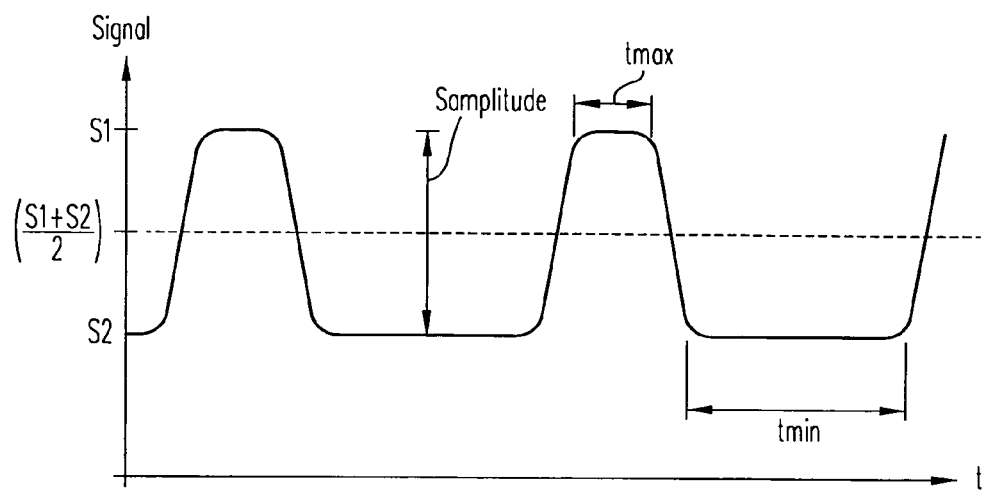
FIG. 3E illustrates, in a graph, a reduction in duration tmax during which time signal remains at its maximum value and an increase in duration tmin during which time signal remains at its minimum value, which happens when beam positions 309a and 309b of FIG. 3B are not equidistant from a boundary 302 between the doped region 301 and undoped region 303 (specifically illustrated herein is the situation when the beam spends more time in the doped region than in the undoped region).
Figure 3F:
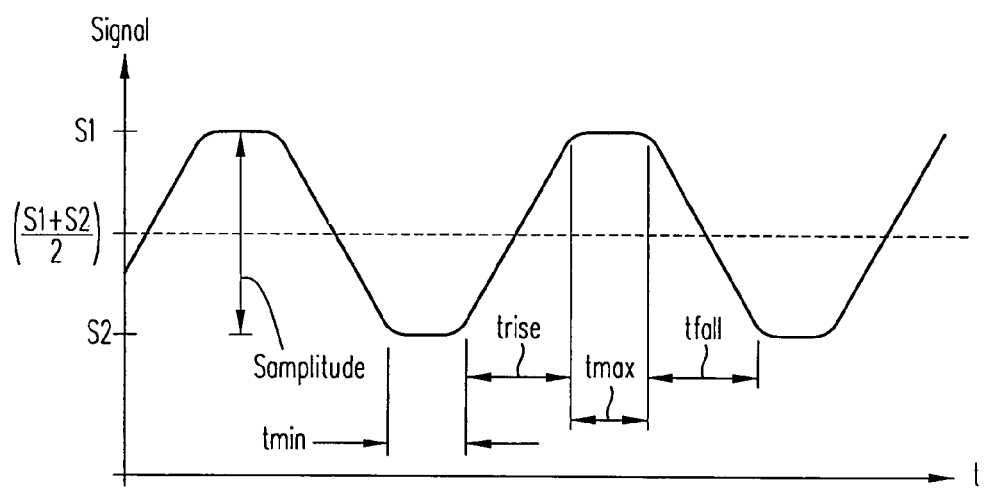
FIG. 3F illustrates, in a graph, the increase in durations trise and fall during which time the signal respectively rises from its minimum value to maximum value and vice versa, which happens in a situation wherein a boundary 302 between the doped region and the undoped region is less abrupt than in a structure which generates the signal of FIG. 3B.

The signal generated by the photodetector contains additional information other than the reflectivity change measure Samplitude. Specifically, the maximum signal value Smax, and the minimum signal value Smin are respectively indicative of the reflectance of the two regions where the measurements are made. Moreover, the duration tmax for which the signal stays at its maximum value, and the corresponding duration tmin for which the signal stays at its minimum value can also be compared with each other. As shown in FIG. 3E, if tmin is greater than tmax, the beam is spending more time in the undoped region than in the doped region (i.e. unequal beam scan). Furthermore, the duration trise (FIG. 3F) during which the signal rises to its maximum value from its minimum values can be indicative of a property of the boundary. For example, if trise of a production wafer is greater than trise of a reference wafer, then this is an indication that the boundary between the doped region and the undoped region of the production wafer (FIG. 3F) is more diffuse than the boundary of the reference wafer (FIG. 3C).

Figure 3G:
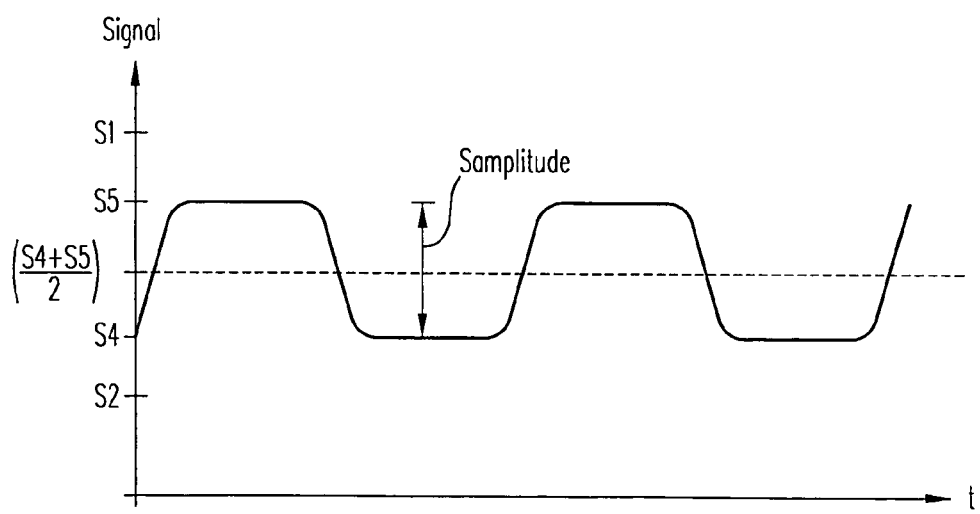
FIG. 3G illustrates, in a graph, a reduction in amplitude of signal wherein the beam spends equal time in the doped and undoped regions but the beam scan (distance Dscan between positions 309a and 309b of FIG. 3A) is less than the beam diameter (distance Bdiameter).

As noted above, the beam scan distance Dscan (FIG. 3A) across the doped and undoped regions is preferably greater than the diameter Bdiameter (which is around 2 microns in one example) of a spot formed on the wafer, in order to maximize the accuracy in detection of signal Samplitude. Therefore, in one example, Dscan is 4 microns. As the scan distance is reduced in any region, the beam spends less time with its spot fully enclosed in that region, thereby to reduce the duration for which the signal remains at its maximum value or minimum value. As illustrated in FIG. 3G, when the Dscan is less than Bdiameter, the value of Samplitude is reduced (i.e. smaller than S1–S2). In such a case, the fluctuating signal has a reduced amplitude S5–S4 which in turn results in reduced sensitivity (due to truncated Samplitude) to the change in reflectivity between the regions.

Although some embodiments generate such a truncated oscillating signal (which oscillates between S4 and S5 as shown in FIG. 3G although the true maximum and minimum are at S2 and S1 respectively), most embodiments are designed to allow the oscillating signal to reach its full maximum value and full minimum value (by ensuring that the beam's spot is at least momentarily enclosed fully within each region by making the regions sufficiently large). The lower limit on the scan distance Dscan depends on the smallest value of Samplitude that can still be detected and correlated to the change in reflectivity between the regions, which in turn is determined by the noise of the system. Typically, the minimum detectable value of Samplitude is set at a signal-to-noise ratio of 1.

Although in some embodiments, a beam is scanned between two adjacent regions, in other embodiments, the beam may be scanned between two regions that are separated from one another, e.g. by one or more other regions.

Figure 3H:
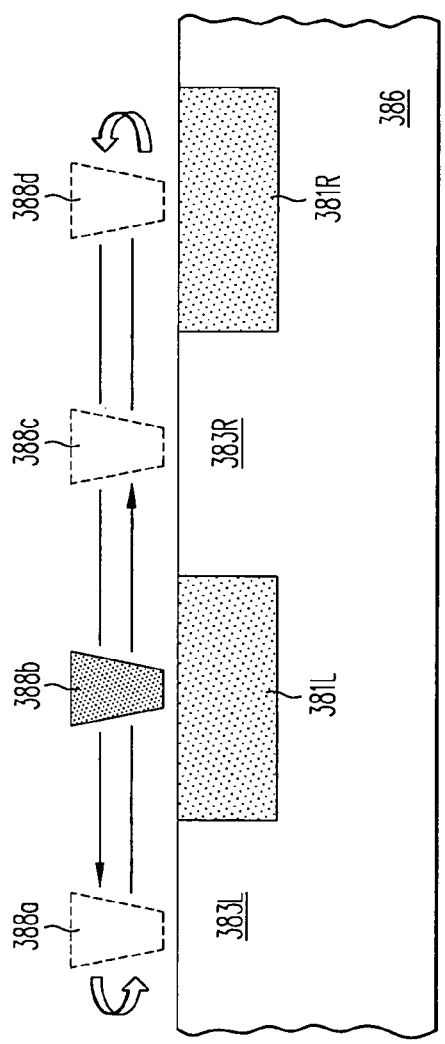
FIG. 3H illustrates, in a side view, oscillation of a beam along a line across alternating fingers of doped and undoped regions.

For example, FIG. 3H illustrates the scanning of a beam between extreme positions 388a and 388d that are respectively located over an undoped region 383L and a doped region 381R, and two additional regions 381L and 383R are present therebetween. In such a case, the beam is swept through positions 388b (at which the beam is shown currently located) and 388c that are respectively located over doped region 381L and undoped region 383R.

Figure 3I:
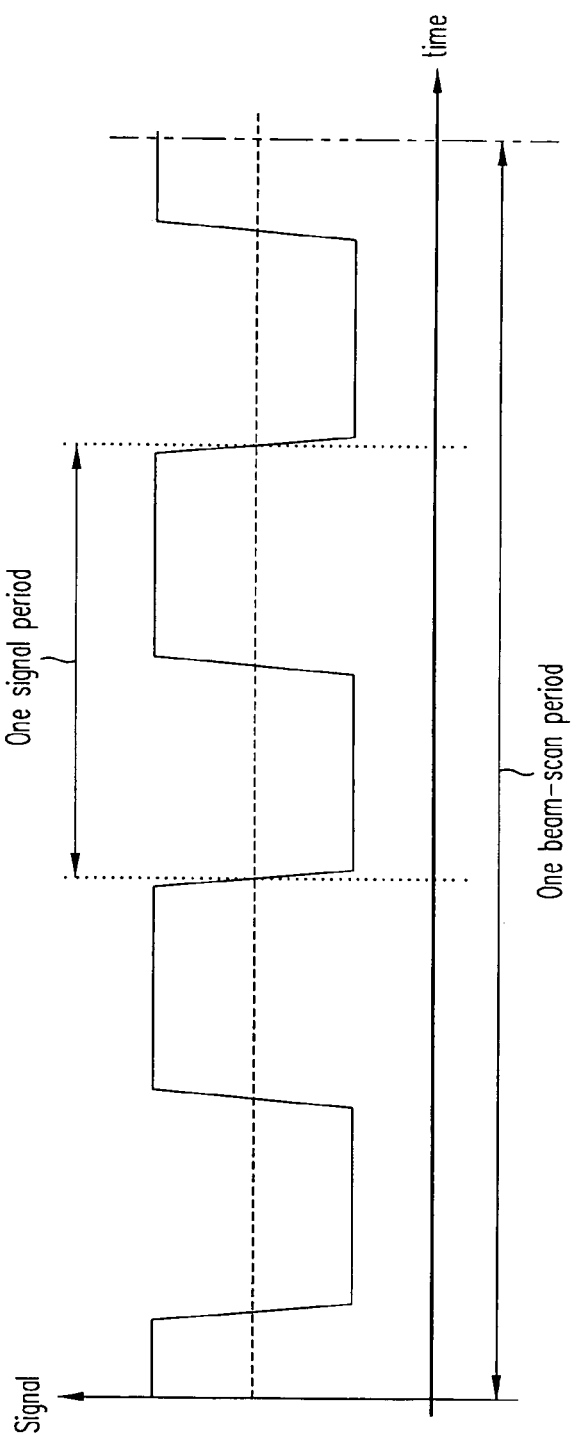
FIG. 3I illustrates, in a graph, the fluctuating electrical signal generated by a photodetector when oscillating the beam as illustrated in FIG. 3H.

A fluctuating electrical signal generated by a photodetector in the just-described embodiment has a period that is one-third of the period of oscillation of the beam, as illustrated in FIG. 3I. Therefore, although in certain embodiments the frequency of oscillation of the beam (also called "beam-scan frequency") is same as the frequency of fluctuation of the electrical signal (also called "signal frequency"), in other embodiments the two frequencies can have a non-identical relationship (i.e. need not be equal).

For example, scanning of the beam across one or more pairs of intervening doped and undoped lines results in a signal frequency that is an integral multiple of the beam-scan frequency (in FIG. 3I, one doped region 381L and one undoped region 383R are together considered a single pair that intervene between regions 383L and 381R). The test structure is designed with the width of the lines larger than or equal to Bdiameter. The signal sensed by the photodetector is analyzed in some embodiments with a lock-in amplifier set to measure the nth harmonic of the beam-scan frequency. In the example illustrated in FIG. 3I, n=3. Instead of a lock-in amplifier, in an alternative embodiment a fluctuating component in signal may be identified by digitally sampling the photodetector's output signal and a computer analyzing the samples to identify Samplitude at the appropriate frequency (which is based on the frequency of mechanical oscillation of the beam relative to the test structure and also based on a pattern of the test structure across which the beam is swept). Note that in other embodiments, instead of a pair of lines, a single line of a different material (than the two regions) may intervene, in which case the electrical signal has three steps (horizontal flat regions) instead of two steps.

Figure 3J:
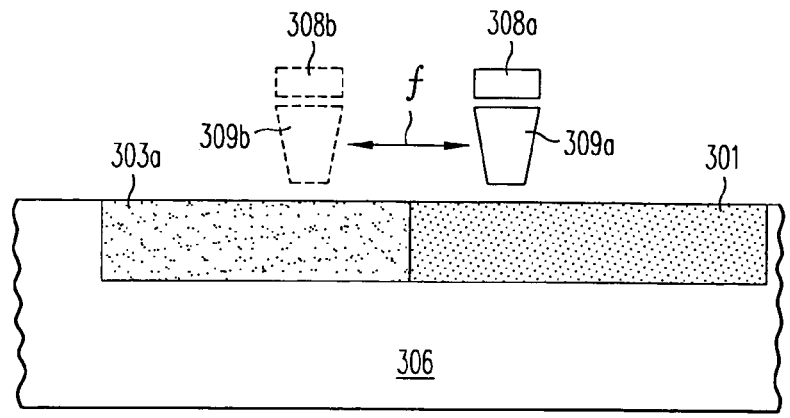
FIGS. 3J–3N illustrate application of an oscillating beam measurement of the type described above to different structures in various embodiments of the invention.
Figure 3K:
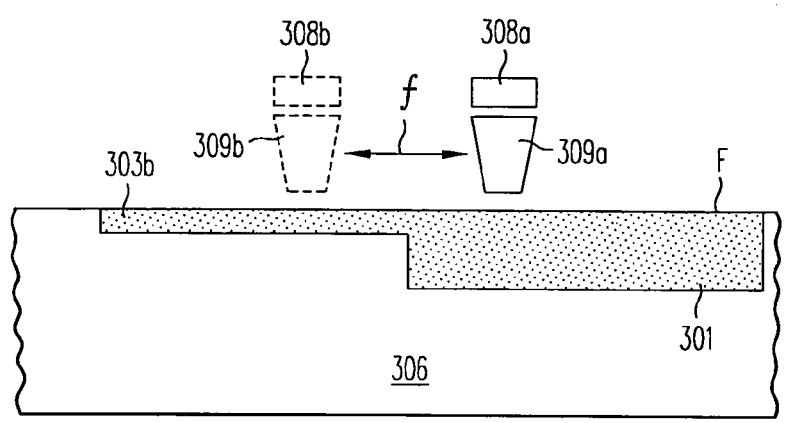

Although regions 301 and 303 (FIG. 3B) have been described above as being doped and undoped regions, reflectivity change across regions of other materials and/or dimensions can also be determined by acts 202–206 described above. For example, FIG. 3J illustrates measurement (by acts 202–206) of reflectivity change between a lightly doped region 303a and doped region 301. FIG. 3K illustrates measurement (by acts 202–206) of reflectivity change between a shallow doped region 303b and doped region 301. In such embodiments, a change in the Samplitude measurement between successive wafers being fabricated is used for process control. The Samplitude measurement may be directly compared against predetermined limits, and if not within the range then a change is made in a process control parameter (also called "process parameter") used in fabrication of regions 303b and 301. Alternatively, the unknown properties in regions 303a and 303b may be looked up using Samplitude data obtained from reference samples with known properties.

Figure 3L:
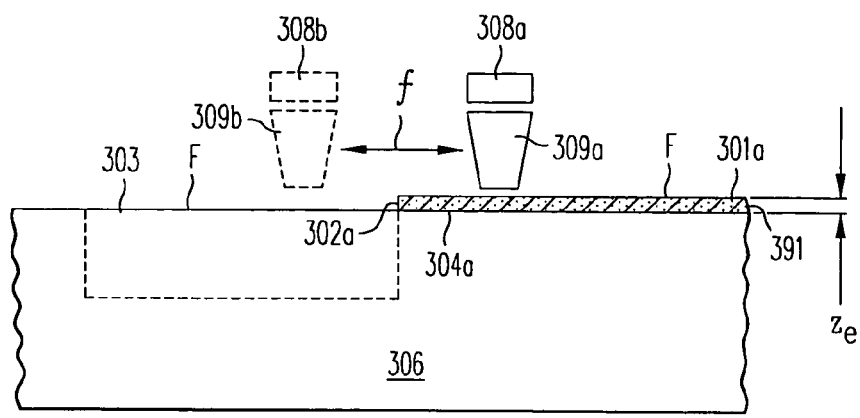

FIG. 3L illustrates measurement (by acts 202–206) of reflectivity change between undoped region 303 and a region 301a that is formed by a layer 391 of dielectric or conductive material (e.g. gate oxide or metal). Note that in the embodiment illustrated in FIG. 3L, the front surface F of the wafer is not planar, because the just-described layer 391 is formed over a planar surface 304a of the semiconductor material that forms the substrate (substrate 307 is explicitly shown in FIG. 3N). Therefore, front surface F of the wafer is planar in region 303 of the substrate, discontinuous at boundary 302a and planar again over region 301a of the dielectric/conductive layer 391.

The vertical distance between the two planar regions 301a and 303 (in a direction of thickness of the wafer) is thickness $z_L$ of layer 391. Surface 304a forms an interface between substrate 306 and layer 391. In such embodiments, a change in thickness $z_L$ of layer 391 from one wafer to another wafer during semiconductor wafer fabrication (e.g. of layer 301a) results in a corresponding change in the Samplitude measurement which is used for process control in some embodiments. Note that the thickness of layer 391 is much less than the depth of focus of the incident beam and hence the magnitude of a change in thickness $z_L$ of layer 391 has negligible effect on beam focusing.

Figure 3M:
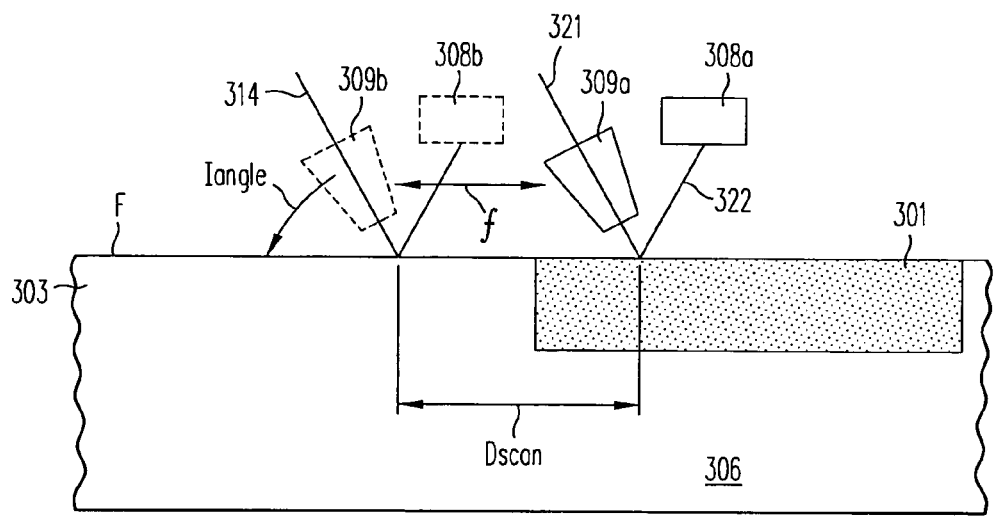
Figure 3N:
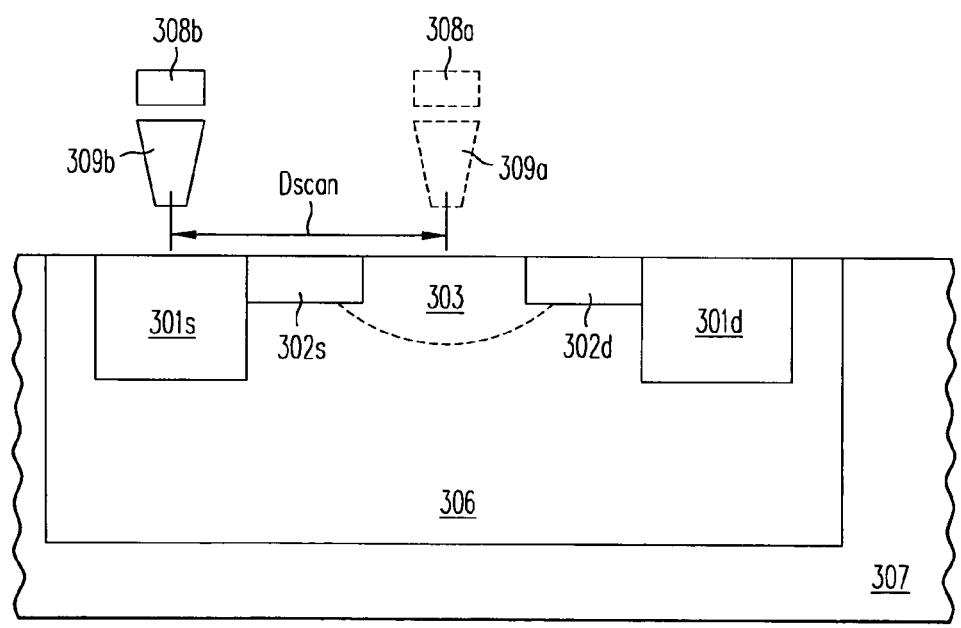

Furthermore, although in some embodiments the incident beam and the reflected portion are both normal (i.e. perpendicular) to the front surface of the wafer (see line 214 normal to surface F in FIGS. 2D–2H), in other embodiments, there may be an angle langle (FIG. 3M) which is other than 90°, between an axis 314 of the incident beam at position 309b and surface F of wafer. In such a case, a photodetector 308b is oriented at the same angle to receive the reflected portion, as will be apparent to the skilled artisan in view of this disclosure. Also, although in some embodiments the regions being evaluated are of a test structure, in other embodiments the regions of an integrated circuit are directly evaluated as illustrated in FIG. 3N, in view of this disclosure.

Whether or not regions of an integrated circuit can be directly evaluated depends on a number of factors such as the relative dimensions of the regions and a spot formed by the incident beam. The spot formed on the wafer in turn depends on, for example, the wavelength of the beam, and the focal length of an objective lens that focuses the beam on the wafer. In one embodiment of the type illustrated in FIG. 3N, the contribution of an extension region 302s (which is located between a doped region 301s and an undoped region 303) to the measurement is ignored, by filtering out any components in the analog electrical signal that are not at the frequency of relative movement (between regions 301s and 303), e.g. by use of a lock-in detector tuned to the relative movement frequency, or by using an electrical gate to block the portion of the signal that comes from region 302s.

As noted above, several embodiments do require creation of a test structure in a semiconductor wafer and subsequent non-contact measurement of change in reflectance across portions of the test structure by use of an oscillating beam. Measurement of such test structure reflectance is used, for example, to estimate the depth of a doped region in a transistor, e.g. by forming a test structure of doped regions of the same dosage as in the transistor. In several such embodiments, the estimates can be of a dimensional property (such as junction depth which is one example of profile depth) and/or a material property (such as peak dopant concentration) and/or a mixed dimensional/material property (such as the gradient of dopant concentration which is also called profile abruptness).

Estimates of the type described herein can be made by comparing an attribute of a signal measured on the test structure of a wafer under fabrication with a corresponding structure on a set reference wafers having a set of known properties forming a calibration or look-up table. As noted above, use of a test structure in a production wafer as described herein provides a convenient method for determining various such properties because one or more dimensions of the test structure need not be limited to dimensions of the transistor or other devices to be used in an integrated circuit (being formed). Several embodiments use the measurement to control ion implantation and/or annealing processes for forming such regions in the next production wafer, e.g. by changing one or more process parameters such as implanted dose, annealing temperature, and thermal exposure time.

Embodiments of the type described herein have numerous advantages over the prior art methods. From the physics point-of-view, the method/apparatus of certain embodiments of the invention measure the active doping profile, since the measurement is sensitive to the majority carrier distribution, which closely follows the active doping profile. Some embodiments extract the following three properties of a semiconductor wafer resulting from doping: profile depth, profile abruptness, and peak doping concentration. From the hardware set-up and stability point-of-view, such embodiments of the invention offer easier optical beam alignment and long-term stability over the prior art.

Figure 4A:
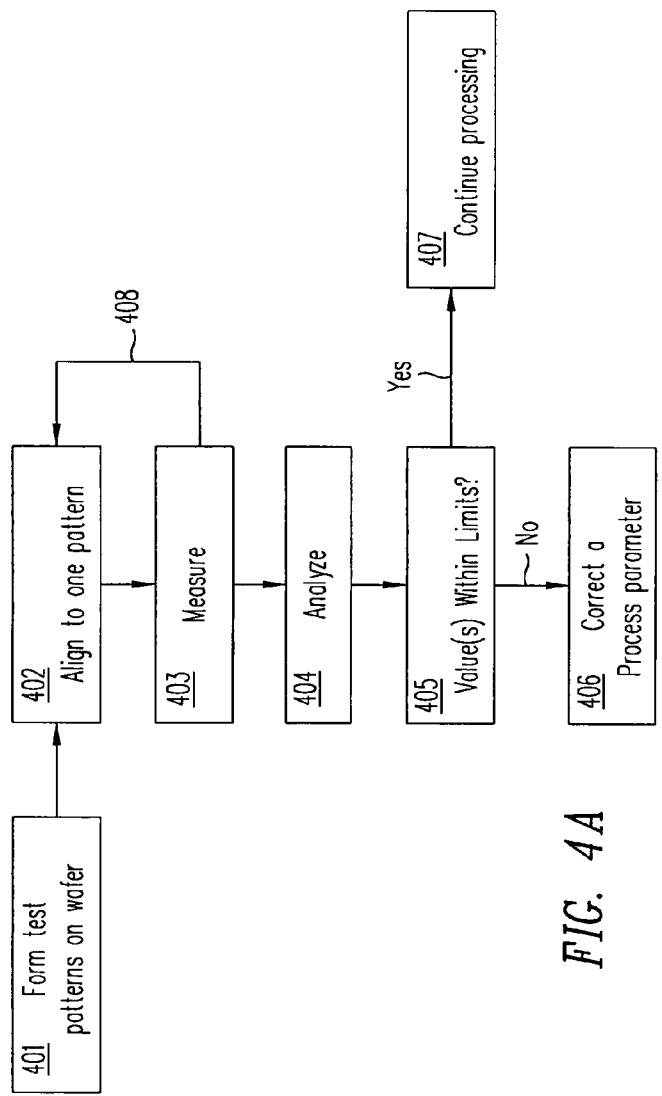
FIG. 4A illustrates, in a flow chart, acts for use of a measurement of the type described above to decide if a process for fabricating a semiconductor wafer is in control (i.e. generates wafers within predefined tolerances of material and dimension properties).
Figure 4B:
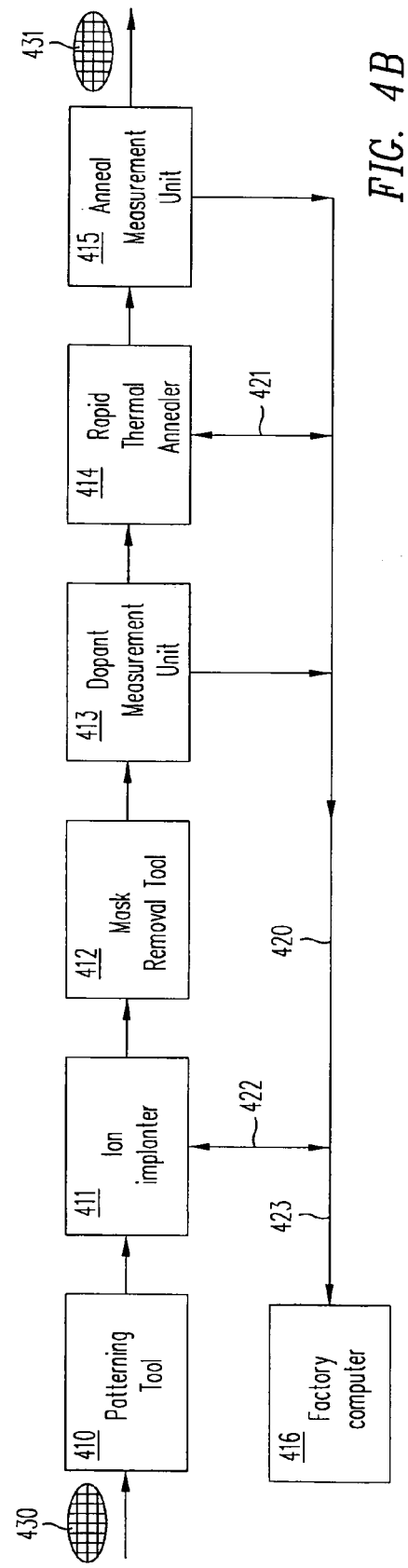
FIG. 4B illustrates, a block diagram, a wafer fabrication system including a measurement apparatus used in a process flow for wafer fabrication.

FIGS. 4A and 4B illustrate the use of certain embodiments in process control, to control the wafer fabrication process in a feedback loop. Specifically, one or more test structures are formed in a production wafer, e.g. simultaneous with transistor fabrication for integrated circuits, as illustrated in act 401 of FIG. 4A. The test patterns are preferably identical in doping characteristics to a transistor layer that is of interest. For example, if source and drain formation processes used to form regions 101 and 102 are to be controlled, then the same processes are used to form the test structure(s).

Such test structures may be open areas several microns on a side situated in open areas such as the streets between integrated circuits, and may be formed simultaneously with the formation of source/drain 101 and 102. In one embodiment, junction depth of doped regions of a transistor is to be estimated, and the test structure formed in act 401 requires implantation of dopant atoms and annealing, and depending on the embodiment such implantation and annealing may be performed simultaneously with implantation and annealing for formation of transistors of the wafer.

Once one or more test structures are formed, a wafer containing the test structures is aligned to a measurement system (see act 402 in FIG. 4A), followed by measurement of a signal indicative of a property of the doped region, using a non-contact probe (see act 403 in FIG. 4A). One or more of acts 402 and 403 may be repeatedly performed, e.g. for multiple test structures as illustrated by act 408, and may be interleaved with or performed simultaneously with other kinds of measurements as would be apparent to the skilled artisan. Act 403 may be performed by any method described herein, e.g. by performing acts 202–206 (FIG. 2A).

Thereafter, the signals from the measurements performed in act 403 are optionally processed to convert the signals into a more meaningful quantity related to one or more properties of the doped region, such as the peak, the depth and the abruptness of a profile of the implanted dopants (see act 404 in FIG. 4A). As noted elsewhere herein, such conversion is not necessary in some embodiments wherein the raw measurements are directly used in act 405 for process control (described next). The results of the analysis in act 404 are compared with predetermined control limits (see act 405 in FIG. 4A), and if the measurements fall within the limits, fabrication of the wafer is continued (see act 407 in FIG. 4A), followed by returning to act 401 (described above) to form additional test structures in the same wafer, or in another wafer. If the measurement falls outside the predetermined control limits, a process parameter that is used in fabrication of the wafer is changed (see act 406 in FIG. 4A), and depending on the deviation the current wafer may be rejected or alternatively may be processed further.

Therefore, measurement of the test structure's properties is performed in an in-situ manner during fabrication of a wafer and in one embodiment, a measurement tool 413 (FIG. 4B) is co-located with other wafer fabrication tools, such as an annealer 414, an ion implanter 411, a patterning tool 410 and an oxide mask removal tool 412. A wafer 430 (FIG. 4B) may enter a patterning tool 410, wherein patterns associated with the source and drain extensions of to- be formed transistors, and also doped regions of one or more test structures are formed on wafer 430.

Thereafter, wafer 430 is inserted into an ion implanter 411 wherein dopant atoms are implanted to form, for example, doped region 211 (FIGS. 2B and 2C) of a test structure 210 as well as one or more doped regions 221 of one or more integrated circuits 220 in the wafer. Next, the implant mask is removed by tool 412 (FIG. 4B), and the test structures in the wafer are evaluated by measurement tool 413 as described above in reference to act 403. Therefore, measurement tool 413 contains one or more items illustrated in FIG. 2J.

In some embodiments, measurement tool 413 contains all of the items in FIG. 2J, oriented relative to one another in the manner illustrated in FIG. 2J, and in addition also contains a stage that is located adjacent to and to the right side of optical bench 279 (FIG. 2J). Measurement tool 413 of such embodiments also contains a mirror to deflect the beam by 90° (regardless of its position being at 275A or at 275B or anywhere therebetween), and an objective lens that is located between the mirror and the wafer 230 (FIG. 2J).

After act 403 (FIG. 4A) is completed in measurement 413 (FIG. 4B), and if the wafer is found to have the implant properties within predetermined limits, the wafer is further processed. Specifically, the wafer is annealed in a rapid thermal annealer 414, and afterwards the test structures in the wafer are evaluated again by measurement tool 415 which is similar or identical to the above-described measurement tool 413. Since measurement tool 415 is used only after the wafer has been annealed, it is also referred to as anneal measurement tool whereas tool 413 is also referred to as an implant measurement tool.

In the embodiment illustrated in FIG. 4B, measurement signals generated by units 413 and 415 are supplied on a bus 420 that is connected via connection 422 to ion implanter 411, and via connection 421 to annealer 414, thereby to provide feedback signals to these tools 411 and 414. Alternatively, or additionally, the measurement signals on bus 420 may be provided via connection 423 to a computer 416 that is mounted on a factory floor adjacent to tools 411, 412 and 414 as well as units 413 and 415 (that are also mounted to the same floor). Due to being located on the factory floor, computer 415 is also referred to herein as a factory computer. Factory computer 416 may archive the measurement signals from units 413 and 415 for later correlation to electrical performance of electronic devices being fabricated on wafer 430. If the measurements are outside the control limits, factory computer 416 can provide corrections to ion implanter 411 and annealer 414 to return the process back to the control limit. As noted above, the feedback to ion implanter 411 and annealer 414 may also be provided directly from either or both of measurements units 413 and 415.

Figure 5A:
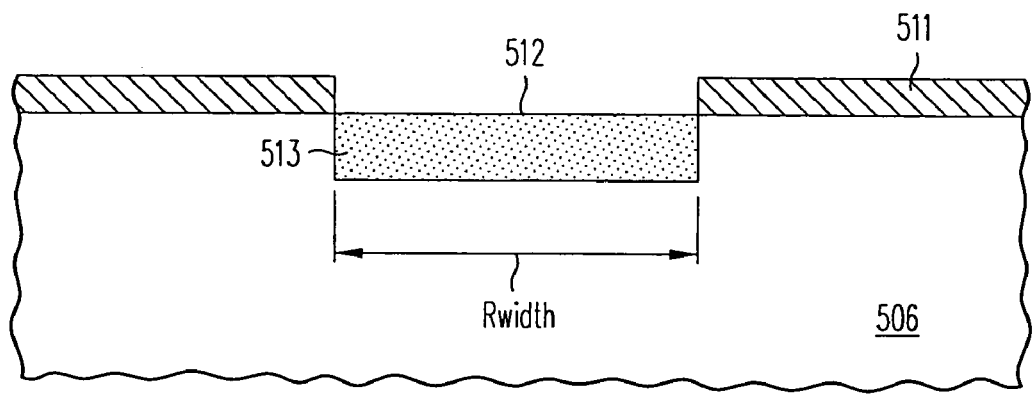
FIG. 5A illustrates, in a cross-sectional view, a test structure for characterizing the profile of doped regions of a transistor, in one embodiment of the invention.
Figure 5B:
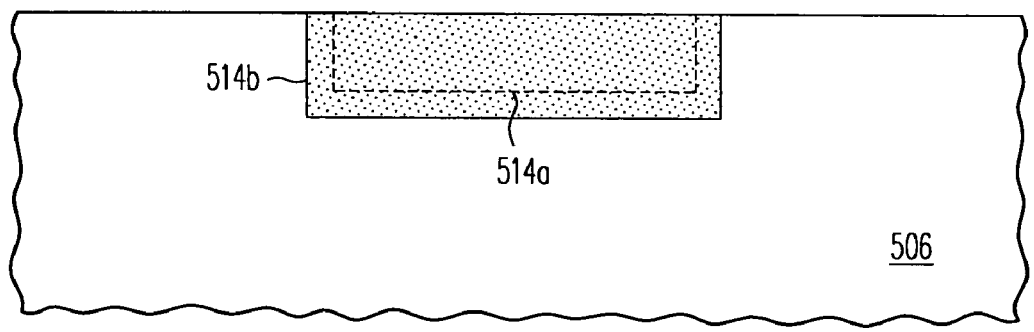
FIG. 5B illustrates, in a cross-sectional view, the test structure of FIG. 5A after removal of oxide mask 511 and annealing.

FIGS. 5A and 5B show in cross-sectional views one example of such a test structure (which forms only a portion of the wafer and it is understood that the remainder of the wafer contains at least one or more integrated circuits and may contain additional test structures). In the example of FIG. 5A, the test structure includes an ion-implanted region 513 (one region is shown by way of example, although more may be used depending on other considerations, such as the ability of the measurement system to align to a pattern, or space limitations within the integrated circuit die). Region 513 of the test structure typically has a width Rwidth of >20 µm, while its length Rlength in the direction normal to the cross section (see FIG. 3A) may also be on the order of 20 µm, but may in some cases be as large as 500 µm.

In one embodiment, an ion implanter used to form region 513 (FIG. 5A) has exactly the same energy and dose as the ion implanter used to form source/drain extension regions of a transistor that is present (as a part of the normal circuitry) in the semiconductor wafer. Ideally, the region 513 is formed in the same ion implantation step used to form the source/drain structures on the transistors, ensuring that the ion implant in the transistors and test structures are identical. The energy and dosage for a test structure may be selected to be the same as the MOS transistor for two reasons: first, it best represents the real transistor doping and second it requires no additional process steps.

Note that the dimensions of the test structure(s) are sufficiently larger than the dimensions of the regions of transistor(s), so as to enable a signal sensed from the test structure to be evaluated in the manner described herein. For example, in several embodiments, dimensions of the test structures are an order of magnitude or more larger than transistor regions because the transistor regions are normally printed much finer than the diameter of a spot formed at the surface of the wafer by a beam of illumination incident thereon during evaluation of the type described herein. On the other hand the dimensions of the test structure regions are selected to be of the same order of magnitude as the beam diameter (and depending on the embodiment, dimensions of test regions may be slightly smaller or slightly larger than the beam diameter).

In the embodiment illustrated in FIG. 5A, the dopant atoms may be implanted to a very shallow depth, typically <500 Å. In this embodiment, the implant parameters are the implant specie (B, As, P, Sb, etc), the energy (0.2 to 2 keV typically), and the dose ($1 \times 10^{14}$ to $3 \times 10^{15}$ atoms/cm² typically). The anneal parameters are typically the temperature (on order of 1000° C.), time (instantaneous to 10 sec), ramp-up rate (50 to 200° C./sec) to temperature and ramp-down time (same as ramp-up rate). After annealing, the size of the implanted region increases due to diffusion, as shown in FIG. 5B. The originally formed region 513 is shown with dashed lines as region 514a in FIG. 5B, and after annealing it becomes larger and is labeled as region 514b. Also, in FIG. 5B the ion implantation mask 511 has been removed, which was done prior to annealing.

Figure 6A:
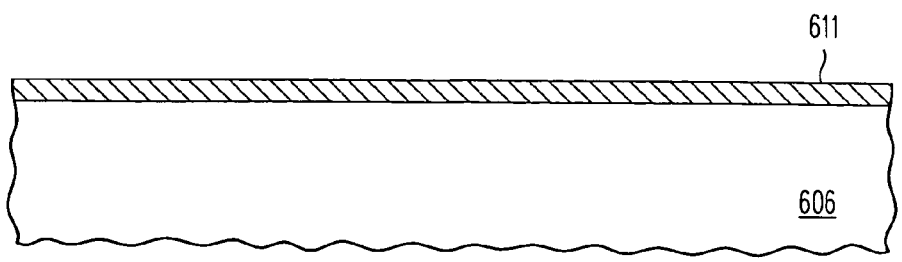
FIGS. 6A–6E illustrate, in a series of cross-sectional diagrams, a process of creating a test structure of the type illustrated in FIGS. 5A and 5B.
Figure 6B:
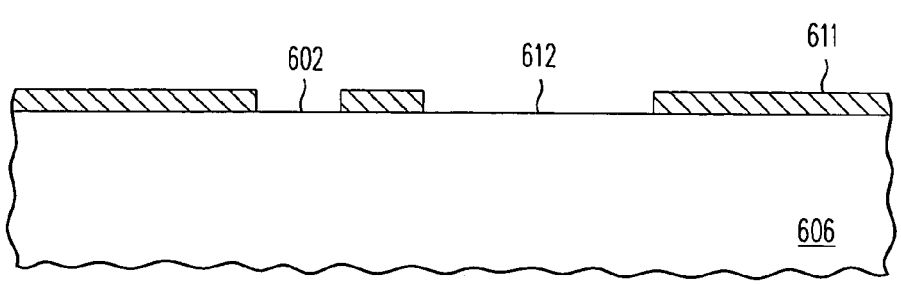

A process for making a test structure of the type described above in reference to FIGS. 5A and 5B is illustrated in FIGS. 6A–6E, for one embodiment. First, a photoresist layer 611 is applied to the surface of substrate 606 (FIG. 6A). Next, the photoresist layer 611 is patterned by exposing and developing the resist, creating a hole 612, in the photoresist layer 611 (FIG. 6B) for the test structure. The just-described acts are also used simultaneously for the creation of one or more portions of a transistor in the silicon wafer. For example, the source and drain regions, and extensions thereof may be formed simultaneously with formation of region 613, depending on the embodiment. If so, layer 611 has holes (such as hole 602) at the locations of the to-be-formed regions of the transistors, in addition to the hole 612 required for forming the test structure. Hole 602 typically has smaller dimensions than hole 612, depending on the embodiment.

Alternatively, all of the regions of the various transistors in a wafer may be formed by acts separate and different from the just-described acts for formation of a test structure, again depending on the embodiment.

Figure 6C:
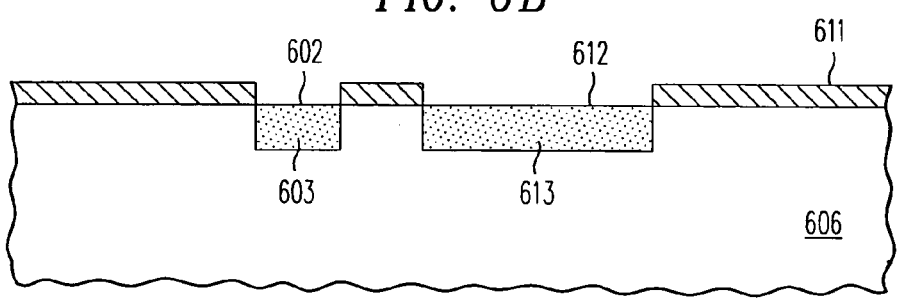
Figure 6D:
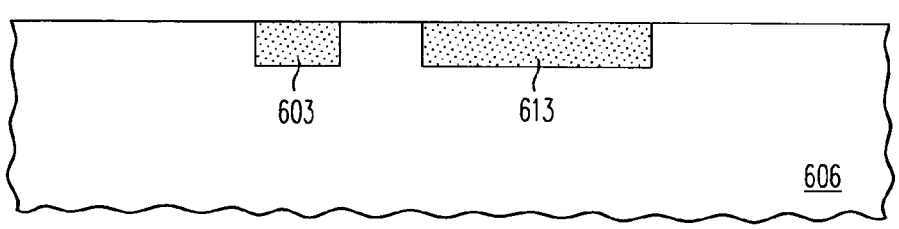
Figure 6E:
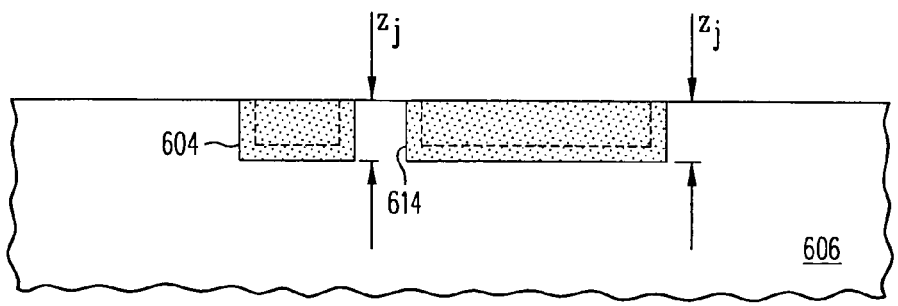

Ion implantation is applied, to form region 613 beneath the hole 612 (and beneath any additional holes 602 that may be present for the formation of transistors as noted above). Photoresist layer 611 blocks the ion implantation elsewhere (FIG. 6C). Photoresist 611 is then removed, leaving implanted region 613 in substrate 606 (FIG. 6D), and any additional regions (such as region 603) for the transistors. Finally, the wafer is annealed, causing diffusion of the implanted region 613 resulting in an expanded doped region 614 (FIG. 6E). Any additional region 603 if present in the wafer also experiences diffusion during annealing, resulting in a correspondingly expanded doped region 604.

As noted above, to measure properties of the doped region 604, a portion of the adjacent doped region 614 of the test structure in a semiconductor wafer is illuminated with a laser beam. Initially, when the beam is incident on region 614, it reflects off the surface of the wafer because of index of refraction difference between the air and the semiconductor material. During oscillation of the beam into an adjacent undoped area, the optical reflection occurs only at the surface of the wafer as described next.

Figure 7B:
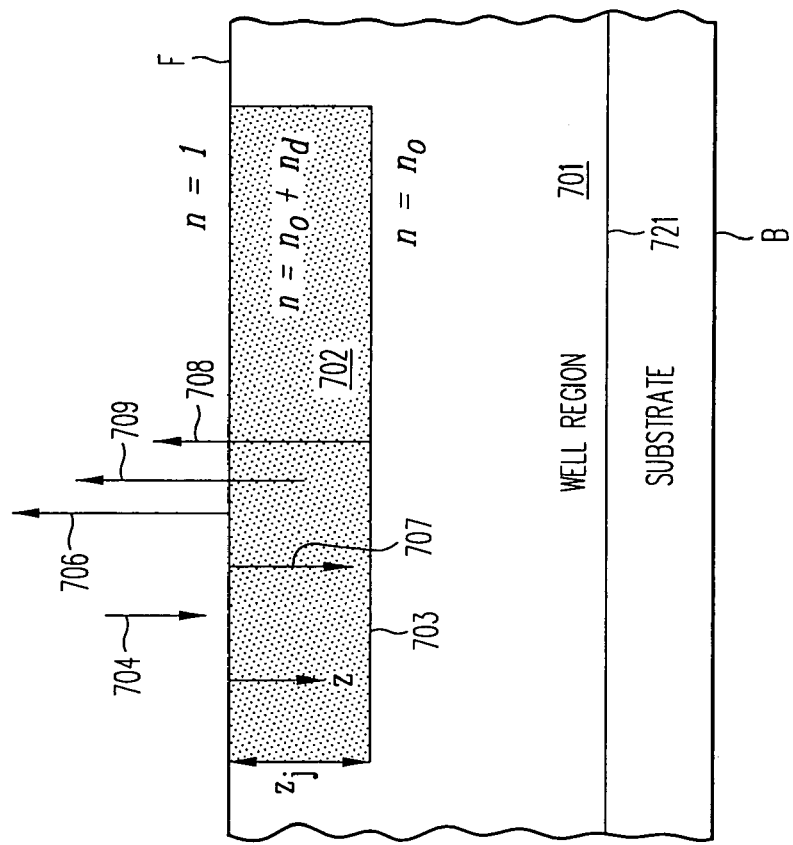
FIGS. 7A and 7B illustrate the incidence and reflection of a beam of electromagnetic radiation in a direction perpendicular to an exposed surface of an undoped material (FIG. 7A) and a doped-material (FIG. 7B).
Figure 7A:
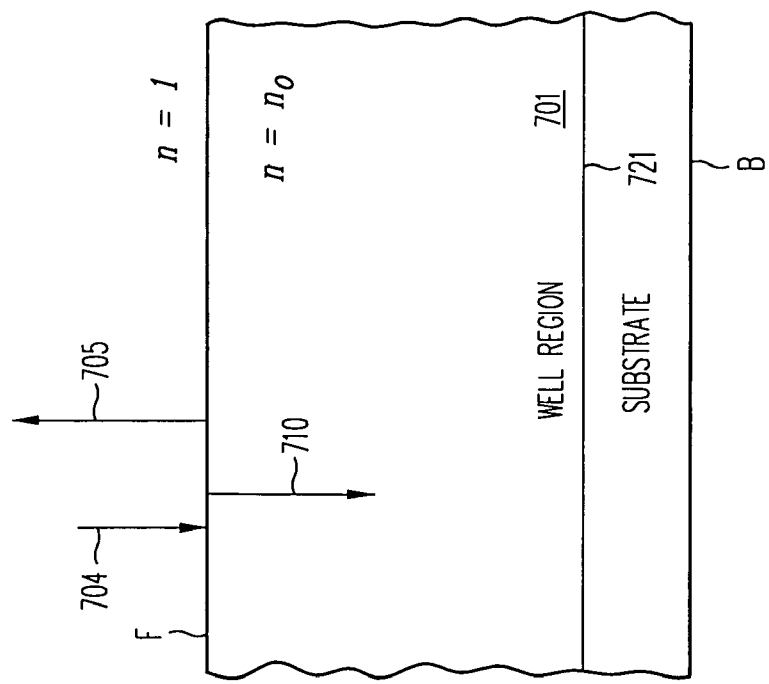

FIG. 7A illustrates a beam 704 incident on a front surface F of a wafer in an undoped or low doped region 701, a portion 705 of the beam 704 being reflected from surface F, and another portion 710 being transmitted into and absorbed in region 701. The intensity of reflected beam portion 705 is given by:

$$E_s^2 = r_s^2 E_o^2 = \left( \frac{1-(n_o+n_s)}{1+(n_o+n_s)} \right)^2 E_o^2, \quad (1)$$

where $(E_o)^2$ is the intensity of incident beam 704, $n_o$ is the refractive index of the underlying semiconductor material (usually silicon), and $n_s=\beta N_s$ is the change in refractive index of the semiconductor material due to its background doping concentration $N_s$. $\beta$ is a constant dependent on material properties and the wavelength of the measuring beam, which will be elaborated shortly.

On the other hand, in the doped region, the optical reflection consists of an interference between two reflection components; one component 706 (FIG. 7B) comes from the front surface F of the wafer. The other component can be either (1) component 708 which comes from interface 703 (between doped layer 702 and the underlying region 701) or (2) component 709 which comes from every location throughout doped layer 702 having doping concentration gradient.

FIG. 7B illustrates the reflection process in detail. For the moment, reflection component 709 is ignored; it will be incorporated into the analysis later on. When incident beam 704 encounters the surface F of the sample, part of it is reflected as beam component 706, and part of it is transmitted into doped layer 702 as beam 707. Beam 707 is reflected from interface 703 and passes through front surface F to emerge as reflected beam component 708.

Beam reflected components 706 and 708 interfere to form a single reflected beam with an intensity given by:

$$E_d^2 = |r_{sd} + t^2 r_j e^{-i2k(n_o+n_d)z_j}|^2 E_o^2 \quad (2)$$

where:

$$r_{sd} = \frac{1-[n_o+n_d]}{1+[n_o+n_d]} \quad (3)$$

$$r_j = \frac{[n_o+n_d]-n_o}{[n_o+n_d]+n_o} \quad (4)$$

$$t^2 = \frac{4n_o}{(1+n_o)^2} \quad (5)$$

$$n_d = \beta N \quad (6)$$

$$\beta = \frac{-e^2}{2m^*\omega^2 n_o \varepsilon_o} \quad (7)$$

$$\omega = kc \quad (8)$$

$$k = \frac{2\pi}{\lambda_o}, \quad (9)$$

N and $z_j$ are the doping concentration and thickness (junction depth) of the doped layer, respectively, e is the electron charge, $m^*$ is the carrier effective mass in the semiconductor material, $\varepsilon_o$ is the permittivity of free space, c is the speed of light in vacuum, and $\lambda_o$ is the wavelength of the measuring beam. The amplitude of reflection from the surface of the doped region (reflected component 706) is $r_{sd}$; if there is no doping, then $n_d=n_s$, and $r_{sd}$ becomes the amplitude of reflection from the undoped region (beam portion 705). The amplitude of reflection from the junction (component 708) is $r_j$.

Both the front surface reflection component 706 and the interface reflection component 708 from the doped region, as detailed in equations (2)–(9), contain information about the properties of the doped layer, since the free carriers contributed by the dopant atoms after annealing modify the refractive index of the semiconductor material. The surface reflection component 706 contains information about the peak doping concentration, while the interface reflection component 708 contains additional information about profile depth and abruptness of the profile. Therefore, in several embodiments, by comparing the reflectivity of the doped and undoped region, the aforementioned properties of the doped region are measured. In practice however, even with the refractive index change due to doping, the reflectivity difference between the doped and undoped areas is actually very small, only one part in $10^4$–$10^6$, depending on the doping concentration. Phase-sensitive synchronous detection is employed to enhance the difference in reflectivity; this topic will be discussed below in detail.

In order to understand how doping properties are extracted from the measurements, it is necessary to elaborate on the physics beyond equations (1)–(9). In the most general case, the doping concentration N depends on depth (z), as in the case of implanted and annealed wafers. As a result, the change in the refractive index of the doped layer arising from the added doping ($n_d$) also depends on depth. Equations (3) and (4) need to be modified slightly to reflect this dependency:

$$r_{sd} = \frac{1-[n_o+n_d(z=0)]}{1+[n_o+n_d(z=0)]} \quad (10)$$

-continued $$r_j = \frac{n_d(z) - n_d(z+dz)}{n_d(z) + n_d(z+dz)}. \quad (11)$$

The optical reflection from the doped layer is now distributed throughout the doping profile, at any depth where the refractive index changes, as represented by component 709 in FIG. 7B. All of the minute reflections interfere with one another and with the surface reflection to form a single returning beam. When equations (5)–(11) are substituted into equation (2), it can be shown that the reflected beam intensity from the doped layer has the form:

$$E_d^2 = r_{sd}^2 E_o^2 + \frac{|\beta| r_{sd} t^2 E_o^2}{n_o} \int_0^\infty \mathrm{Cos}(2kn_o z) \frac{dN}{dz} dz. \quad (12)$$

Analytical evaluation of the integral in equation (12) in some embodiments of the invention is based on an approximation for the doping distribution N(z). FIG. 8A depicts a simplified profile 801 of doping concentration as a function of depth (z). The graph in FIG. 8A models adequately real doping profiles in production wafers, following ion-implantation and thermal-annealing process. As shown in FIG. 8A, the doping concentration is constant and maximum near the surface ($N_d$), and then it gradually drops to the background doping concentration $N_s$. In most embodiments, processes used to form background doping concentration $N_s$ are well controlled using any prior art method, and therefore, the value of $N_s$ is known. The slope of the doping concentration profile 801 is commonly referred to as the abruptness of the profile, and it is an important property of a semiconductor wafer, in addition to the peak concentration $N_d$ and the profile depth $z_j$.

The profile depth $z_j$ is defined as the distance from the front surface F to a location in the interface 703 (FIG. 7B) where the concentration has dropped to a level halfway between $N_d$ and $N_s$ (FIG. 8A); whereas the profile abruptness is defined as the slope $(N_d - N_s)/2a$ (see the slanted portion of profile 801 in FIG. 8A). FIG. 8B shows the derivative of this simplified doping profile 801. As seen in FIG. 8B, the slope is zero everywhere except in the range 2a centered around profile depth $z_j$. A sharp concentration step at the surface (z=0) is not included in FIG. 8B because that step has been taken into account in the description for $r_{sd}$ in equation (10), resulting in the leading term in equation (12).

The signal of interest is the change in amplitude between reflected signals from the doped and the undoped regions. Subtracting equation (1) from equation (12), with the use of the simplified doping profile 801 in FIG. 8A, it can be shown that the signal takes on the form:

$$\text{Samplitude} = A \frac{4|\beta|(1-n_o)E_o^2}{(1+n_o)^3}(N_d - N_s)\left[1 - \frac{\mathrm{Sin}(2kn_o a)}{2kn_o a}\mathrm{Cos}(2kn_o z_j)\right] \quad (13)$$

where A is a wavelength dependent coefficient representing transmission loss through optical components, photodetector conversion efficiency, and amplifier gain factor. Equation (13) indicates that the measurement of Samplitude is dependent on three properties of the doping profile, namely the profile depth $z_j$, the maximum or peak doping concentration $N_d$, and a, which is a property associated with profile abruptness. Note that Equation (13) includes the interference effects of reflected components 706, 708 and 709 (FIG. 7B).

Figure 9A:
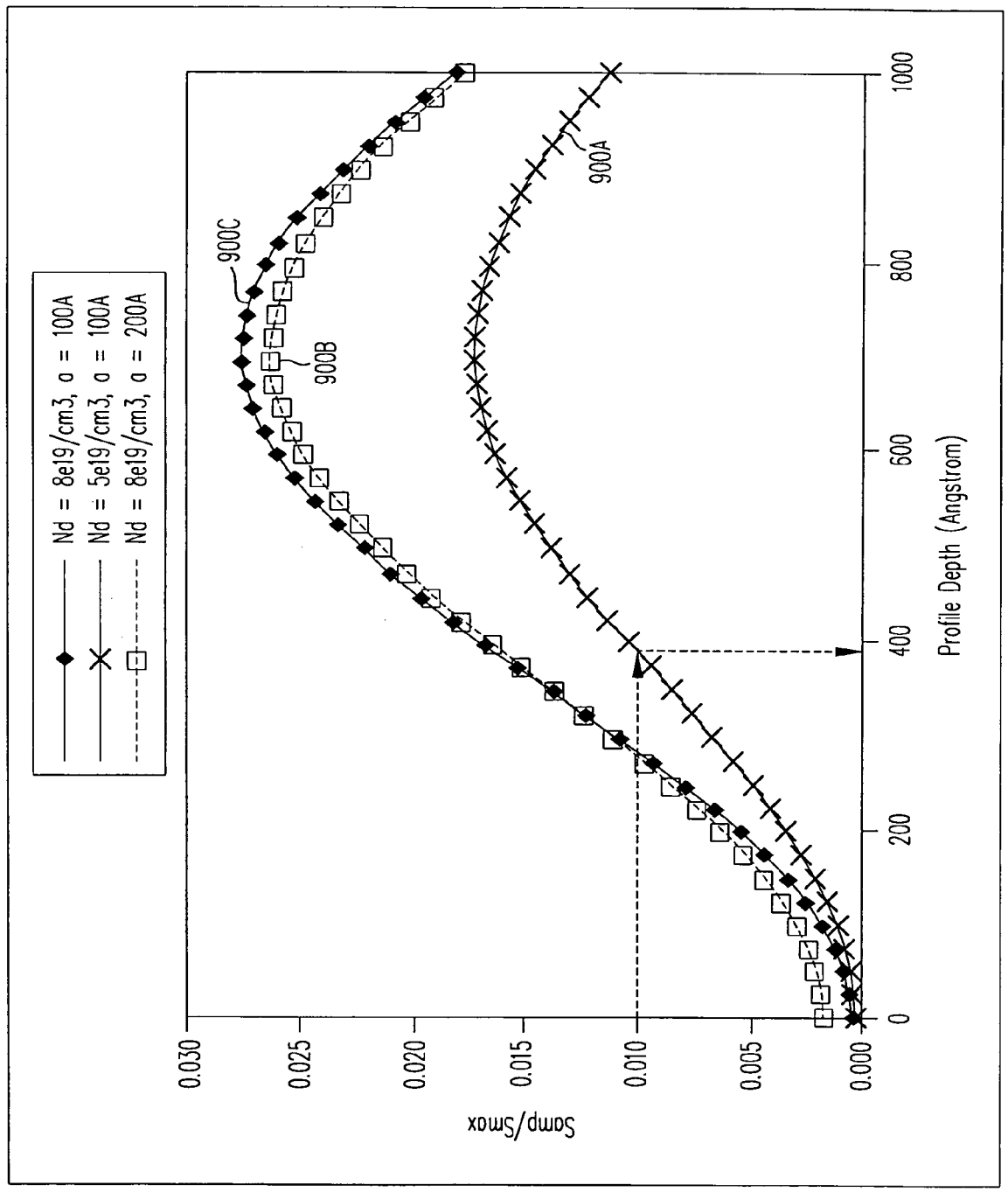
FIG. 9A shows, in theory, the reflected signal's intensity (along the y axis) as a function of depth of a doping profile for a silicon substrate material (along the x axis), when using a laser of wavelength of 980 nm for the measurement, and for peak doping concentration and profile abruptness combinations of $8e19/cm^3$ and 100 Å (for graph 900C), $5e19/cm^3$ and 100 Å (for graph 900A), and $8e19/cm^3$ and 200 Å (for graph 900B).

FIG. 9A shows the measurement of Samplitude (normalized by dividing it with Smax, wherein Smax is the maximum signal value as shown in FIG. 2I) plotted along the y-axis as a function of profile depth for a silicon substrate material plotted along the x-axis, when probed using a beam of wavelength 980 nm. Specifically, three graphs 900A–900C are plotted in FIG. 9A for three combinations of the peak doping concentration $N_d$ and the abruptness property a (see legend at the top of FIG. 9A). The abruptness property a is defined in FIG. 8A as being one half of the distance around profile depth $z_j$ wherein the doping concentration $N_d$ changes in substantially linear manner as a function of depth. The peak doping concentration primarily modifies the amplitude of the cosine curve, while the abruptness property modifies both the amplitude and the offset. However, as clearly evident from FIG. 9A, the effect of the profile abruptness is quite small (as compared to the effect of a change in dopant concentration).

A relationship between signal measurement (i.e. Samplitude) and profile depth, such as shown in FIG. 9A, is called a correlation curve, since it can be used to convert measured signals from unknown samples to their respective profile depths, provided that the other two properties $N_d$ and a are known. For example, as illustrated by the dashed arrows in FIG. 9A, for $N_d$=5e19/cm$^3$ and a=100 Å (see curve 900A) a measured signal of 0.01 (which represents a very small fraction of the incident beam intensity) corresponds to a profile depth of 393 Å for the unknown sample.

Although another depth of around 1000 Å could also be the result, normally the smaller depth is the correct answer because in most embodiments the implant process does not generate implants of the large depth 1000 Å, because the wafer is undergoing formation of Ultra Shallow (US) junctions. Normally, in process control embodiments this ambiguity is not an issue because initially the wafer fabrication process starts with fabrication of wafers having the smaller implant depth, and any deviations therefrom are measured (and corrected as appropriate). As an alternative to using equation (13), the correlation curve can be constructed using a set of samples, called calibration or reference samples, having known doping profiles. The doping profiles are characterized using an independent method such as SIMS or spreading resistance measurement.

In embodiments wherein all three doping properties $z_j$, $N_d$, and a are unknown, multiple measuring wavelengths are utilized. The coefficients A, β and k in equation (13) change with wavelength (see equations (7)–(9)), and therefore the signal is also a function of wavelength. With at least three wavelengths, three signal measurements are made, and equation (13) is solved simultaneously for the three properties $z_j$, $N_d$, and a. The background doping concentration $N_s$ must be known; it is usually readily available from the specifications of the starting wafer material. In several implementations, the coefficient A is also known for all the wavelengths that are utilized.

Three wavelengths require three A coefficients, and they are obtained from a calibration procedure using a single calibration sample. One patterned wafer is prepared with known active doping concentration ($N_d$), profile depth ($z_j$) and abruptness property (a). These properties are collected from a combination of SIMS analysis and sheet resistivity measurement. The calibration wafer is measured successively using each of the three selected wavelengths of the probing beam. For each wavelength, the coefficient A is calculated using equation (13).

Alternatively, if a calibration wafer is not available, the undoped area with known background doping concentration $N_s$ are used to calibrate the A coefficients. In this case, the signal from the undoped area is a DC signal given by:

$$S_{undoped} = A_{DC} \left( \frac{1 - n_o + |\beta|N_s)}{1 + n_o - |\beta|N_s)} \right)^2 E_o^2, \quad (14)$$

which is derived from equation (1). The coefficient $A_{DC}$ may be different from the A coefficient in equation (13) due to the difference in amplifier gain between the AC and the DC signals. However, if the ratio in amplifier gains is known beforehand, from knowledge of the amplifier circuits, A is calculated from $A_{DC}$, since the optical transmission loss and the photodetector conversion efficiency factors are the same. The calibration proceeds in the same way as with a calibration sample, the undoped area is measured successively using each of the three selected wavelengths, and for each wavelength, the coefficient $A_{DC}$ is calculated using equation (14).

Figure 9B:
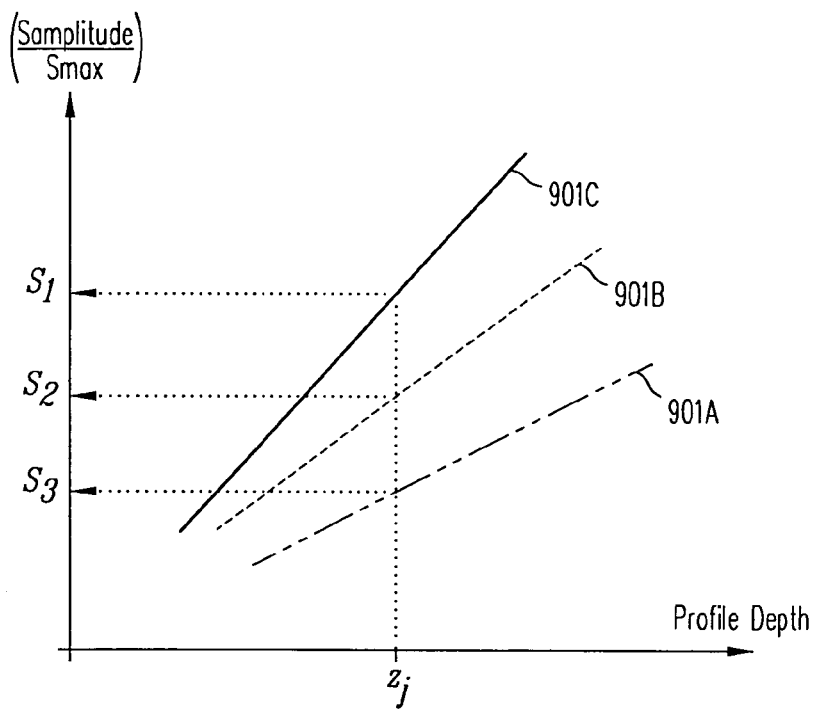
FIG. 9B illustrates use of three signals $S_1$, $S_2$, and $S_3$ measured from an unknown sample having a profile depth $z_j$, using three different wavelength laser beams. Curves 901, 902, and 903 are linear portions of a cosine response curve of the type shown in FIG. 9A, in the order of decreasing wavelength.

Once all the coefficients in equation (13) are determined, the measurement of the doping properties of an unknown wafer proceeds by sequential probing of a test structure containing the doped region at three pre-selected wavelengths. Three values of Samplitude are measured as signals $S_1$, $S_2$, and $S_3$ at the three wavelengths. As depicted in FIG. 9B, linear portions 901A, 901B, and 901C of the cosine response curve corresponding to the three wavelengths indicate the values $S_1$, $S_2$, and $S_3$ that are measured for a given (unknown) set of profile depth ($z_j$), peak doping concentration ($N_d$), and profile abruptness (a). Note that a linear portion 901A is present in the corresponding graph 900A (FIG. 9A) between signal values of approximately 0.003 to 0.012. In FIG. 9B, only the signal dependence on $z_j$ is shown, for the sake of simplicity, but it should be understood that the set of curves 901A, 901B, and 901C belongs to a particular combination of doping concentration $N_d$ and abruptness a. Other combinations of $N_d$ and a will result in a different set of curves 901A, 901B, and 901C. Substituting signals $S_1$, $S_2$, and $S_3$ into equation (13) produces three simultaneous nonlinear equations which are solved in the normal manner (e.g. by numerical analysis) to obtain values for profile depth ($z_j$), peak doping concentration ($N_d$), and profile abruptness (a).

Figure 9C:
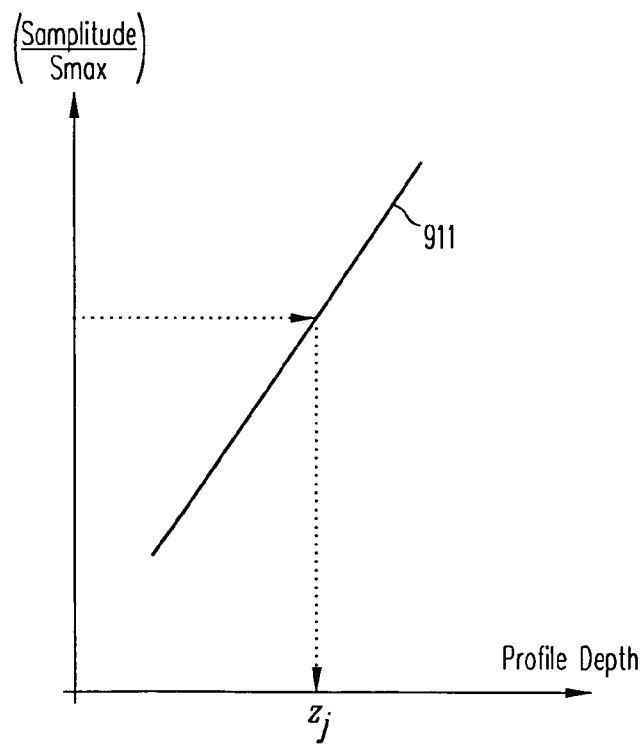
FIG. 9C illustrates use of a single signal to determine a profile depth $z_j$, from a linear portion of a response curve of the type shown in FIG. 9B.

Note that instead of solving such equations, in certain alternative embodiments data on the behavior of Samplitude as a function of profile depth are collected ahead of time prior to evaluation of a production wafer. Specifically, the above-described method of oscillating a beam source and detector is performed on doped and undoped regions on a number of reference wafers to obtain the values (Samplitude/Smax) for a corresponding number of different profile depths $z_j$. A plot of the graph from such measurements is illustrated in FIG. 9C. Note that the measurements that are plotted in FIG. 9C are for a given set of all other properties and measurement conditions, including a given wavelength of the probe beam.

Thereafter, during wafer fabrication, an Samplitude measurement on a production wafer (generated by oscillating the beam source and detector) is used to look up the profile depth, and if the resulting profile depth falls outside a predetermined range, then an appropriate change is made in a fabrication process. In one such embodiment, a pre-anneal measurement is made to determine the dosage, and only wafers that are within predetermined tolerance limits are further processed. During anneal, the profile depth and profile abruptness are both changed, although the impact on profile depth is larger than the impact on profile abruptness. Therefore, assuming that profile abruptness has not changed, any change in the measured Samplitude is treated as indicating a corresponding change in profile depth. Note that instead of monitoring profile depths $z_j$ at a given set of peak doping concentration $N_d$, and profile abruptness a, it is also possible to monitor either the concentration $N_d$ or the abruptness a at a given set of values of the other two properties.

In another alternative embodiment, the look-up table approach is utilized to monitor variations in any of the three properties $z_j$, $N_d$, and a, without knowing beforehand which property is changing. A set of reference samples with known variations in all three properties $z_j$, $N_d$, and a, clustered around a center (nominal) process condition, are measured using three laser wavelengths to construct the look-up table. The data from the look-up table can be plotted, and if all three properties are used, the resulting plot is a 4-dimensional surface for the signal for each wavelength.

Figure 9D:
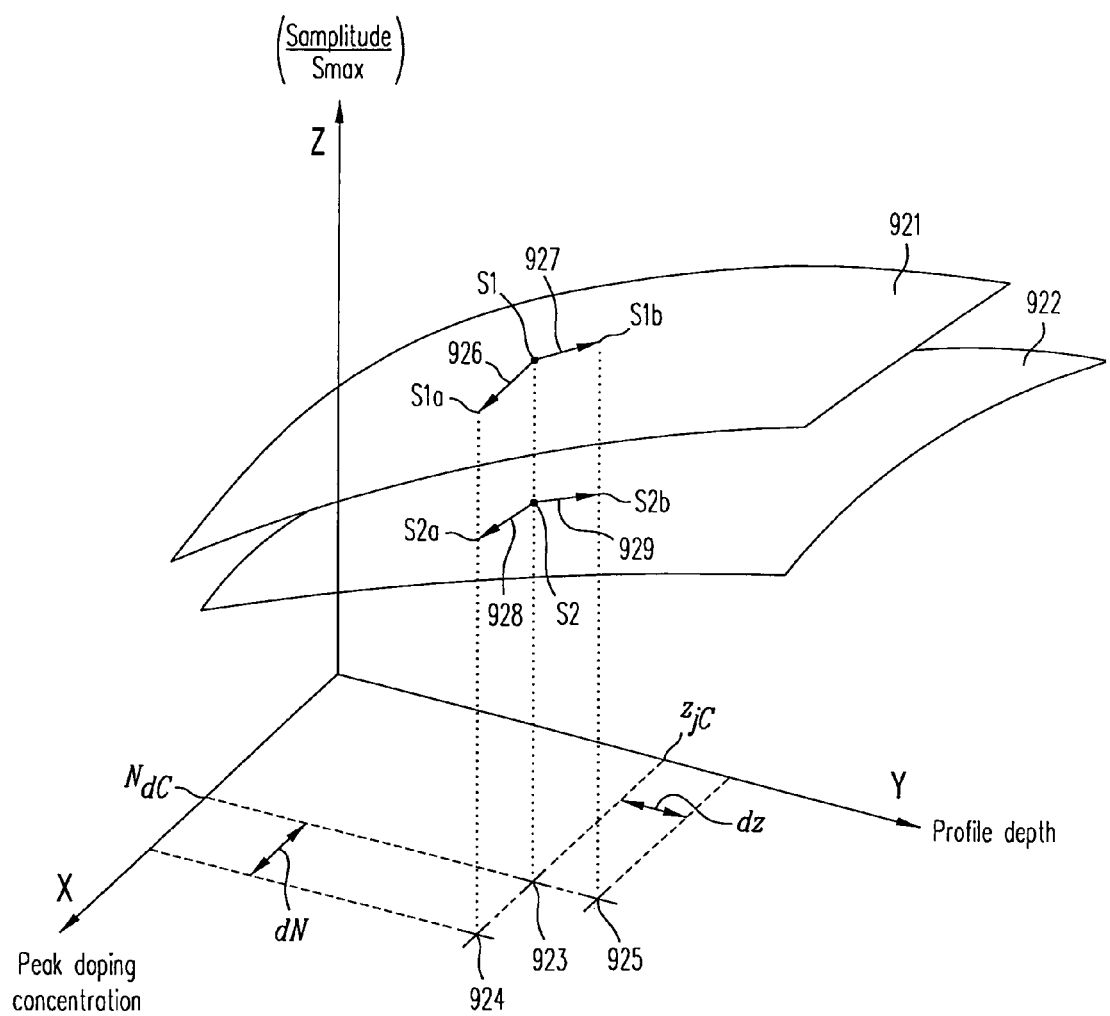
FIG. 9D illustrates, in a three dimensional graph, signal ratio (Samplitude/Smax) plotted on the Z-axis, as a function of the peak doping concentration and the profile depth on the X and Y-axes, respectively, wherein measurements using two different wavelengths of the measuring beam are shown as two surfaces 921 and 922.

For simplicity in illustrating the method of this embodiment, only two properties $z_j$ and $N_d$ are considered next, which generate a 3D surface when plotted. FIG. 9D shows portions of such 3D surfaces for two different wavelengths of the measuring beam (since two properties only requires two wavelength measurements). In FIG. 9D, the signal ratio (Samplitude/Smax) is plotted on the Z-axis, as a function of the peak doping concentration and the profile depth on the X and Y-axes, respectively. Surfaces 921 and 922 are constructed from measuring a given set of reference samples using illumination of two respective wavelengths $\lambda 1$ and $\lambda 2$, where $\lambda 1$ is larger than $\lambda 2$.

The one reference sample with the nominal process condition is represented as cross 923 on the XY-plane in FIG. 9D, with concentration $N_{dC}$ and profile depth $z_{jC}$. This nominal reference sample produces signals S1 and S2 on surfaces 921 and 922 respectively. When there is a slight variation in the fabrication process producing for example a slight change in doping concentration by an amount dN, the process condition moves from cross 923 to cross 924 on the XY-plane. As a result, the signals shift from S1 and S2 to a new pair of signals S1a and S2b on surfaces 921 and 922, as indicated by arrows 926 and 928 respectively. Similarly, a slight change in profile depth by an amount dz moves the process condition from cross 923 to cross 925 on the XY plane, resulting in signal shifts from S1 and S2 to a new pair of signals S1b and S2b on surfaces 921 and 922, as indicated by arrows 927 and 929, respectively.

In a typical wafer fabrication process, it may not always be possible to predict which property deviates from the nominal process condition. Several embodiments of the type described herein monitor signal deviations from nominal, and identify the process parameter that causes the signal shift, provided that only one property is changing at any given time. Referring to FIG. 9D, a change in doping concentration dN shifts the nominal signals S1 and S2 to S1a and S2a at the two wavelengths $\lambda 1$ and $\lambda 2$, respectively. Similarly, a change in profile depth dz shifts the signals S1 and S2 to S1b and S2b. The signal difference at the two wavelengths are (S1a–S1) and (S2a–S2) for the doping concentration shift, and (S1b–S1) and (S2b–S2) for the profile depth shift. The ratio of the difference signal at the two wavelengths, (S1a–S1)/(S2a–S2) or (S1b–S1)/(S2b–S2), identifies the process parameter and/or property of the wafer that is causing the shift, e.g. as discussed below. The look-up table, constructed by the measurements on a set of reference samples, contains the information on the size of the signal difference ratio that can be expected to enable the identification process.

Figure 9E:
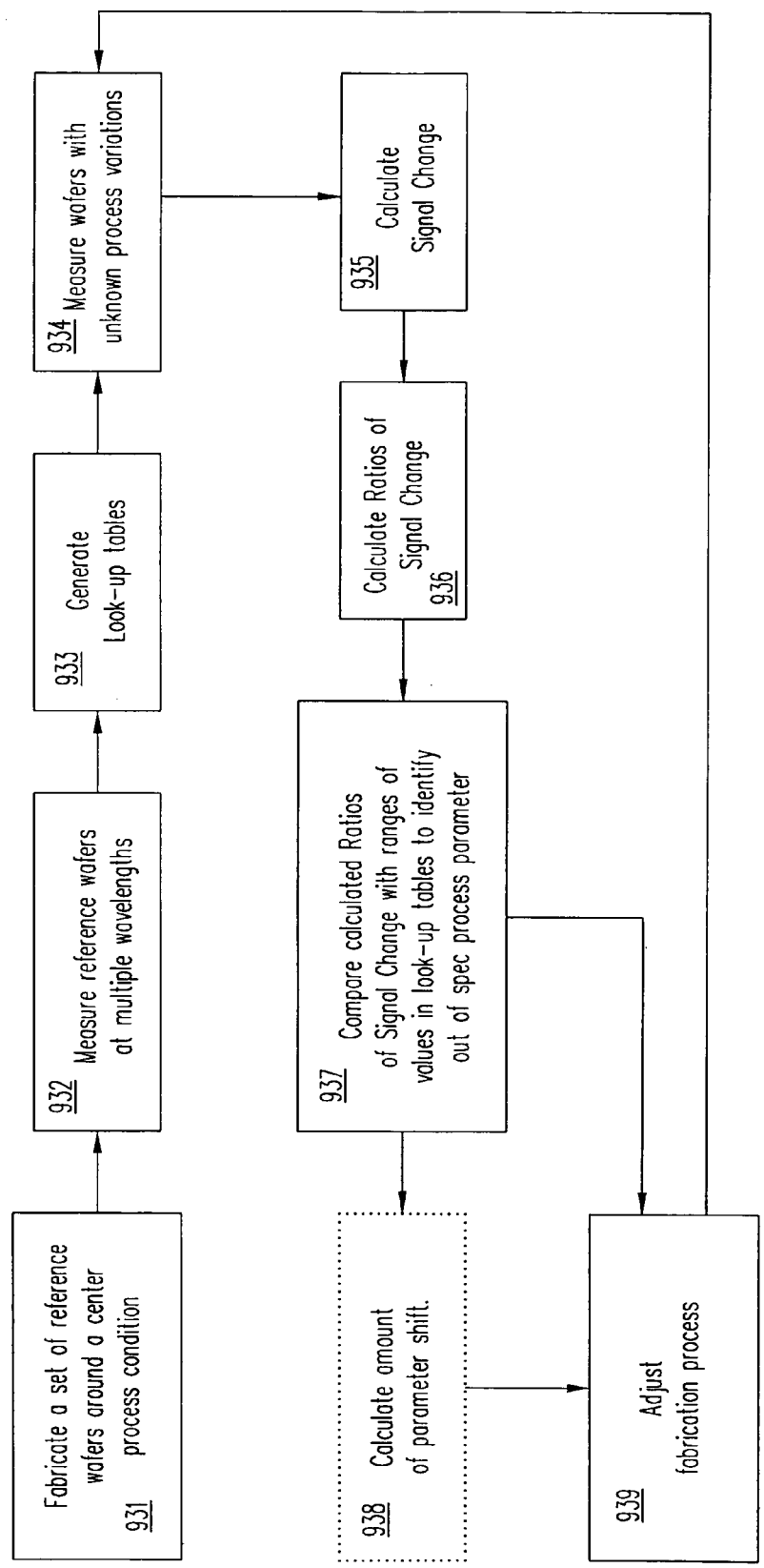
FIG. 9E illustrates, in a flow chart, acts performed in some embodiments of the invention.

FIG. 9E further illustrates a step-by-step procedure that is used in some embodiments to implement process monitoring described in the previous paragraphs. Once again for simplicity, only two properties zj and Nd are considered in the following description. Specifically, a set of reference wafers are fabricated with known variations in zj and Nd, clustered around a center (nominal) process condition, as illustrated in act 931 of FIG. 9E. The reference wafers are then measured at multiple wavelengths, in this case 2 wavelengths (see act 932 in FIG. 9E). A set of look-up tables is then generated, as indicated by act 933 of FIG. 9E. Examples of such look-up tables are shown in Tables 1 and 2 below, for measurements at 670 nm and 980 nm wavelengths.

TABLE 1

Look-up table generated by a set of reference samples with variations in profile depth $z_j$.

| | Signal | | Change in Signal | | Ratio of Signal |
|---|---|---|---|---|---|
| zj (Å) | at 670 nm | at 980 nm | at 670 nm | at 980 nm | Change |
| 230 | 138.4 | 173.0 | −17.7 | −27.2 | 0.65 |
| 240 | 147.3 | 186.5 | −8.8 | −13.8 | 0.64 |
| 250 | 156.1 | 200.2 | 0.0 | 0.0 | — |
| 260 | 164.7 | 214.3 | 8.7 | 14.1 | 0.62 |
| 270 | 173.2 | 228.6 | 17.1 | 28.4 | 0.60 |

TABLE 2

Look-up table generated by a set of reference samples with variations in peak doping concentration $N_d$.

| Nd | Signal | | Change in Signal | | Ratio of Signal |
|---|---|---|---|---|---|
| (atoms/cm$^3$) | at 670 nm | at 980 nm | at 670 nm | at 980 nm | Change |
| 9.0 × 10$^{19}$ | 140.4 | 180.2 | −15.6 | −20.0 | 0.78 |
| 9.5 × 10$^{19}$ | 148.3 | 190.2 | −7.8 | −10.0 | 0.78 |
| 1.0 × 10$^{20}$ | 156.1 | 200.2 | 0.0 | 0.0 | — |
| 1.05 × 10$^{20}$ | 163.9 | 210.2 | 7.8 | 10.0 | 0.78 |
| 1.10 × 10$^{20}$ | 171.7 | 220.3 | 15.6 | 20.0 | 0.78 |

In this particular example, the center process condition is given by a profile depth zj=250 Å, and a peak doping concentration Nd=1.0×1020 atoms/cm3. In the look-up tables, the "Change in Signal" columns refer to the signal difference as a result of a property shift from the nominal condition. For example, in Table 1, the reference wafer with zj=270 Å gives a signal of 173.2 at 670 nm, which represents a signal change of 17.1 relative to the signal at the nominal depth of 250 Å (173.2−156.1=17.1). The "Ratio of Signal Change" in the look-up table refers to the difference signal at 670 nm divided by the difference signal at 980 nm. For example, in Table 1, measurements on the reference wafer with zj=270 Å yield Changes in Signal of 17.1 and 28.4 at 670 nm and 980 nm wavelengths, respectively, resulting in a Ratio of Signal Change of 0.6 (17.1/28.4=0.6).

As Tables 1 and 2 indicate, a small shift (within +/−10% of the nominal value) in zj results in a Ratio of Signal Change in the range of 0.6–0.65 shown in Table 1, depending on the exact amount of the shift. However, a small shift in Nd results in a fixed Ratio of Signal Change of 0.78 in Table 2, although this ratio could be changing and different in Table 2, depending on a number of factors such as signal noise, calibration, and resolution of measurements. Comparison of a Ratio of Signal Change of an unknown wafer to see if it falls within a range in Table 1 or if it falls within a range in Table 2 enables the identification of the respective property (either zj or Nd) that causes the signal shift, as discussed in detail next.

Specifically, during normal fabrication of wafers (also called "production wafers"), variations in their properties (and corresponding variations in process control parameters) are determined by measuring signals (of the type described herein) using probe beams at the same two wavelengths as in the reference wafer measurements (see act 934 in FIG. 9E). Next, the change in measured signals for the production wafers are then calculated (see act 935 in FIG. 9E), followed by taking a ratio of the signal changes at the two wavelengths (see act 936 in FIG. 9E). An example of the result of such measurement and calculation is shown in Table 3 for five production wafers with various parameter/property shifts. Comparing the calculated Ratios of Signal Change with the value ranges in the two look-up tables (Tables 1 and 2) identifies the property and/or process parameter that deviates from nominal (see act 937 in FIG. 9E), the result of which is shown in the last column of Table 3.

TABLE 3

Measurement results of five production wafers with identification of the property that has changed based on the ratio of signal change.

| | Signal | | Change in Signal | | Ratio of Signal | Property causing |
|---|---|---|---|---|---|---|
| Wafer # | at 670 nm | at 980 nm | at 670 nm | at 980 nm | Change | signal shift |
| 1 | 142.8 | 179.7 | −13.2 | −20.5 | 0.64 | zj |
| 2 | 165.4 | 212.2 | 9.4 | 12.0 | 0.78 | Nd |
| 3 | 166.4 | 217.1 | 10.4 | 16.9 | 0.61 | zj |
| 4 | 156.1 | 200.2 | 0.0 | 0.0 | — | none |
| 5 | 143.6 | 184.2 | −12.5 | −16.0 | 0.78 | Nd |

In addition to identifying a property that deviates from its nominal value, such a look-up table approach is also capable of estimating the amount of shift in the out of spec property by performing a data interpolation using the look-up table values (see act 938 in FIG. 9E). Using such a shift, an appropriate adjustment is made in the fabrication process (see act 939 in FIG. 9E). For example, a feed-back loop may be implemented by incrementally changing a process control parameter during fabrication of production wafers, and finding an incremental improvement in a corresponding property. Note that act 938 is not performed in some embodiments, i.e. the precise amount of change in a property of the wafer need not be determined in embodiments wherein act 939 is performed directly after act 937. For example, if the calculated ratios fall within a predetermined range of ratio values then a table of predetermined data (which is determined experimentally) may be used to identify the change to be made in one or more process control parameter(s).

For example, in Table 3, wafer #3 has signal values of 166.4 and 217.1 at 670 nm and 980 nm wavelengths, respectively. Comparing with Table 1, these signal values for wafer #3 fall between the signal values for reference wafers with profile depths of 260 Å and 270 Å. A simple interpolation procedure to estimate the profile depth of wafer #3 proceeds as follows:

$$z_j = 260 + \frac{(166.4 - 164.7)}{(173.2 - 164.7)}(270 - 260) = 262.02 \text{ Å}$$

for the 670 nm wavelength, and $$z_j = 260 + \frac{(217.1 - 214.3)}{(228.6 - 214.3)}(270 - 260) = 261.99 \text{ Å}$$

for the 980 nm wavelength. The estimated profile depth is therefore 262 Å, which represents a deviation of 12 Å from the nominal value of 250 Å.

If more than two process parameters are involved, the method as described above can be extended by using more than two wavelengths for the measurement, and considering all the possible combinations of the signal difference ratio (or Ratio of Signal Change). Specifically, if three different process parameters may change, then three measurements are made on each reference wafer (one with each of three probe beams of different wavelengths), and three different signal changes are computed, and then three different ratios are computed. Thereafter, during wafer fabrication, each production wafer is the subject of three measurements at the three wavelengths, and once again three different ratios are computed, and they are used to identify the process parameters that have changed (again by identifying whichever ratio falls within the range of ratios in a table). The measurements on each reference wafer may be made at sufficiently close intervals in the change of each process parameter, to generate a sufficiently large "cluster" of measurements centered around nominal values (of the process parameters) so as to ensure that a single process parameter change during fabrication of production wafers is easily identified by such tables.

Instead of using the values $S_1$, $S_2$, and $S_3$ directly for lookup, in some embodiments such values are used in any iterative numerical methods well known to those skilled in the art. Such methods may be used to solve three simultaneous equations for the three unknown variables $z_j$, $N_d$, and a. For example, FIG. 10A shows the screenshot of a commercial software, Mathcad 2001i Professional, which is programmed to solve the three simultaneous nonlinear equations. Block 1001 defines the equation that needs solving, i.e. equation (13), and its associated components. Some definitions for the constants are not shown in FIG. 1A, but they are defined elsewhere within the program.

Block 1002 specifies certain initial guess values for the unknown variables $N_d$, z, and a. Block 1003 is the "solve block", consisting of a set of constraints (block 1004), the solving function "Find" and the solutions (block 1005). Block 1004 forms the set of three simultaneous equations to be solved, with the values $5.019 \times 10^{-3}$, $4.404 \times 10^{-3}$, and $3.836 \times 10^{-3}$ corresponding to the signals $S_1$, $S_2$, and $S_3$, respectively. Block 1005 displays the solution to the unknown variables $N_d$, z, and a as $8.028 \times 10^{19}/\text{cm}^3$, 399 Å, and 102.7 Å, respectively, for this hypothetical unknown sample.

Full text of an example of the MathCAD program shown in FIG. 10A is provided as an illustration on the following page.

Physical Constants:
  Index of refraction of ambient: $n_{amb} := 1$
  Index of refraction of substrate: $n := 3.6$
  dielectric constant of free space (F/m): $\epsilon_0 := 8.854 \cdot 10^{-12}$
  dielectric constant of silicon: $\epsilon_s := 11.7$
  electron charge (coulomb): $q := 1.602 \cdot 10^{-19}$
  effective electron mass (kg): $m_e := 2.37 \cdot 10^{-31}$
  speed of light (cm/s): $c := 3 \cdot 10^{10}$ $$Ns := 3 \cdot 10^{18} \qquad k(\lambda) := 2 \cdot \frac{\pi}{\lambda} \qquad \omega(\lambda) := 2 \cdot \pi \cdot \frac{c}{(\lambda \cdot 10^{-8})}$$

$$\text{beta}(\lambda) := \frac{(-q^2 \cdot 10^6)}{2 \cdot [\epsilon_0 \cdot \sqrt{\epsilon_s} \cdot m_e \cdot (\omega(\lambda))^2]} \qquad \text{sinc}(a, \lambda) := \frac{\sin(2 \cdot k(\lambda) \cdot n \cdot a)}{2 \cdot k(\lambda) \cdot n \cdot a}$$

$$S(Nd, \lambda, z, a) := \left[4 \cdot \text{beta}(\lambda) \cdot \frac{(1-n)}{(1+n)^3}\right] \cdot$$

$$(Nd - Ns) \cdot (1 - \text{sinc}(a, \lambda) \cdot \cos(2 \cdot k(\lambda) \cdot n \cdot z))$$

$$Nd := 10^{20} \qquad z := 500 \qquad a := 50$$

Given $S(Nd, 6300, z, a) = 3.094 \cdot 10^{-3}$ $S(Nd, 6700, z, a) = 3.414 \cdot 10^{-3}$ $S(Nd, 7300, z, a) = 3.836 \cdot 10^{-3}$ $$\text{Find}(Nd, z, a) = \begin{pmatrix} 8.029 \times 10^{19} \\ 3.992 \times 10^2 \\ 1.037 \times 10^2 \end{pmatrix}$$

The hardware configuration for several embodiments of the type described above is shown in FIG. 10B. Measurement lasers 1201a, 1201b, and 1201c are semiconductor diode lasers with wavelengths that can range anywhere from 400 nm to 1100 nm. Typical values of the laser wavelength that may be used are 405 nm, 635 nm, 730 nm, 830 nm, and 980 nm. The maximum output power of the measurement lasers is around 100 mW. The output beams of the lasers 1201a, 1201b, and 1201c are collimated with collimating lenses 1202a, 1202b, and 1202c, providing collimated beam 1203. Only one of the three lasers is operated at any given time. Not shown is a mechanical shutter in front of each of the lasers to block the beams when they are not in use.

A dichroic mirror 1210 (such as a partially transmissive mirror, e.g. part number 1918-b available from Dominar of Santa Clara, Calif.) is used with one of the lasers, to select a beam 1211 that is to be incident on a surface of the wafer. Specifically, dichroic mirror 1210 is mounted on a small movable platform, and moved to an appropriate location to select the wavelength of beam 1211. Beam 1211 then passes through 50:50 non-polarizing beam splitter 1212 (e.g. part number 10BC17 MB.2 from Newport Corp., Irvine, Calif.) which is also referred to as a "detection system beam splitter" and a 90:10 beam splitter 1213 which is also referred to as a "vision system beam splitter". An example of the vision system beam splitter 1213 is available from Precision Applied Products of Fullerton, Calif., by specifying 93.3% transmission at 0.83 microns wavelength and 90% transmission at 1.48 microns wavelength. Note that the specifications for the vision system beam splitter 1213 are selected based on the wavelength of the probe beam to ensure that a majority of the power is transmitted therethrough.

Note that although a 90:10 beam splitter is used in some embodiments as being used as a vision system beam splitter, other embodiments may use beam splitters that split the beam in different ratios, such as 95:5 or 80:20. Moreover, although a 50:50 beam splitter is used in some embodiments as a detection system beam splitter, other embodiments may use beam splitters that split the beam in different ratios, such as 60:40.

The power transmitted through beam splitter 1213 thereafter reaches a beam deflector 1215 which may be, for example, an acousto-optic beam deflector or a galvanometer mirror as described elsewhere herein. An oscillating beam from deflector 1215 then passes through an objective lens 1216 (such as a 100×, 0.8 NA lens made by Olympus of Tokyo Japan), and is thereafter incident on wafer 1217. Deflector 1215 receives a modulation signal from lock-in amplifier 1231 via connection 1235, which causes beam 1211 to be deflected slightly in a periodic manner about the propagation axis. The periodic deflection of beam 1211 by deflector 1215 causes beam 1211 to scan along a line on wafer 1217. Lens 1216 focuses beam 1211 onto the surface of wafer 1217, which is mounted on a stage 1218. With proper alignment, beam 1211 scans across doped and undoped regions of a test structure of interest.

The portion of beam 1211 which is specularly reflected (in the direction of incidence which is normal) from wafer 1217 is recollimated by lens 1216. Beam splitter 1213 diverts 10% of the reflected beam to lens 1226 and camera 1227, which provide a system to align the beam spot on a surface of wafer 1217 to the test structure of interest. Not shown is an autofocus system that consists of a pinhole and a detector, which also uses the portion of the reflected beam diverted by beam splitter 1213. In one embodiment, an example of lens 1226 is tube lens 81845 available from—Nikon of Tokyo, Japan, and an example of camera 1227 is a CCD camera, e.g. model 85400 available from FJW Industries of Palatine, Ill. The signal provided by camera 1227 is fed (in one embodiment) into a vision system such as model ASP-60CR-11-S available from Cognex Corporation, Boston, Mass.

At least a portion of the reflected beam reaches a detector 1223, an example of which is a silicon photodiode (although a phototransistor is used in alternative embodiments). In one embodiment, detector 1223 is a photocell (such as a silicon photodiode, e.g. PIN-44DP from UDT Sensors, Inc. of Hawthorne, Calif., USA) that converts the incident electromagnetic radiation into a current. The current from detector 1223 is converted to a voltage using transimpedance amplifier 1230, the output of which goes to lock-in amplifier 1231. Note that the signal from detector 1223 to lock-in amplifier 1231 is an analog continuous electrical signal. The output of lock-in amplifier 1231 goes to a digital computer 1232, which receives the signal and presents it (or a value derived therefrom as described herein) to the user or to other data collection systems. Lock-in amplifier 1231 includes a frequency reference that is used to modulate deflection of the beam by deflector 1215 via connection 1235. As noted above, the lock-in amplifier 1231 supplies to deflector 1215 a signal oscillating at a predetermined frequency that is generated by a reference oscillator included in the lock-in amplifier 1231.

In principle, embodiments of the type described herein can be extended to use more than three wavelengths to provide increased accuracy and/or to measure other properties. Additionally, for process monitoring purposes, measurement(s) of the type described above can be performed without any calibration to determine the actual value of a property. In several such applications, a reference signal value is initially obtained from a reference wafer having known good properties (e.g. formed by known process parameters). Monitoring of subsequently processed wafers in a production line utilizes a Statistical Process Control (SPC) chart, in a manner well known in the art, to track deviations from the reference signal. The signal deviations are directly related to actual process deviations, and one or more process limits are used in process control. Use of previously-identified process limit(s) results in manufacture of wafers within preset manufacturing tolerances.

Figure 10B:
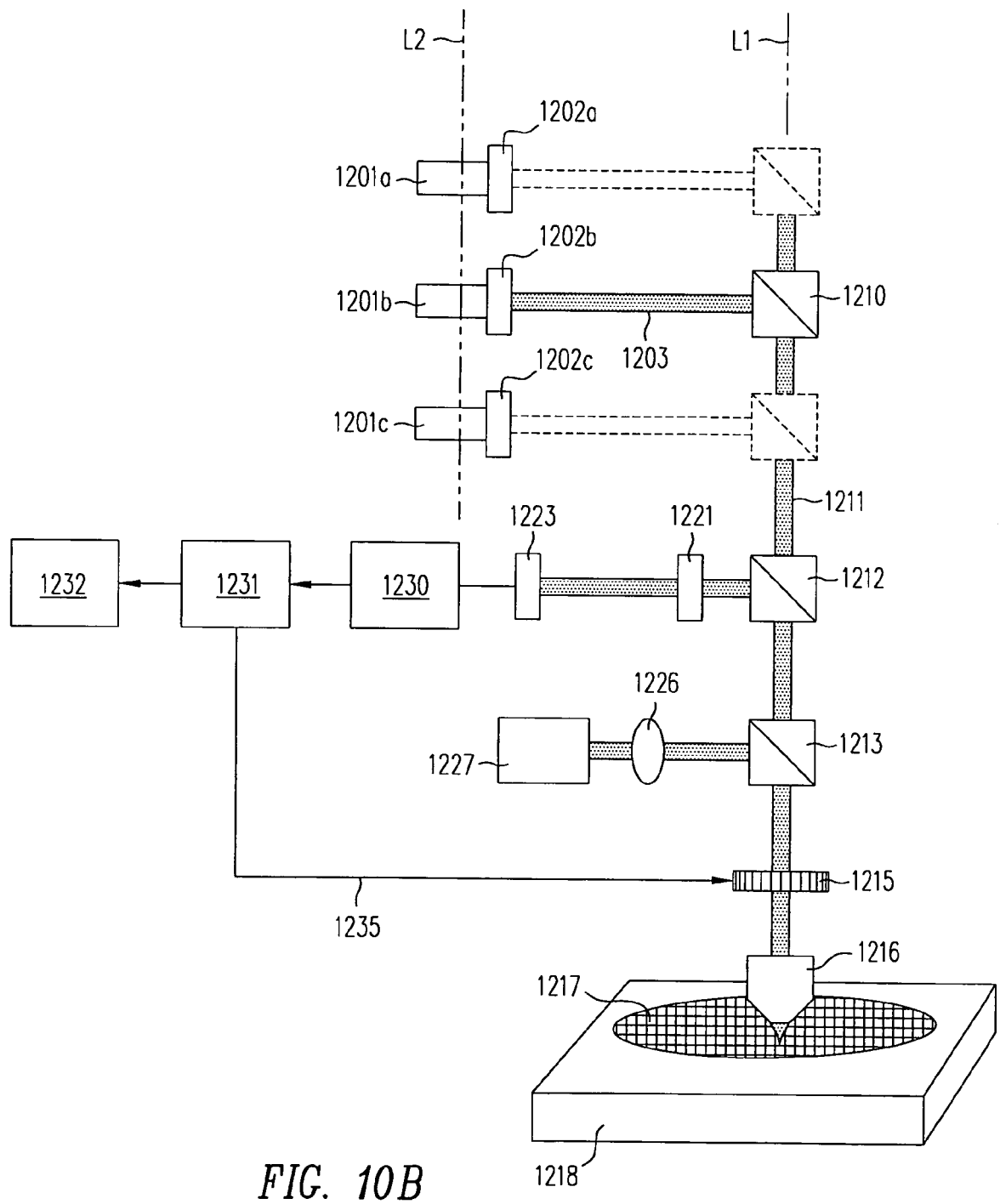
FIGS. 10B and 10C illustrate, in a block diagram, two alternative embodiments of a three laser apparatus for performing the measurements used in the program of FIG. 10A.
Figure 10C:
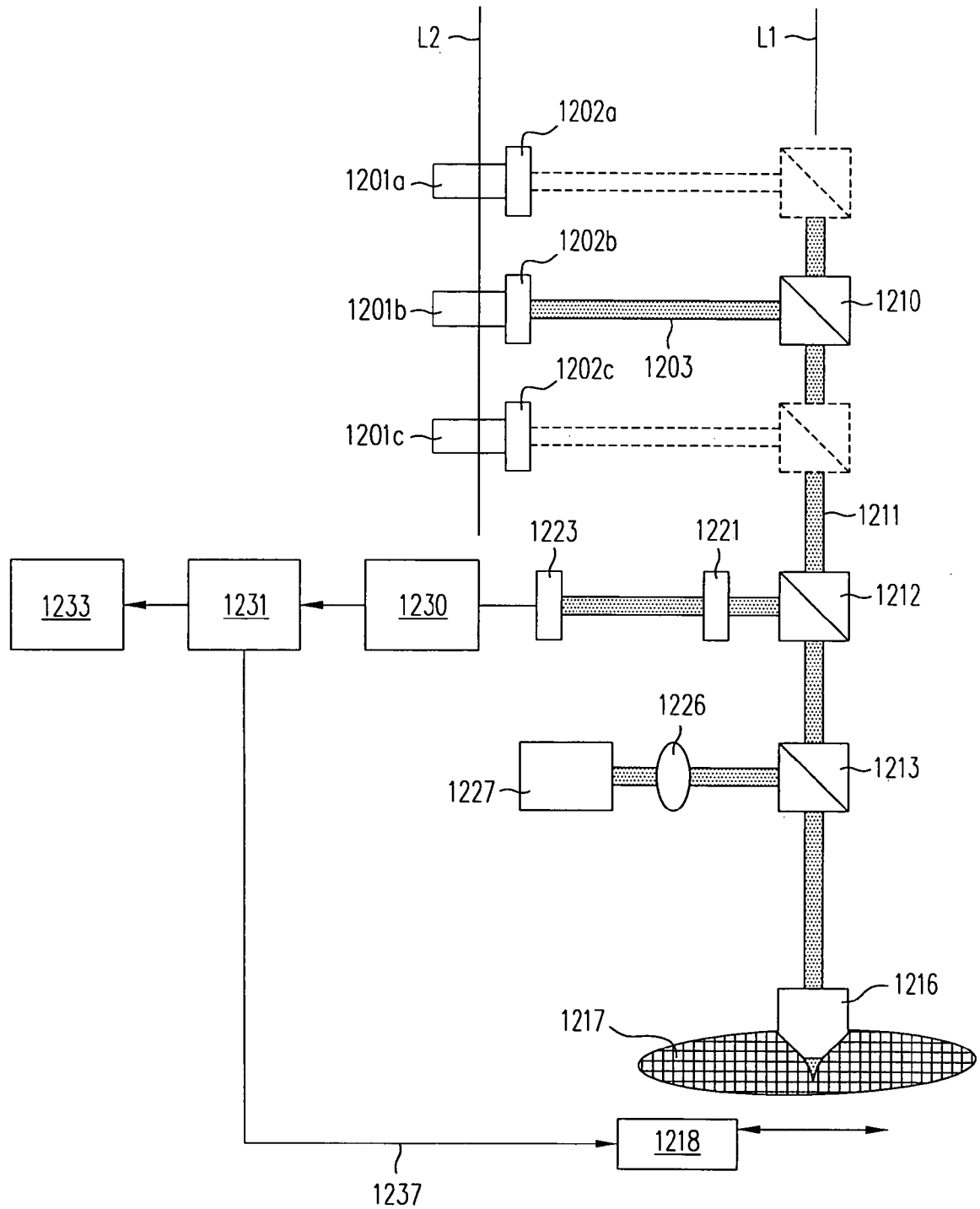

In an alternative embodiment illustrated in FIG. 10C, the apparatus is identical to the above-described apparatus illustrated in FIG. 10B except for the following difference. Specifically, deflector 1215 of FIG. 10B is not used in the apparatus of FIG. 10C. Instead, in the apparatus of FIG. 10C, stage 1218 is movable and is used to move wafer 1217 back and forth in a single direction at a fixed frequency. The signal to oscillate stage 1218 comes from lock-in amplifier 1231 via a connection 1237, as shown in FIG. 10C.

Figure 11A:
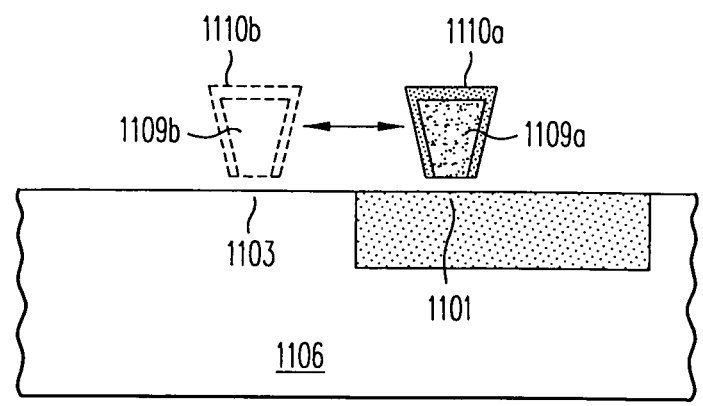
FIG. 11A illustrates in an alternate embodiment probing of doped region 1101 and undoped region 1103 of a test structure by a carrier generation beam 1110 collinear with a measuring beam 1109.
Figure 11B:
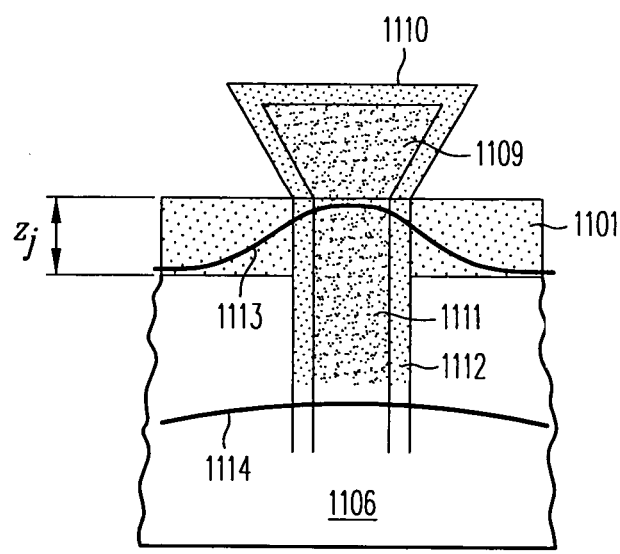
FIG. 11B illustrates generation of excess carrier distributions 1113 and 1114 by beam 1110 in the doped layer 1101 and well region 1106, respectively.

FIGS. 11A and 11B illustrate additional embodiment of this invention, that use two laser beams: a first laser beam 1109 is of the type described above (also called "probe beam"), and a second laser beam 1110 (also called "pump beam") has photon energy greater than the bandgap of the semiconductor material. The pump beam 1110 (FIG. 11B) is combined with the probe beam 1109 using a dichroic mirror (not shown in FIG. 11B) to form dual collinear beams. These two beams are thereafter moved together between doped region 1101 and undoped region 1103 of a test structure. The two beams are illustrated in FIG. 11A at positions 1109a and 1109b respectively at the end points of oscillation of the probe beam, and positions 1110a and 1110b respectively for the end points of oscillation of the pump beam.

Figure 11C:
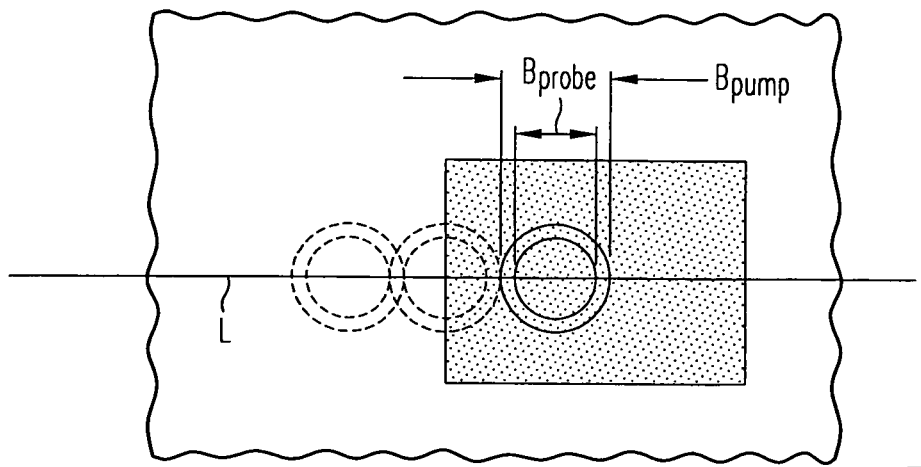
FIG. 11C illustrates, in a plan view, multiple positions of two concentric incident beams (one position shown solid and two other positions shown dotted) during oscillation along a straight line L between the doped region and the undoped region of a test structure.

As depicted in FIG. 11C, the pump beam has a slightly different (in this example slightly larger) spot size of diameter Bpump than the probe beam's diameter Bprobe. FIG. 11B illustrates in more detail the effect of using the pump beam 1109 in addition to the probe beam 1110. Portions of the incident probe beam 1109 and pump beam 1110 are transmitted into the doped layer 1101 (with thickness $z_j$) and the underlying well region 1106 as beams 1111 and 1112, respectively. The transmitted pump beam 1112 generates excess carrier distributions 1113 and 1114 inside the doped layer 1101 and the well region 1106, respectively. Due to the short carrier diffusion length inside the doped layer, the excess carrier distribution 1113 decays rapidly outside the diameter of the pump beam. Inside the well region, the carrier diffusion length is much larger, resulting in a nearly flat carrier distribution 1114. In other words, in the doped region 1101 of a test structure (see FIG. 11A), the excess carrier distribution is strongly influenced by the underlying doping profile.

On the other hand, in the undoped region 1103, the excess carrier distribution is constant with depth. The difference in reflectivity of the probe beam between two regions that are illuminated by the pump beam is now a measure of the difference in excess carrier distribution between the doped and undoped regions. Therefore, an analog electrical signal that is measured by a photodetector (based on reflectivity of the probe beam) is still related to the doping parameters such as profile depth and peak doping concentration. However, the signal may also be sensitive to other parameters such as oxide charge and defect densities. In other words, by using a carrier-generation beam (i.e. the pump beam), a reflectivity measurement of the probe beam is made more sensitive to other properties of the doped layer.

As indicated earlier, phase-sensitive detection of reflectivity of the probe beam (using a lock-in device) enhances a small difference in reflectivity between the doped and undoped regions. In such embodiments, the two beams together form a combined beam which is oscillated between the doped and undoped regions in a periodic manner at a fixed frequency. A reflection of the combined beam is filtered to pass only the probe beam reflected portion to a photodetector. An analog continuous electrical signal at the output of the photodetector is periodic, and is detected by a lock-in amplifier at the frequency of and in phase with oscillation of the combined beam. The amplitude of this electrical signal is proportional to the difference in reflectivity between the doped and undoped areas, and contains information on one or more properties of the doped layer.

The difference signal of interest has the exact same form as equation (13):

$$S_{amplitude} = A \frac{4|\beta|(1-n_o)E_o^2}{(1+n_o)^3}(N_{Cs} - N_{Cd})\left[1 - \frac{\text{Sin}(2kn_o a)}{2kn_o a}\text{Cos}(2kn_o z_j)\right], \quad (15)$$

except that the doping concentrations $N_d$ and $N_s$ in equation (13) are replaced by $N_{Cs}$ and $N_{Cd}$, which refer to the excess carrier concentrations at the undoped and doped regions, respectively.

Figure 12:
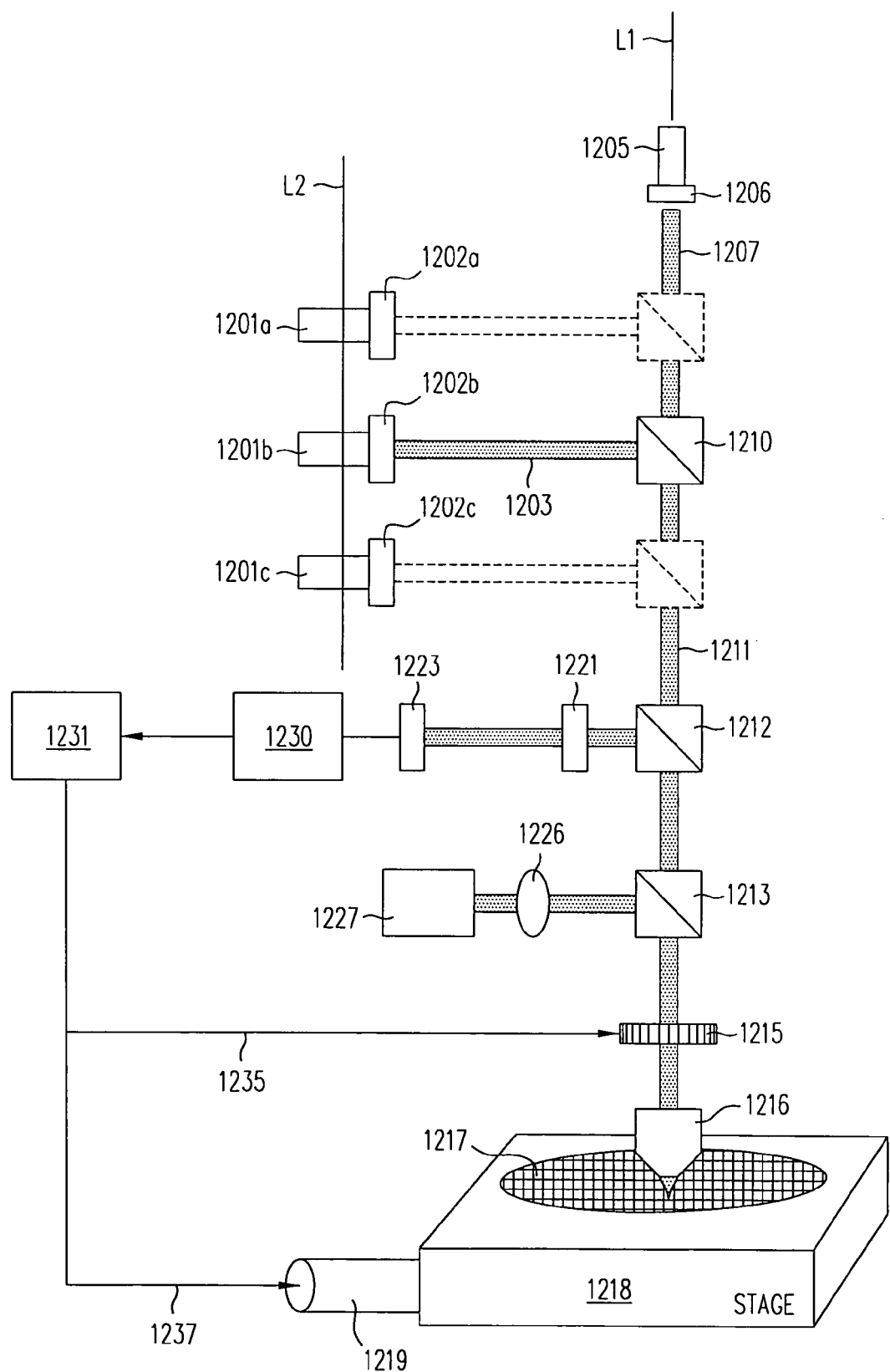
FIG. 12 shows the hardware configuration of some embodiments for evaluation of a test structure using either an oscillating stage (1218) or a beam deflector (1215) as the means for oscillating a spot along a straight line between two adjacent regions.

The hardware configuration for several embodiments of the type described above in reference to FIGS. 11A and 11B is shown in FIG. 12. The apparatus of FIG. 12 is similar to the above-described apparatuses of FIGS. 10B and 10C, except for certain differences which are discussed next. In addition to three measurement lasers 1201a, 1201b, and 1201c described above, the apparatus of FIG. 12 includes a fourth laser 1205. The fourth laser 1205 is used as a carrier generation laser, an example of which is a semiconductor diode laser operating at 830 nm wavelength. In this example, its maximum output power is 200 mW, to generate sufficient carrier density within the samples. Laser 1205 can also be used as a measurement laser. Not shown is a mechanical shutter in front of laser 1205 to block the beam when not in use. The output beam of laser 1205 is collimated using collimating lens 1206, providing collimated beam 1207.

The above-described beam 1203 from one of the measurement lasers 1201a–1201c is combined with beam 1207 from the carrier generation laser using dichroic mirror 1210 to create combined and collinear beam 1211. As noted above, dichroic mirror 1210 is mounted on a small movable stage/platform to allow wavelength selection for the measuring beam. Combined beam 1211 of these embodiments then passes through 50:50 beam splitter 1212, 90:10 beam splitter 1213, deflector 1215, and objective lens 1216 (100× from Olympus).

Also as noted above, deflector 1215 receives a modulation signal from lock-in amplifier 1231 via connection 1235, which causes the combined beam 1211 to be deflected slightly in a periodic manner about the propagation axis. Lens 1216 focuses the combined beam 1211 onto the surface of wafer 1217, which is mounted on a stage 1218. Although periodic deflection of combined beam 1211 is implemented in some embodiments by deflector 1215 as described above, in alternative embodiments, stage 1218 is used to move the wafer 1217 back and forth in one direction at a fixed frequency as described above in reference to FIG. 10C. Both types of embodiments are illustrated in FIG. 12, although it is to be understood that only one of the two mechanisms for providing relative motion need be used in any given embodiment.

As noted above in reference to FIGS. 10B and 10C, in the apparatus of FIG. 12 as well, the reflected beam (which includes components from the probe beam and the pump beam) is recollimated by lens 1216. Beam splitter 1213 diverts 10% of the combined reflected beam to lens 1226 and camera 1227. The combined reflected beam then enters beam splitter 1212, which deflects it to an optical filter 1221 (FIG. 12).

Filter 1221 passes the light from measurement laser 1201, but blocks light from generation laser 1205. Note that such a filter is not required in the embodiments of FIGS. 10B and 10C because of their use of a single beam. The reflected beam (after being filtered by filter 1221) at the measurement wavelength reaches detector 1223, which generates the above-described analog electrical signal. Filter 1221 of some embodiments of the apparatus of FIG. 12 is mounted on an actuator that enables it to be moved out of the path of the reflected beams, so that laser 1205 may be used by itself in such a configuration to provide a measurement wavelength (e.g. with all the other lasers 1201a–1201c turned off).

In some embodiments, a test structure 1305 (FIG. 13B) is formed (as per act 1311 in FIG. 13A) using the same processes as and at the same time as the integrated circuit 1320 in a production wafer 1330, in the manner described above for act 201 (FIG. 2A). In fact, wafer 1330 of FIG. 13B may be same as wafer 230 of FIG. 2A, i.e. the same wafer can be evaluated by each of the two methods illustrated in FIGS. 2A and 13A respectively.

Figure 13A:
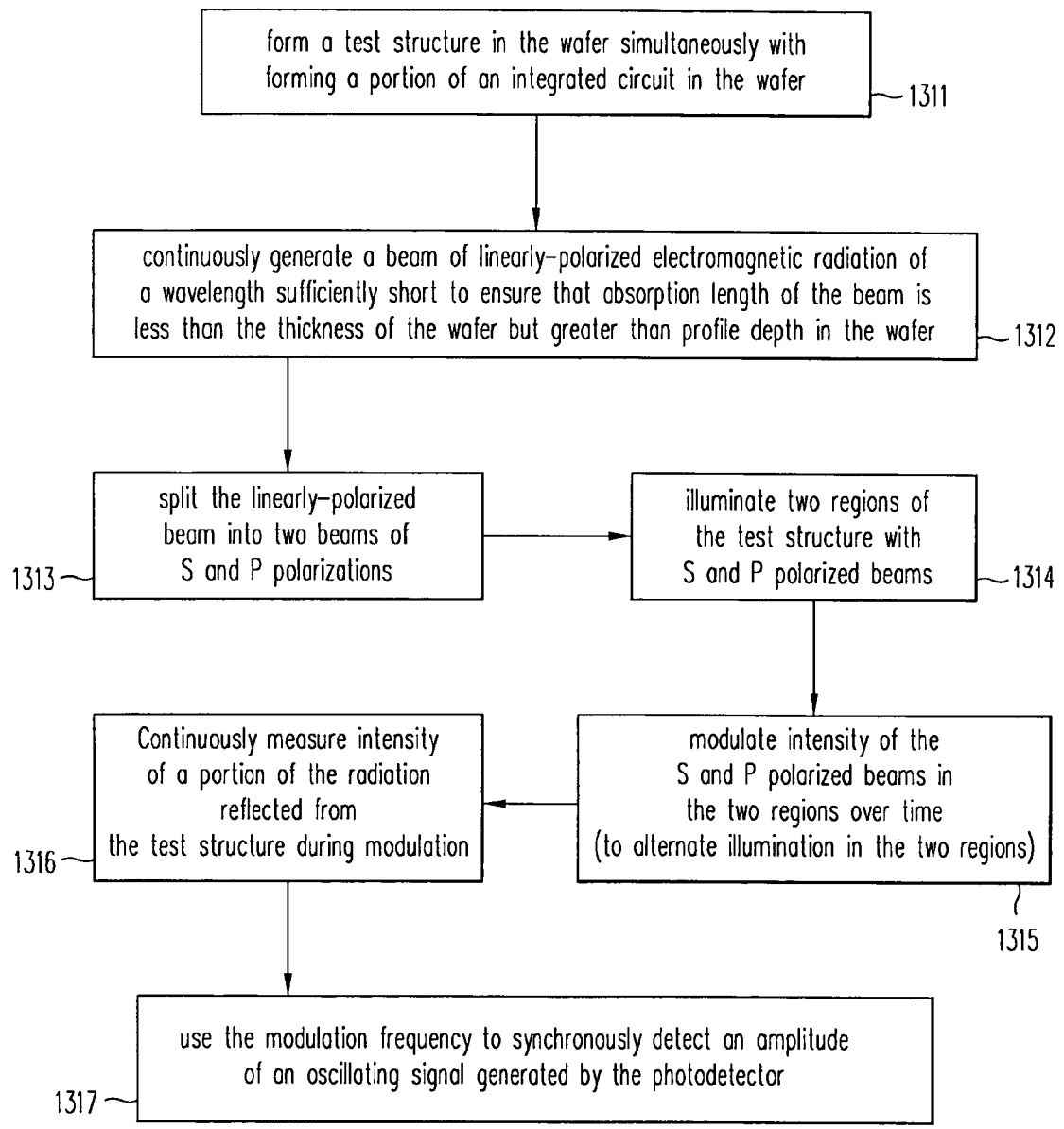
FIG. 13A illustrates, in a flow chart, acts performed in several embodiments of the invention wherein a beam is split into two portions that are respectively incident on two regions of a wafer to be evaluated.

In the method of FIG. 13A, a beam of linearly-polarized electromagnetic radiation is generated in a continuous manner, with a wavelength of the beam being selected to ensure that the absorption length is less than a thickness of the wafer but greater that the profile depth (see act 1312 in FIG. 13A). This act 1312 is similar to act 202 described above for FIG. 2A, except that a beam 1308 (see FIG. 13C) of linear polarization is generated in act 1312.

Thereafter, in the method of FIG. 13A the linearly-polarized beam 1308 (FIG. 13C) is split (as per act 1313) into two beams of S and P polarizations (these polarization directions are orthogonal to one another). Next, the two beams of S and P polarizations are used to illuminate (as per act 1314) two regions of a test structure (or of the integrated circuits depending on the embodiment) on a front surface F of the wafer 1330 (FIG. 13C). The two regions 1301 and 1303 (FIG. 13B) are illuminated simultaneously by the S and P beams forming the respective spots 1309a and 1309b. Although in FIG. 13B, doped region 1301 is illustrated as having a spot 1309a formed by the P beam, and undoped region 1303 has spot 1309b formed by the S beam, an inverse of this orientation can also be used (i.e. S beam illuminating doped region and P beam illuminating undoped region). Regardless of the relative orientation, the spots 1309a and 1309b are positioned symmetrically relative to a boundary 1304 between the two regions 1301 and 1303.

In the method of FIG. 13A, the intensity of the two beams incident on the two regions in the respective spots 1309a and 1309b is modulated as a function of time, as illustrated in act 1315. For example, when intensity of the S polarization is at the maximum and the intensity of the P polarization is at the minimum, then the intensity of the S polarization is gradually reduced and concurrently therewith the intensity of the P polarization is gradually increased. While the intensities of the two beams are modulated, portion of the two beams reflected by the wafer is measured (as per act 1316).

In some embodiments, a linearly-polarized beam 1302 (FIG. 13C) is passed through a half-wave plate 1310 (FIG. 13D) that is being rotated, to generate a beam 1308 that has polarization direction R which changes as a function of time. Specifically, as illustrated in FIG. 13D, an angle θ between direction R of polarization and the z axis is a function of time t. Therefore, in such embodiments, linearly polarized beam 1308 (FIGS. 13C and 13D) is split by passing it through a beam splitter 1307, to generate the S and P beams which are separated by a small angle Ø.

The precise value of separation angle Ø between the two beams depends on a number of factors, such as the type of beam splitter 1307 (e.g. a prism formed by cementing two wedges). Specifically, in some embodiments, beam splitter 1307 can be a Wollaston prism available from (1) CVI Laser LLC, 200 Dorado Place SE, Albuquerque, N. Mex. 87123, as part # WLST-10.0-CA-670-1064, 10° separation angle, wavelength=670–1064 nm, and (2) Melles-Griot, part# 03-PPW-001-15, 15° separation angle, uncoated. Note that other kinds of polarizing beam splitters can also be used as described herein, as long as the beam splitter has a sufficiently small separation angle (e.g. Ø smaller than or equal to 20°). The small separation angle is required to provide a certain amount of physical distance Pd (FIG. 13C) between the beam splitter 1307 and front surface F of wafer 1330, to accommodate an objective lens (not shown) therebetween.

The smaller the length of the objective lens, the larger the separation angle that can be used. In several embodiments of the type described herein, the distance Pd between the wafer and the Wollaston prism is on the order of 2–3 inches thereby to require a Wollaston prism of a small separation angle, such as Ø =10° or even Ø=5°. In several embodiments, the separation angle Ø is selected to be sufficiently large (in view of the distance Pd from the wafer) to ensure that the two beams S and P that are obtained from splitting do not form spots 1309a and 1309b (FIG. 13B) that overlap. Spots 1309a and 1309b may be separated from one another by any distance, e.g. 1 micron or even 10 microns.

Figure 13B:
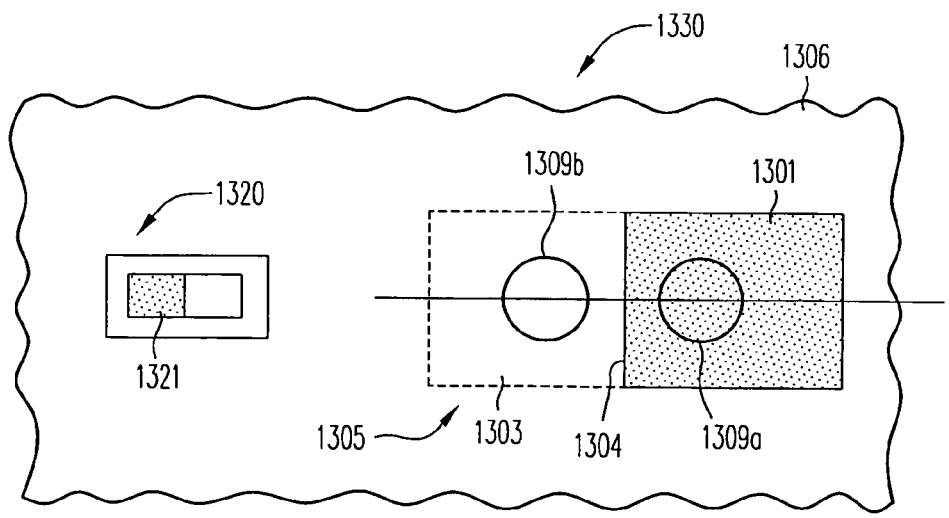
FIG. 13B illustrates, in a plan view, at most two positions of the incident beam formed by splitting a single beam, thereby to illuminate doped region 1301 and the undoped region 1303 of a test structure 1310; also shown in FIG. 13B is an integrated circuit 1320 formed simultaneous with test structure 1310.
Figure 13C:
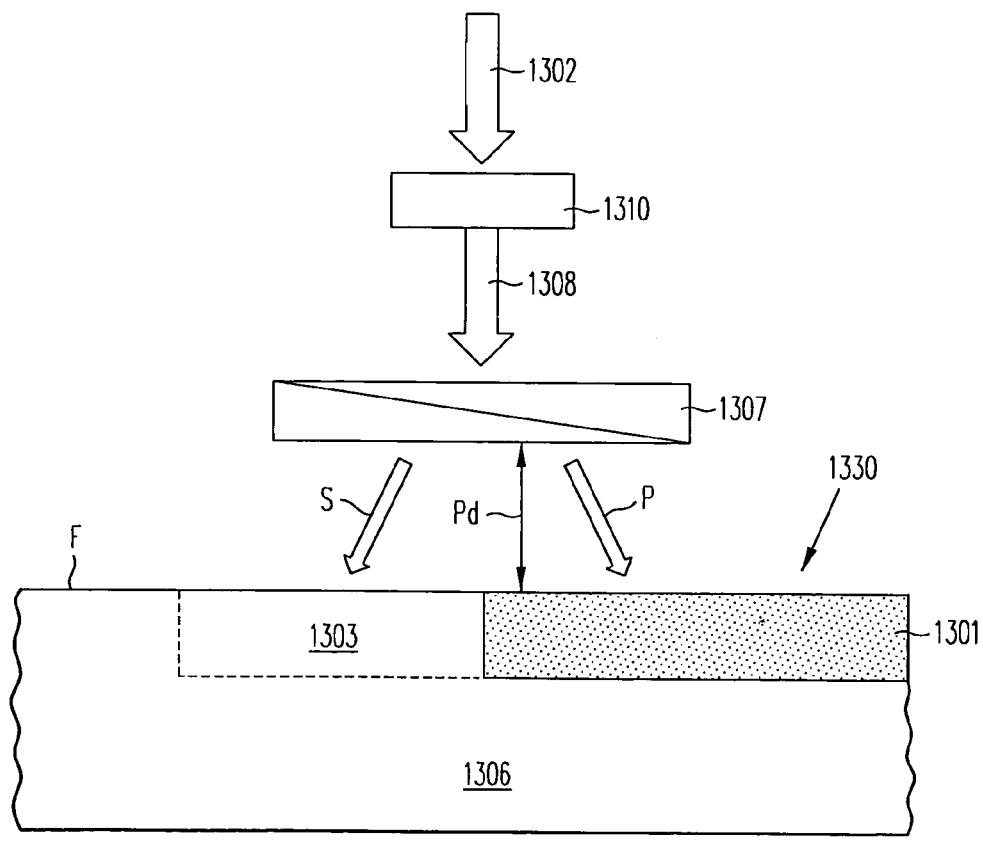
FIG. 13C illustrates, in a side view, the simultaneous illumination of doped region 1301 and undoped region 1303 of a test structure by respective beam portions 1309a and 1309b which are generated by a beam splitter (such as Wollaston prism) 1307 from a single beam 1308 incident thereon.
Figure 13F:
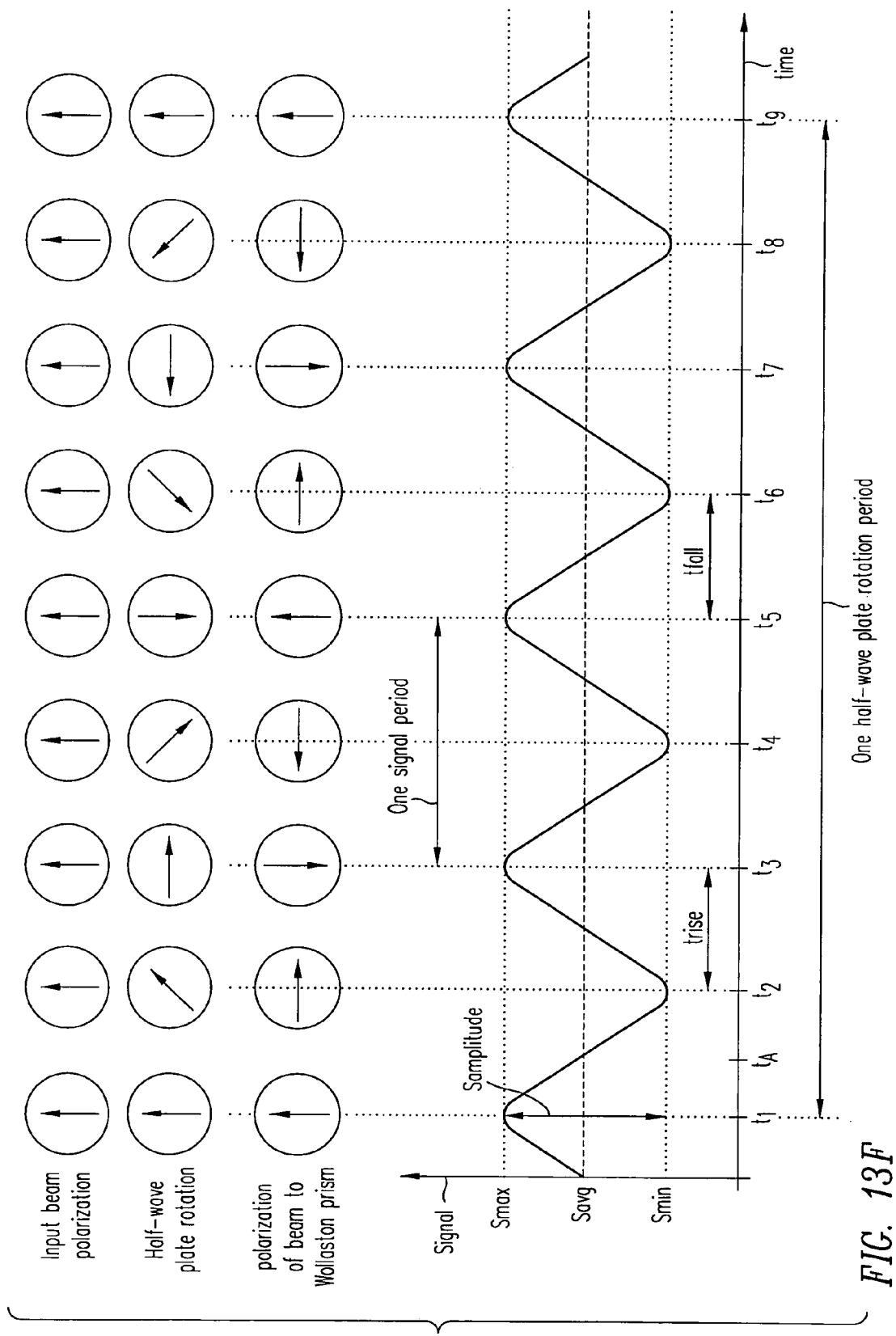
FIG. 13F illustrates, in a graph, the continuous nature of the signal sensed by the photodetector, including the times at which the signal reaches its maximum and minimum and the durations tfall and trise during which the signal falls and rises respectively; also illustrated in FIG. 13F are the relative directions of the input beam's polarization and the half-wave plate crystal axis.
Figure 13G:
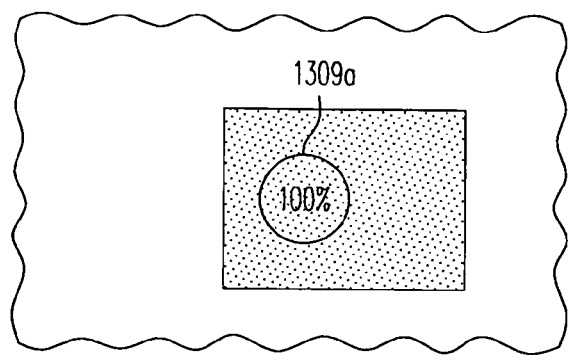
FIGS. 13G–13M illustrate, in a plan view, spots of illumination formed on a test structure by use of the embodiment of FIG. 13C.
Figure 13H:
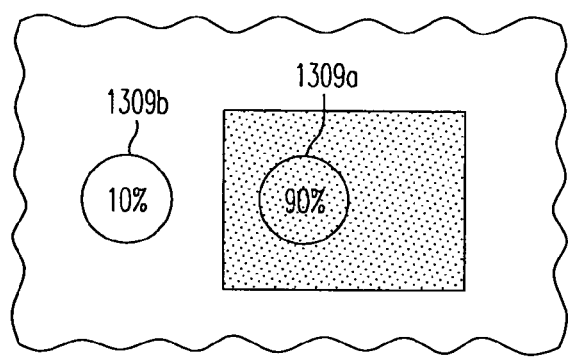
Figure 13I:
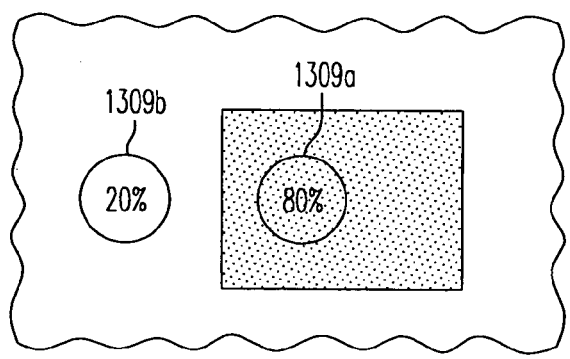
Figure 13J:
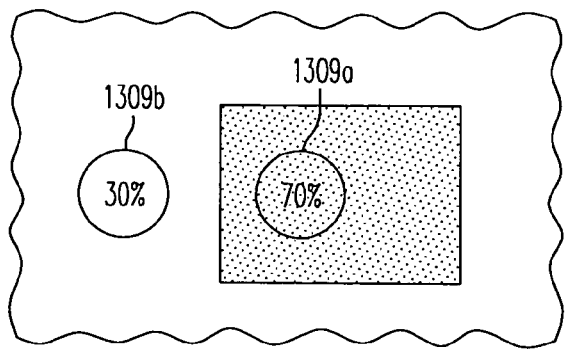
Figure 13K:
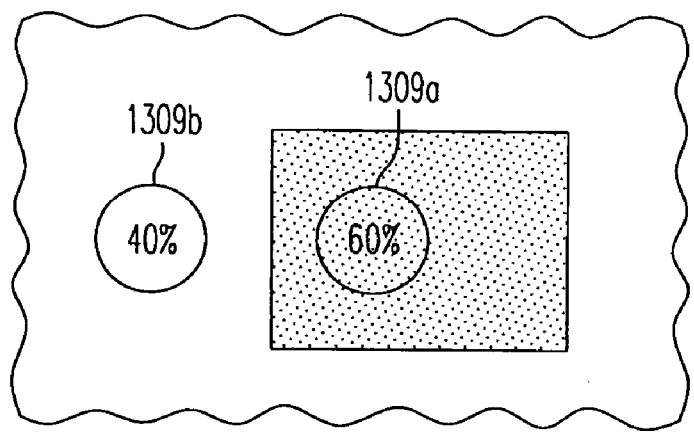
Figure 13L:
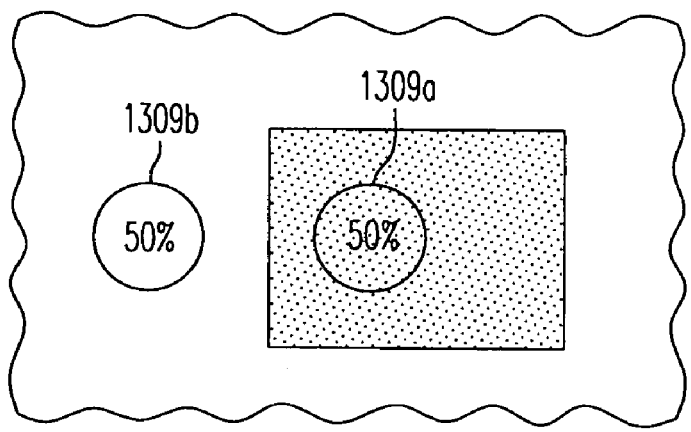

When beam 1308 which is incident on the beam splitter 1307 (FIG. 13D) is linearly polarized in the same direction R as the optical axis z of the prism, only the S beam emerges from beam splitter 1307, and at this moment the P beam has zero intensity as illustrated in FIG. 13G. As noted above, beam 1308 having the direction R along the z axis is produced when the half-wave plate 1310 has its axis in line with the polarization direction of input beam 1302 (FIG. 13C). Therefore, at the just-described moment, which is illustrated as t1 in FIG. 13F, an electrical signal which is measured by a photodetector is at its maximum value Smax. As the half-wave plate 1310 is rotated, direction of polarization R of beam 1308 changes relative to the optic axes of the beam splitter 1307, and hence the intensities of the S and P beams also changes. In some embodiments, beam splitter 1307 is a Wollaston prism.

Figure 13M:
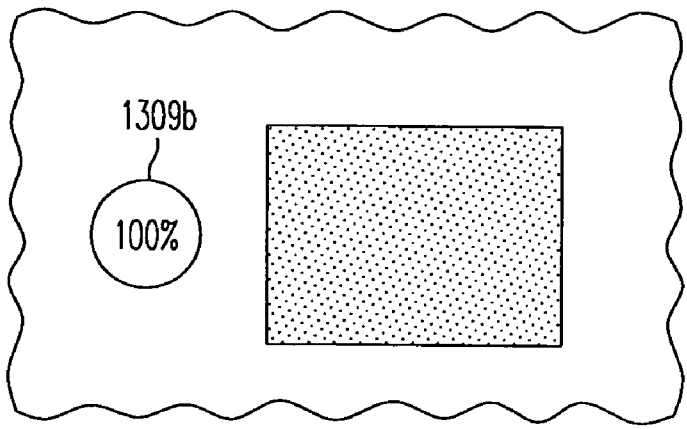

The fall and rise in intensities of the two beams in the undoped and doped regions respectively is illustrated for certain moments in FIGS. 13G, 13H, 13I, 13J, 13K and 13L, until the two beams become equal in intensity, and thereafter the intensities change in the reverse manner, until 100% of the intensity is in the doped region as illustrated in FIG. 13M. Since the rotation continues, the intensity thereafter reduces in the doped region and increases in the undoped region until the intensities are reversed as shown in FIG. 13G. Therefore, illumination alternates between the undoped region (FIG. 13G) and the doped region (FIG. 13M).

At a moment of equal intensity (FIG. 13L) of spots in the two regions, the intensity of reflection detected by the photodetector indicates a reflectivity of the wafer 1330 which is average (indicated in FIG. 13F by Savg at the time tA) of the reflectivities of the two regions 1301 and 1303 (FIG. 13B). At time tA, the input beam 1308 is linearly polarized at a 45° angle in the direction R with respect to the prism's optical axes x and z, and the beam is refracted into two equal-intensity, orthogonally-polarized beams S and P, with each polarization in the same direction as the respective optical axes.

Therefore, when the input beam 1308 has its polarization rotated in a periodic manner at a fixed frequency, the intensity of the output beams from beam splitter 1307 is alternated between one refracted direction S to the other refracted direction P, and therefore the resulting signal detected by the photodetector has a triangular waveform illustrated in FIG. 13F. In such embodiments, the refracted beams are aligned to the doped and undoped regions, and these two regions are then alternately probed in a periodic manner, generating a fluctuating signal detectable by a lock-in amplifier. The signal period of the analog electrical signal generated by the photodetector (which is provided to the lock-in amplifier) is one fourth the rotation period of the half-wave plate. Unlike the method of beam scanning, this method of beam splitting does not produce anomalous spikes in the signal train, since the probing beam never crosses the boundary between doped and undoped regions.

Figure 13N:
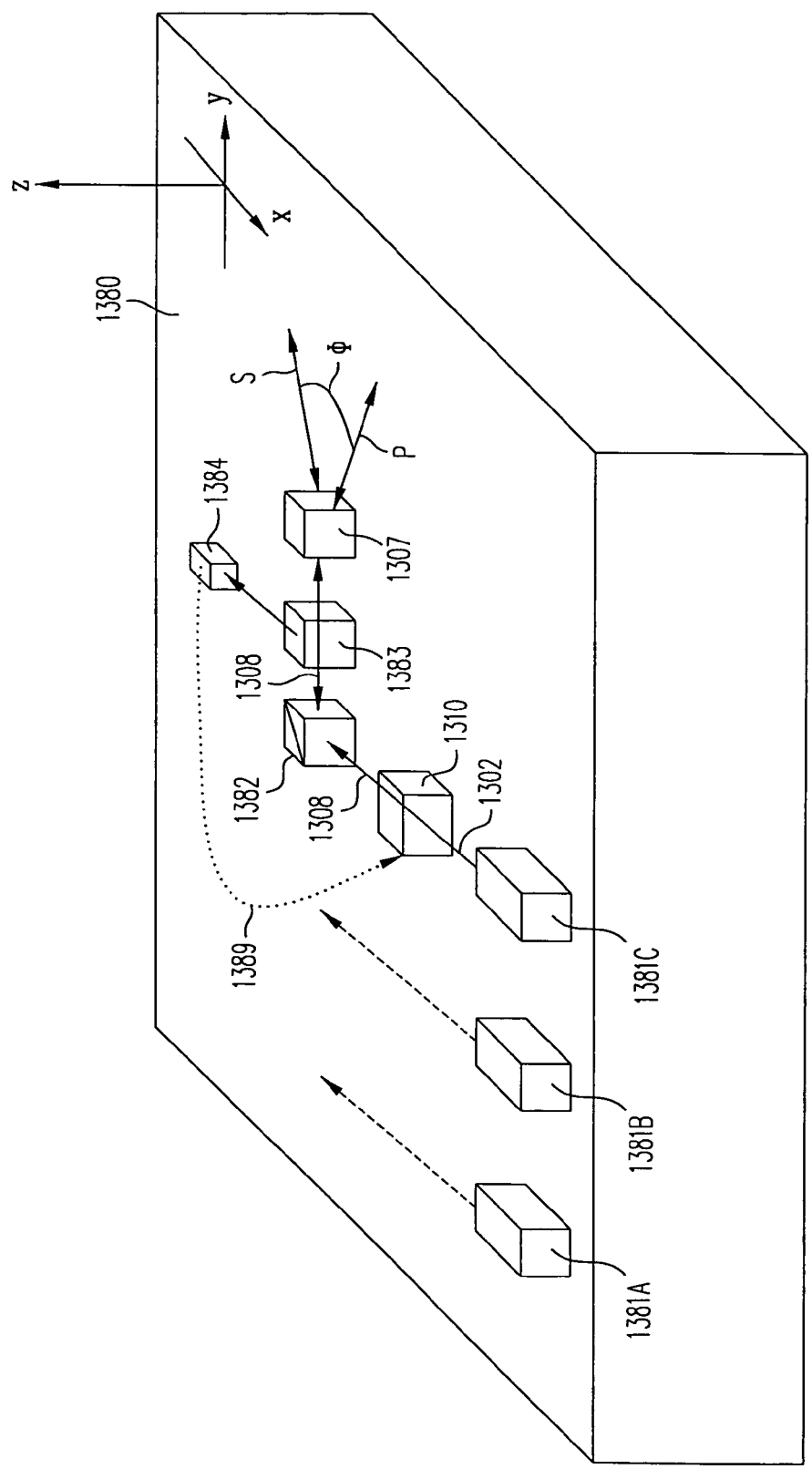
FIG. 13N illustrates, in a three dimensional view, the relative positions of various optical components in an embodiment that uses a Wollaston prism to illuminate two regions of a wafer, and a lock-in amplifier that uses a frequency of rotation of a half-wave plate (through which a polarized beam passes) to measure amplitude of a signal generated by the photodetector.
Figure 130:
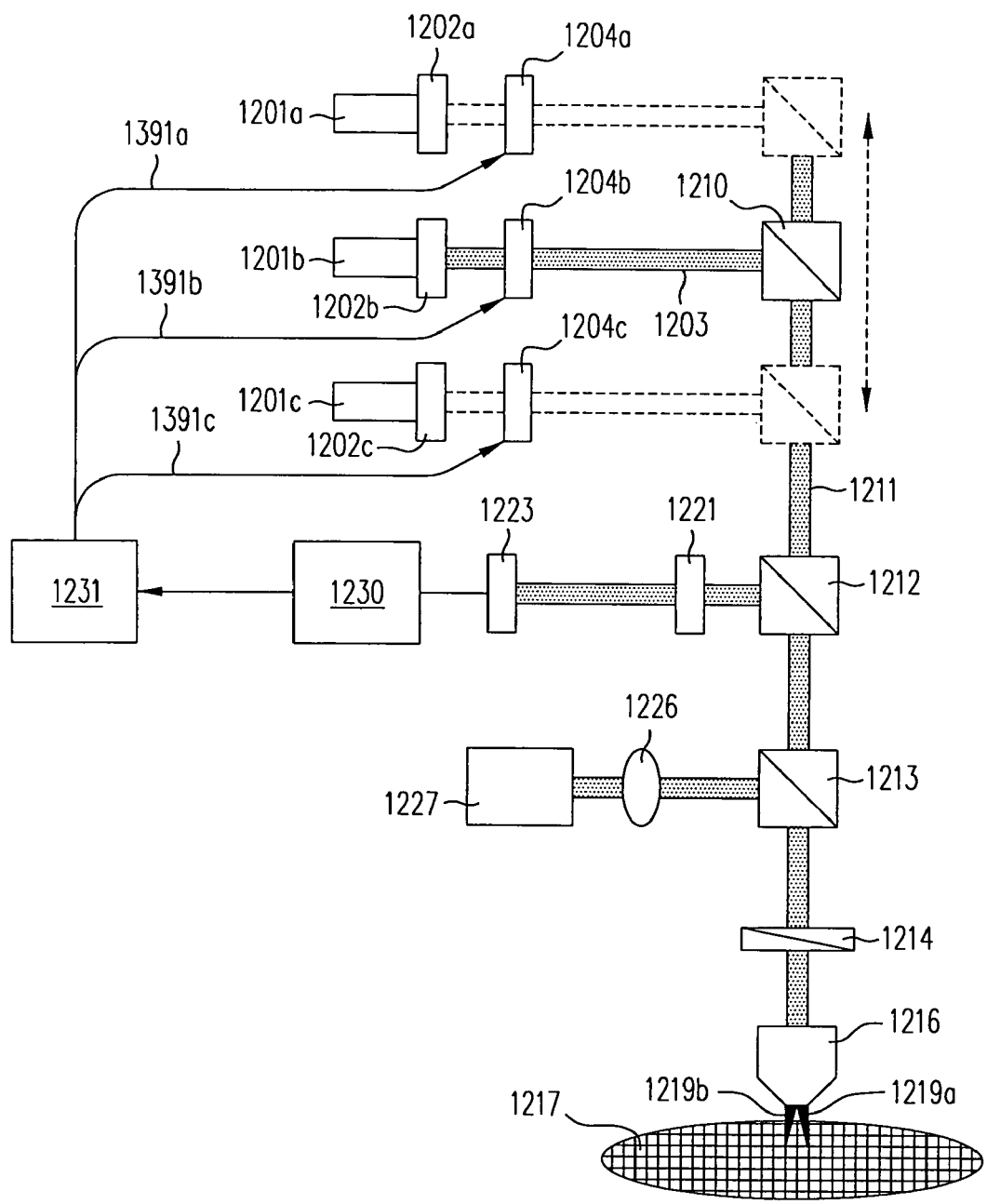

FIG. 13N illustrates one such embodiment of the invention, where a single incoming laser beam 1308 having rotating polarization is split into two orthogonally polarized beams S and P by a beam splitter 1307, in order to illuminate the doped and undoped regions of a wafer (not shown). As noted above, the S and P beams each have an intensity that changes over time, depending on the direction R of polarization of the input beam 1308 relative to the prism's two optical axes which are shown in FIG. 13E as being in the directions z and x respectively, and these directions are illustrated in FIG. 13D relative to the direction of travel of the beam 1308. Note that the two beams S and P are shown in FIG. 13N as being in a plane parallel to the x-y plane which is also the plane of an optical bench 1380.

Optical bench 1380 supports various optical components, such as lasers 1381A–1381C for generating the beam 1302, half-wave plate 1310, dichroic mirror 1382, and beam splitter 1307. Dichroic mirror 1382 is mounted on a rail on the optical bench to allow it to translate along the y axis, so as to select one of lasers 1381A–1381C. Also mounted on bench 1380 is a non-polarizing beam splitter 1383 (also called "detection system beam splitter") which is in line between dichroic mirror 1382 and beam splitter 1307, and is configured to allow the beam from mirror 1382 to pass therethrough to beam splitter 1307, but at least a portion of a reflection in the opposite direction is diverted to a photodetector 1384 that in turn is coupled to a lock-in amplifier (not shown). The lock-in amplifier is electrically connected (by wire 1389) to a motor (also not shown) that turns the half-wave plate 1310.

FIG. 13O shows a hardware configuration for some embodiments which use split beams with changing intensities to probe the doped and undoped region of a test structure. Half-wave plates 1204a, 1204b, and 1204c are placed in the path of beam 1203 and are rotated at a fixed frequency about the beam propagation axis. As a result, the linear polarization of the measuring beam is also rotated, so that when the beam passes through Wollaston prism 1214, the beam is split into two orthogonally polarized beams 1219a and 1219b with alternating intensities.

With proper alignment, beams 1219a and 1219b are placed within the doped and undoped regions, respectively.

On the return path towards photodetector 1223, the beams are recombined by Wollaston prism 1214, such that the signal detected by photodetector 1223 is an analog fluctuating electrical signal with amplitude proportional to the reflectivity difference between the doped and undoped regions. Also shown in FIG. 13O is a connection (such as one of wires 1391a–1391c) from lock-in amplifier 1231 to a motor that can rotate the half-wave plate (e.g. one of plates 1204a–1204c) at a frequency set by lock-in amplifier 1231. Other means of rotating the polarization of the measuring beam may be employed; they include but not limited to electro-optic and liquid-crystal modulators. In this embodiment, several Wollaston prisms 1214 may be used, mounted on a turret or variable position actuator. Each prism sets the spacing between the two beams, so that a selection of spacings is available to accommodate different patterns to be measured.

Figure 14A:
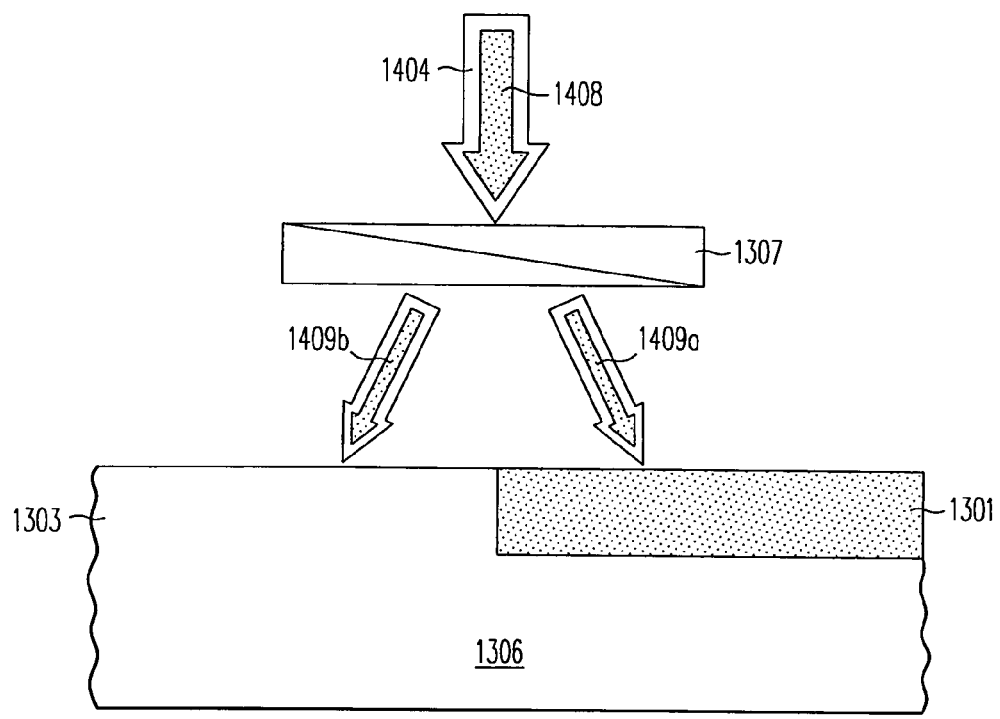
FIG. 14A illustrates, in a side view, an alternative embodiment wherein two beams that are coaxial with one another are both split by a Wollaston prism, for evaluation of a test structure of the type described herein.
Figure 14C:
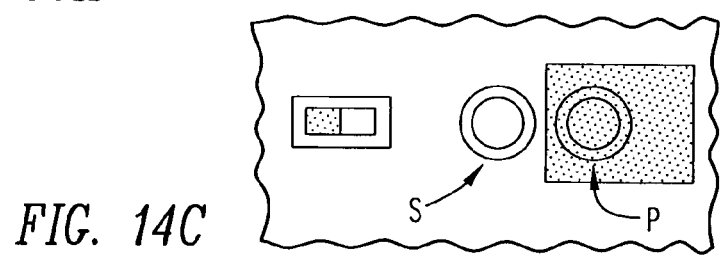
FIGS. 14C–14E illustrate, in a plan view, exactly two positions of one incident beam and at most two positions of another incident beam due to splitting of both beams as illustrated in FIGS. 14A and 14B.
Figure 14D:
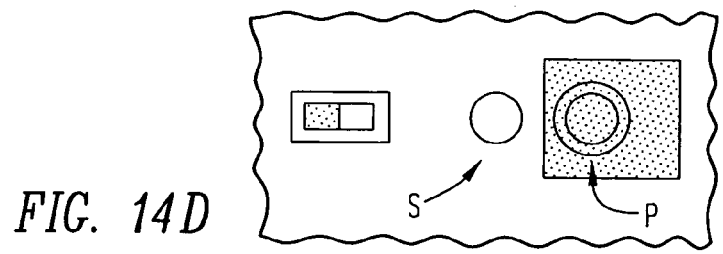
Figure 14E:
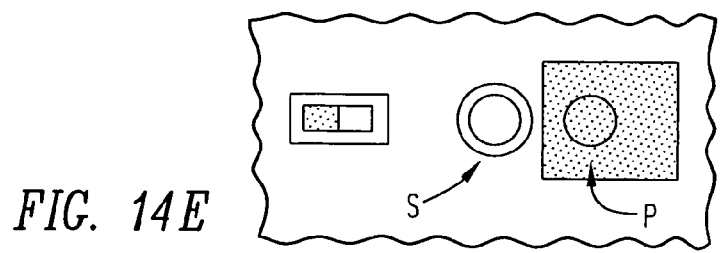

In other embodiments of the type described above in reference to FIGS. 13A–13N, the same portion of the doped 1301 and undoped 1303 regions are illuminated with an additional laser beam (also called "pump" beam) 1404 (FIG. 14A) that is collinear with the above-described laser beam (also called "probe" beam) 1408. Both beams are split to form a pair of concentric (or overlapping) spots for the S polarized light in one region and also form another pair of concentric (or overlapping) spots for the P polarized light in another region, as illustrated in FIG. 14C. Note that only the P and S components of probe beam 1404 have their intensity modulated, while the P and S components of pump beam 1408 do not have modulating intensities. For this reason, as illustrated in FIG. 14D, the S component of the pump beam continues to illuminate an undoped region even when the S component of the probe beam has zero intensity. The opposite situation is illustrated in FIG. 14E. As noted above, in some embodiments, the intensity of probe beam 1408 is modulated between the two regions by use of a rotating half-wave plate, in the manner described above in reference to FIGS. 13A–13N.

Pump beam 1404 has photon energy greater than the band-gap of the semiconductor, in order to generate excess carrier distribution, in the same manner as the method described in U.S. Pat. Nos. 6,323,951 and 6,049,220 by Borden. In such an embodiment, the value of Samplitude obtained from measuring the fluctuation in an analog electric signal sensed by a photodetector as the intensity of reflected radiation at the wavelength of probe beam 1408 is now a measure of the difference in excess carrier distribution between the doped and undoped regions. Such an Samplitude is sensitive to other parameters of the doped layer, such as defect density and oxide charge, in addition to its sensitivity the profile depth, the doping concentration, and the profile abruptness. The difference signal of interest is given by equation (13).

Pump beam 1404 can be unpolarized, or circularly polarized or polarized linearly (at any angle relative to the two axes of the Wollaston prism, although in one embodiment it is at 45 degrees thereby to ensure that the two regions have equal illumination of the pump beam). Note that if pump beam 1404 is linearly polarized along the direction of one axis of the Wollaston prism, then only one region (e.g. the doped region) receives the full intensity of the pump beam, and the other region receives no energy.

Figure 14B:
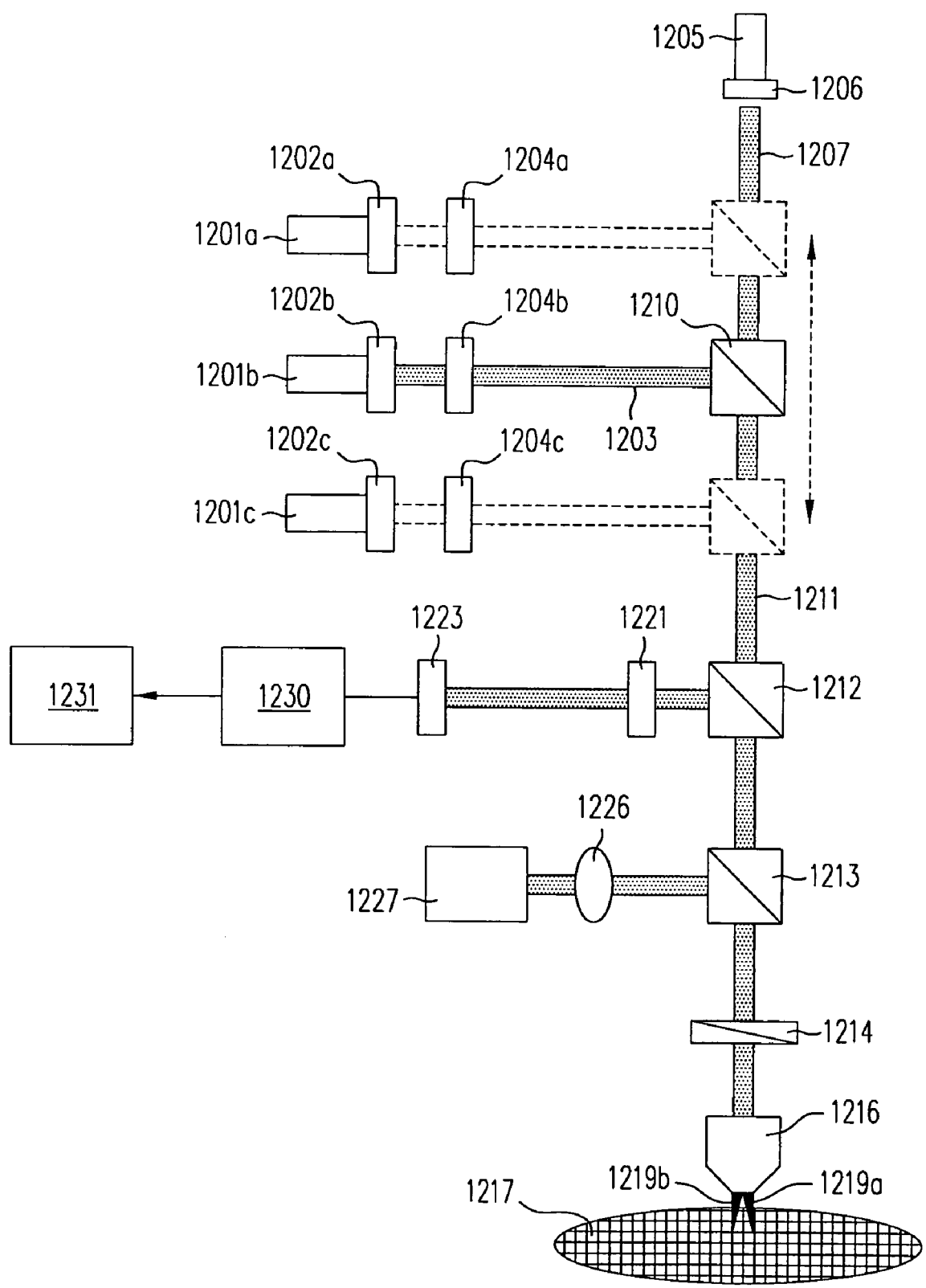
FIG. 14B illustrates a hardware configuration of the type illustrated in FIGS. 13A–13I for the alternative embodiment of FIG. 14A.

FIG. 14B shows a hardware configuration for some embodiments which use a probe beam with changing intensities of S and P components simultaneously with a pump beam with fixed intensities of the S and P components. The hardware configuration in FIG. 14B is identical to the corresponding configuration illustrated in FIG. 13O except that in FIG. 14B, the apparatus also includes an additional laser source 1205 and a collimating lens 1206 located in a path to the dichroic mirror 1210. In the embodiment of FIG. 14B, the beam from laser source 1205 is oriented along the direction of travel of the dichroic mirror 1210.

Figure 15A:
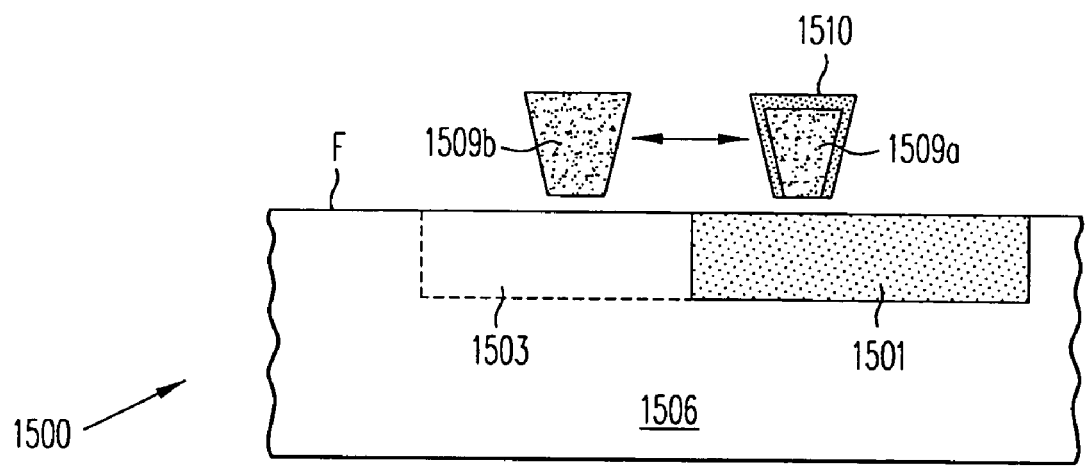
FIG. 15A illustrates, in a side view, an alternative embodiment wherein one beam is split by a Wollaston prism and another beam is modulated at a predetermined frequency, used in evaluation of a test structure of the type described herein.

In still other embodiments, two beams are used similar to FIGS. 14A–14E although only one of the two beams (the probe beam) is split. Therefore, as illustrated in FIG. 15A, probe beam forms the two components 1509a and 1509b. Depending on the embodiment, components 1509a and 1509b can be made respectively incident on the doped and undoped regions (at a front surface F of a wafer 1500), although in other embodiments the two components may be made incident on the same type region (e.g. both only on a doped region). In these embodiments as well, the principles of junction depth measurement already described in U.S. Pat. Nos. 6,323,951 and 6,049,220 (both incorporated by reference herein in their entirety), are utilized except that the doped region 1501 is simultaneously illuminated by both pump beam 1510 and probe beam component 1509a, whereas the undoped region 1503 is illuminated only by the probe beam component 1509b.

This beam configuration can be achieved by using a Wollaston prism, a circularly polarized probe beam, and a linearly polarized pump beam with its polarization direction aligned to one of the Wollaston prism's optic axis. Before passing through the objective lens, the Wollaston prism splits the measuring beam into two orthogonally polarized beams 1509a and 1509b with equal intensities. With proper alignment, beams 1509a and 1509b can be placed within the doped region 1501 and undoped region 1503, respectively. The linear polarization of the pump beam is chosen for example to be oriented along the x-direction of the Wollaston prism axis (see FIG. 13E) that deflects it collinear with beam 1509a, so that beam 1510 also illuminates the doped region e.g. so that concentric spots are formed thereon. As in the other embodiments involving a carrier generation beam, the pump beam may have a slightly different spot size than the measuring (probe) beam. The Wollaston prism recombines the reflected probe beams from the doped and undoped areas as described above.

As noted in the above-described U.S. Pat. Nos. 6,323,951 and 6,049,220, an intensity of the pump beam (also called "carrier generation beam") is modulated as a function of time, at a predetermined frequency. The frequency is selected to be sufficiently small to avoid the creation of a wave of carriers in an illuminated region. Reflected beams from the doped and undoped areas are recombined by the Wollaston prism.

The reflected combined beam from the Wollaston prism is then split again (by a beam splitter that is polarizing) into two orthogonally polarized beams, before they are detected separately by two photodetectors. The axis of the polarizing beam splitter (also called "photodiode beam splitter" due to its adjacency to two photodiodes that receive their respective signals therefrom) is oriented at 45° angle with respect to the two axes of the Wollaston prism, such that one photodetector measures the sum while the other photodetector measures the difference of reflected electromagnetic radiation from the doped and undoped area at the wavelength of the probe beam.

The relation between wavelengths λ1 and λ2 of the probe beam and the pump beam respectively is a critical aspect in one embodiment and leads to unexpected results. For example when the pump beam contains photons having energy above silicon's bandgap energy and the probe beam contains photons having energy approximately the same as or less than the bandgap energy. In this example, for a silicon wafer the 830 nm and 1033 nm wavelength beams provide one or more benefits described herein.

Wavelength 830 nm is considered particularly suitable for the pump beam because the absorption length in silicon is about 15 microns. Thus, the absorption length is much greater than the junction depth, and creation of excess charge carriers is nearly uniform over the depth of concern in the measurement. Because the photon energy is close to the bandgap energy, photon generation is more efficient, with less energy going directly into heating the semiconductor.

Also, the absorption length at wavelength 1033 nm is about 373 microns, and therefore the number of excess carriers being created by such a probe beam is sufficiently low to ensure minimum perturbation to the excess carrier distribution. Moreover, the absorption length at wavelength 1033 is short enough that very little reflection from a back surface of the wafer is seen (wafers are typically 600–800 microns thick), since the back surface reflection can potentially cause spurious signals.

Figure 16:
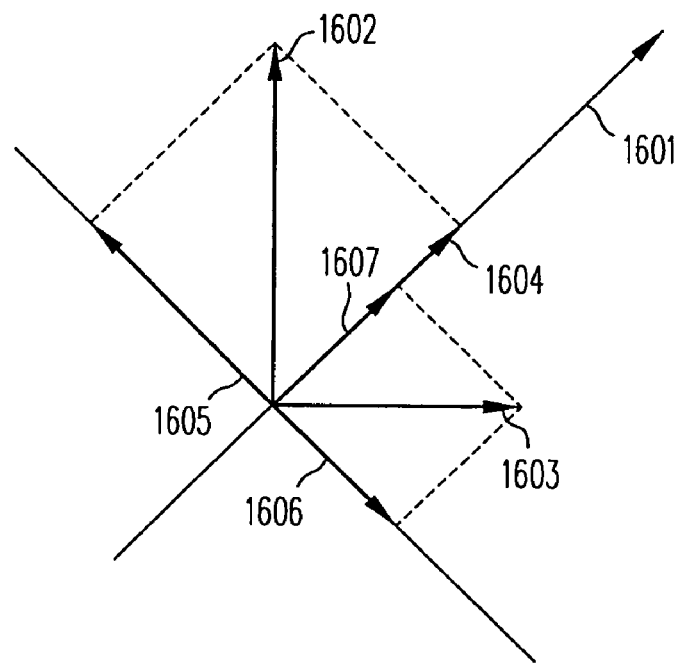
FIG. 16 illustrates, in a two dimensional graph, relative angles of various beams and their polarizations for the embodiment of FIGS. 15A and 15B.
Figure 15B:
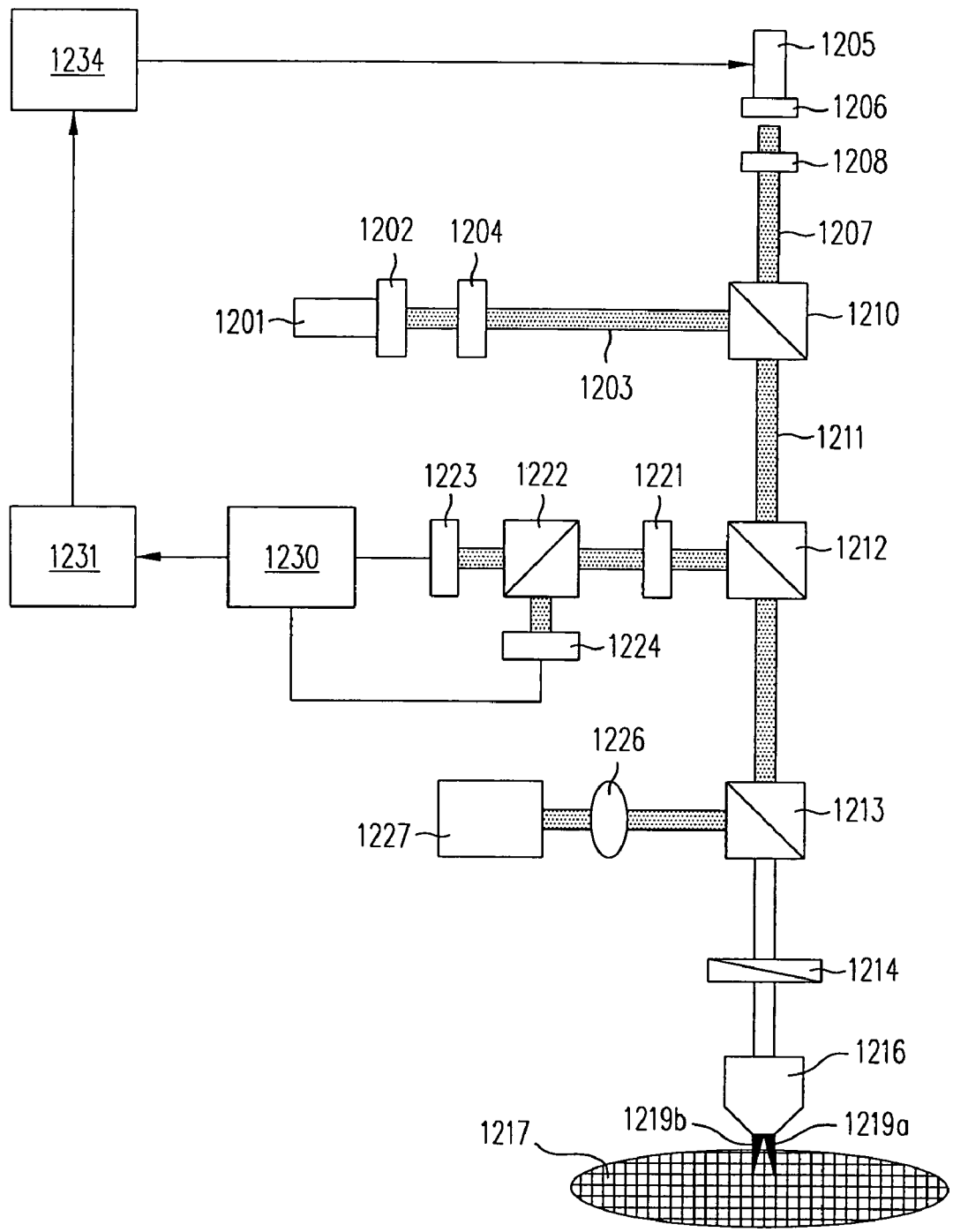
FIG. 15B illustrates a hardware configuration of the type illustrated in FIG. 14B for the alternative embodiment of FIG. 15A.

The relationship between the beam splitter axis and the probe beam polarization is depicted in FIG. 16. Direction 1601 is the direction of the beam splitter axis, which is at a 45° angle with respect to the S polarization direction 1602, and the P polarization direction 1603 of the probe beam. As viewed from the beam traveling towards photodetector 1384, directions 1602 and 1603 coincide with the z- and y-axes of FIG. 13N, respectively. As a result, one photodetector detects the sum of signals 1604 and 1607, while another photodetector detects the difference between signals 1605 and 1606 of the S and P polarizations. The intensities of the S and P polarizations of the probe beam reflected by the wafer are slightly different due to the different properties of the doped and undoped regions; their difference is exaggerated in FIG. 16 for clarity. The electrical signals from the output of each of the two photodetectors are sinusoidal waveforms that are electronically subtracted from one another and amplified. Such a difference signal is indicative of the properties of the doped region, and an amplitude of this signal is detected using a lock-in amplifier to enhance the signal to noise ratio (since the pump beam is modulated at a fixed frequency).

A hardware configuration illustrative of embodiments of the type described above is shown in FIG. 15B. In this configuration, there is only a single measurement laser 1201, which is a semiconductor diode laser operating at 980 nm wavelength. Its output beam is collimated by collimating lens 1202, and then passes through quarter-wave plate 1204 to produce collimated beam 1203 that is circularly polarized. The carrier generation laser 1205 is a semiconductor diode laser operating at 830 nm wavelength. Its output is collimated by collimating lens 1206, and then passes through half-wave plate 1208 to produce collimated beam 1207 that is linearly polarized at 45° angle with respect to the normal direction of the optical bench (z-axis direction in FIG. 13N).

Beams 1203 and 1207 are combined using dichroic mirror 1210 (such as a partially transmissive mirror, e.g. part number SWP45-Rp1047-Tp830 available from CVI Laser of Albuquerque, N. Mex.) to create a combined and collinear beam 1211. This combined beam passes through 50:50 non-polarizing beam splitter 1212 (also called "detection system beam splitter"), e.g. part number 10BC17 MB.2 from Newport Corp., Irvine, Calif., and a 90:10 beam splitter 1213 (available from Precision Applied Products of Fullerton, Calif., by specifying 93.3% transmission at 0.83 microns wavelength and 90% transmission at 1.48 microns wavelength), a Wollaston prism 1214 and an objective lens 1216 (such as a 100×, 0.8 NA lens made by Olympus of Tokyo Japan). Objective lens 1216 focuses the combined beam 1211 onto wafer 1217. Note that the 90:10 beam splitter 1213 is also called "vision system beam splitter".

Wollaston prism 1214 splits the probe beam into S and P polarized portions before entering the objective lens 1216, resulting in two focused beams 1219a and 1219b on the front surface of wafer 1217. The spots formed by beams 1219a and 1219b are typically separated by a distance of 5–20 μm. With proper alignment, spots formed by beams 1219a and 1219b are placed within the doped and undoped regions, respectively of wafer 1217.

The optic axes of the Wollaston prism 1214 is oriented at 0° and 90° with respect to the normal direction of the optical bench (or along the z- and x-directions of FIG. 13N), such that the two orthogonally polarized beams 1219a and 1219b have polarizations oriented at 0° and 90° with respect to the optical bench. The reflected beams are re-collimated by lens 1216 and recombined by Wollaston prism 1214. Beam splitter 1213 (mentioned above) diverts 10% of the return beam to lens 1226 and camera 1227, which provide a system to align the two beam spots to regions in the test structure of interest. Not shown is an auto-focus system that consists of a pinhole and a detector, which also uses the portion of the return beam diverted by beam splitter 1213. The remaining portion of the return beam then enters detection system beam splitter 1212, which deflects a portion of it to optical filter 1221. Filter 1221 passes the light from measurement laser 1201, but blocks light from generation laser 1205 (i.e. any reflected portion of the pump beam).

The portion of the probe beam from filter 1221 is thereafter split into two orthogonally polarized beams by a polarizing beam splitter 1222, (also called "photodiode beam splitter") whose axis can be rotated. In such an embodiment, the axis of photodiode beam splitter 1222 is oriented at 45° angle with respect to the two axes of Wollaston prism 1214, such that one detector 1223 detects the sum of the reflected probe beams coming from the doped and undoped regions, while detector 1224 detects the difference. Detectors 1223 and 1224 are silicon photodiodes. The photodiode currents are converted to voltages and subtracted from each other electronically using amplifier 1230, the output of which goes to lock-in amplifier 1231. The output of lock-in 1231 goes to a computer 1232 which receives the signal and presents it to the user or other data collection systems. Lock-in 1231 includes a frequency reference that is used to modulate laser driver 1234, which provides a modulated drive output for generation laser 1205.

The amplitude of the reflection of beam 1509a from doped region 1501 is given by:

$$E_S = r_{sd} E_o + t^2 r_j e^{-i2k(n_o + n_d)z_j} E_o \qquad (16),$$

whereas the amplitude of the reflection of beam 1509b from undoped region 1503 is given by:

$$E_P = \frac{1-n_o}{1+n_o} E_o e^{-i\frac{\pi}{2}}. \qquad (17)$$

The exponential factor in equation (17) accounts for the 90° ($\pi$/2) phase shift between S and P polarization in the probe beam because it is circularly polarized. One photodetector output is proportional to the intensity of the sum of the two reflected amplitudes $E_S$ and $E_P$, while the other photodetector output is proportional to the intensity of the difference of these same two amplitudes. The signal of interest is the difference between these two photodetector outputs, i.e.:

$$S = |E_S + E_P|^2 - |E_S - E_P|^2 \qquad (18).$$

Substituting equations (16) and (17) into equation (18), it can be shown that the difference signal is given by:

$$S = A \frac{|\beta|(1-n_o)E_o^2}{(1+n_o)^3} \int_0^\infty \sin(2kn_o z) \frac{dN}{dz} dz, \qquad (19)$$

where A is a wavelength dependent coefficient representing transmission loss through optical components, photodetector conversion efficiency, and amplifier gain factor. All of the other parameters have the same definitions defined previously. N refers to the excess carrier concentration in the doped region generated by beam 1510. The form of equation (19) allows the possibility of an arbitrary doping profile leading to an excess carrier profile as a function of depth N(z).

Figure 17A:
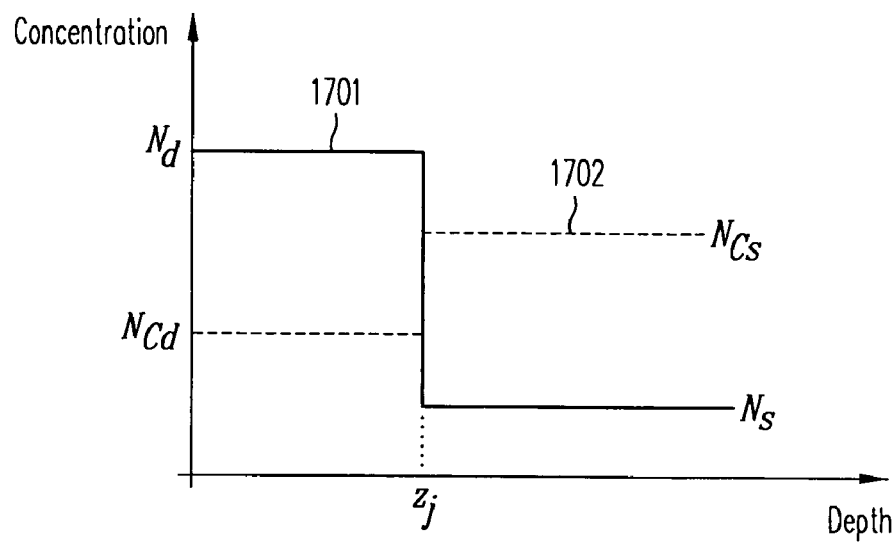
FIG. 17A illustrates, in a graph, the concentration of dopants as a function of depth, for an ideal case of a perfectly abrupt doping profile.

For the ideal case of a perfectly abrupt doping profile, shown as curve 1701 in FIG. 17A, the resulting excess carrier profile resembles a step function, shown as curve 1702 in FIG. 17A. In this case, the derivative dN/dz of the excess carrier profile becomes a delta function given by:

$$\frac{dN}{dz} = (N_{Cs} - N_{Cd})\delta(z - z_j). \qquad (20)$$

Substituting equation (20) into equation (19) produces a simplified form of the difference signal given by:

$$S = A \frac{|\beta|(1-n_o)E_o^2}{(1+n_o)^3} (N_{Cs} - N_{Cd}) \sin(2kn_o z_j). \qquad (21)$$

Figure 17B:
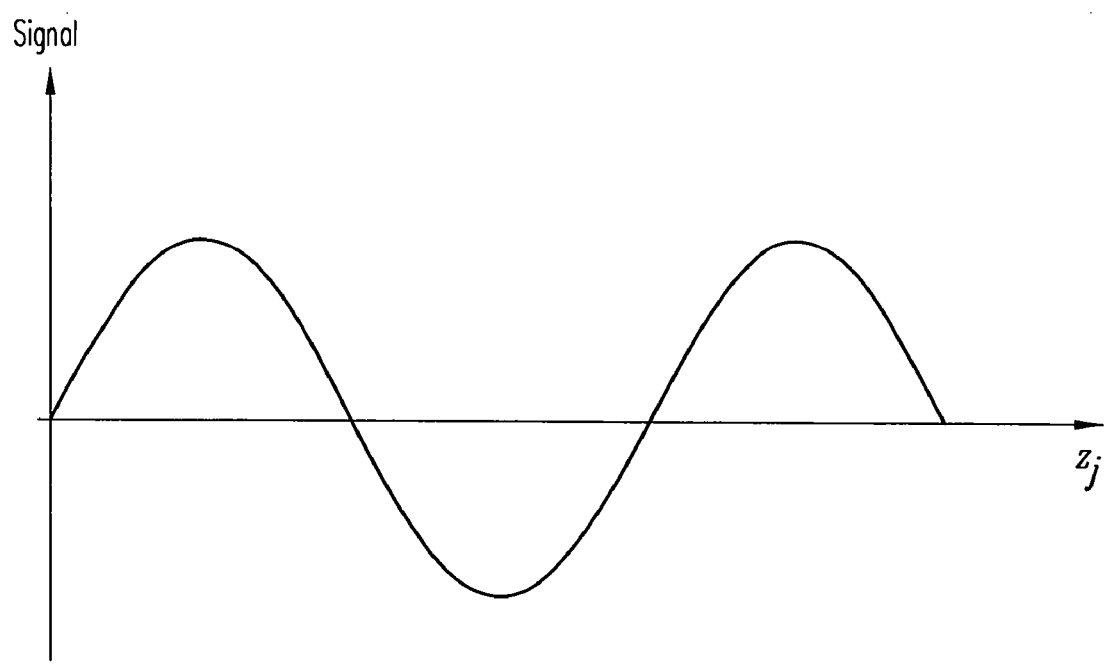
FIG. 17B illustrates, in a graph the sinusoidal nature of the measured signal as a function of the depth of the doping profile.

The signal has a sine dependence on the depth of the doping profile ($z_j$), as shown in FIG. 17B. The above-described sine dependence has the advantage that the signal being measured provides improved resolution as profile depth ($z_j$) gets smaller in response to improvements in wafer fabrication technology. This is because the sine curve passes through the origin (in contrast to a cosine curve that remains practically unchanged in a small neighborhood around the origin).

This embodiment can also be implemented on an un-patterned sample, i.e. a wafer that is doped over its entire area. In this case, no alignment on a particular pattern is needed, the two beams can be placed anywhere on the wafer. Since one of the probe beam is not accompanied by a carrier generation beam, its reflection property is very similar to the reflection from an undoped region, so the signal is the same as given by equation (19).

The above discussion provides a description of several embodiments. Additional embodiments and variations of such embodiments will be apparent to the skilled artisan in view of this disclosure. Several such embodiments are described next.

For example, the method of some embodiments of the invention may be applied to measure the properties of pre-annealed implant wafers. In addition, the method of may be applied to measure the properties of Silicon-On-Insulator (SOI) wafers, both pre and post-annealed. The measurement may also be used to determine the difference in dielectric coating thickness in two regions.

In addition, the above description presents use of the some embodiments for process control. However, embodiments of the type described herein may also be used for process development. For example, if a development engineer wants to compare the profile abruptness that is possible with different laser anneal treatments, an Samplitude measurement of the type described herein can provide such information. For this case, the types of test structures that can be used for evaluation are expanded than some of the test structures described above, because it is no longer necessary to manufacture the test structures within a standard flow for the manufacture of integrated circuits. For example, it is possible to use a mask of narrow poly lines, then put on spacers (silicon nitride layers on the side of the poly lines, as are commonly applied to polysilicon gates in transistors), then anneal before removing the mask to capture stress effects that the spacers may introduce. Other custom adaptations of test structures for process development are limitless in possibility, but would employ the principles discussed above.

Also, as will be apparent to the skilled artisan in view of the disclosure, any of the following properties can be determined by use of one or more Samplitude measurements of the type described herein on a wafer prior to annealing: the dose of implants in a doped region, profile depth and profile abruptness. Moreover, similar measurements after anneal are used in some embodiments to determine the depth of an annealed semiconductor junction, the dose of a doped region after annealing, doping concentration after annealing, thermal exposure of the layer, and a profile of doping concentration after annealing.

Also, although some embodiments use a lock-in amplifier as a synchronous detector, other implementations of a synchronous detector such as boxcar averager and transient digitizer are used in several other embodiments, as will be apparent to the skilled artisan.

Moreover, instead of a Wollaston prism as discussed above, a Rochon prism can be used in alternative embodiments. An example of the Rochon prism that can be used in embodiments of the type described herein is available from CVI Laser as part# RCHP-10-CA-670-1064, 10 degree separation, 670-1064 nm wavelength.

Therefore, numerous modifications and adaptations of the embodiments described herein are encompassed by the attached claims.

What is claimed is:

1. A method of detecting a signal indicative of a property of a structure in a semiconductor wafer, the method comprising:
    receiving a semiconductor wafer that comprises a test structure, wherein the test structure comprises a first and second region that differ from each other by at least one property and wherein the first region comprises an interface in the wafer;
    illuminating the first region with one of S and P polarized portions of a beam of coherent electromagnetic radiation and illuminating the second region with the other of the S and P polarized portions, wherein the beam has an absorption length less than a thickness of the wafer but greater than a depth of an interface in the wafer and wherein intensity of the S and P polarized portions is modulated over time;
    using a photodetector to measure intensity of a portion of the beam reflected from the wafer; and
    synchronously detecting, at a frequency of modulation of intensity of the S and P polarized portions, an amplitude of an electrical signal generated by the photodetector during measurement by the photodetector.

2. The method of claim 1 further comprising:
    changing at least one process parameter used in fabricating the wafer if said amplitude falls outside a predetermined range.

3. The method of claim 1 wherein the beam is linearly polarized prior to being split, and said modulating comprises:
    rotating the linear polarization of the beam prior to splitting.

4. The method of claim 1 further comprising:
    repeating said acts of (illuminating, using photodetector and synchronously detecting) with electromagnetic radiation of another wavelength.

5. The method of claim 1 wherein the first region comprises a plurality of dopants, and said property is selected from a group consisting of: depth of an interface between the first region and a well in which the first region is formed, abruptness of a profile of the dopants, and a peak in the dopant profile.

6. The method of claim 1 further comprising:
    changing at least one process parameter used in fabricating the wafer if said amplitude falls outside a predetermined range.

7. The method of claim 1 wherein the interface is positioned between a first layer that forms a portion of the front surface and a second layer of semiconductor material located underneath the first layer, wherein the first layer is formed of a dielectric material or of a conductive material.

8. The method of claim 7 further comprises performing a look-up of a table of predetermined data with said amplitude as input to determine thickness of the first layer.

9. The method of claim 1 wherein only one of the first region and second region is a doped region and the method further comprises performing a look-up of a table of predetermined data with said amplitude as input to determine a property of the doped region.

10. The method of claim 9 where said property is selected from the group consisting of:
    depth of an annealed semiconductor junction;
    a dose of implants in said doped region before annealing;
    a dose of implants in said doped region after annealing;
    a doping concentration after annealing;
    abruptness of a profile of doping concentration after annealing; and
    a defect density inside the doped region after annealing.

11. The method of claim 1 wherein:
    said synchronously detecting is performed in a lock-in amplifier coupled to said photodetector to receive therefrom said electrical signal, said lock-in amplifier being tuned to the predetermined frequency f; and
    said lock-in amplifier detecting said amplitude of fluctuation of said electrical signal.

12. The method of claim 1 wherein:
    the absorption length of the beam in the wafer is less than one-half of the thickness of the wafer.

13. The method of claim 1 wherein:
    said first region and said second region touch each other at a common boundary.

14. The method of claim 1 wherein:
    said first region and said second region are separated from each other.

15. The method of claim 1 wherein:
    said coherent electromagnetic radiation is substantially of a predetermined wavelength.

16. The method of claim 1 wherein:
    said spot is formed on a first surface at which a doped region is located in said wafer.

17. The method of claim 1 wherein:
    said spot is formed continuously in time on said wafer.

18. The method of claim 1 wherein:
    said wafer comprises at least a portion of an integrated circuit, said integrated circuit being in addition to said test structure also comprised in said wafer.

19. The method of claim 18 further comprising:
    forming said portion of integrated circuit and said test structure using at least one common process step.

20. A method of detecting a signal indicative of a property of a structure in a semiconductor wafer, the method comprising:
    receiving a semiconductor wafer that comprises a test structure, wherein the test structure comprises a first and second region that differ from each other by at least one property and wherein the first region comprises an interface in the wafer;
    illuminating the first region with one of S and P polarized portions of each of a first beam and a second beam of coherent electromagnetic radiation and illuminating the second region with the other of the S and P polarized portions, wherein each of the first beam and second beam has an absorption length less than a thickness of the wafer but greater than a depth of an interface in the wafer and wherein intensity of the S and P polarized portions of the first beam is modulated over time, wherein spots of the two S polarized portions overlap and spots of the two P polarized portions also overlap, and wherein the first beam has photon energy lower than a semiconductor bandgap energy and the second beam has photon energy greater than the semiconductor bandgap energy;

using a photodetector to measure intensity of a portion of the first beam reflected from the wafer; and synchronously detecting, at a frequency of modulation of intensity of the S and P polarized portions of the first beam, an amplitude of an electrical signal generated by the photodetector during measurement by the photodetector.

21. The method of claim 20 further comprising:

changing at least one process parameter used in fabricating the wafer if said amplitude falls outside a predetermined range.

22. The method of claim 20 wherein the first beam is linearly polarized prior to being split, and said modulating comprises:

rotating the linear polarization of the first beam prior to splitting.

23. A method of detecting a signal indicative of a property of a structure in a semiconductor wafer, the method comprising:

receiving a semiconductor wafer that comprises a test structure, wherein the test structure comprises a first and second region that differ from each other by at least one property and wherein the first region comprises an interface in the wafer;

illuminating the first region with one of S and P polarized portions of a first beam of coherent electromagnetic radiation and illuminating the second region with the other of the S and P polarized portions, wherein the first beam has an absorption length less than a thickness of the wafer but greater than a depth of an interface in the wafer, and wherein the first beam has photon energy lower than a semiconductor bandgap energy;

illuminating the first region with a second beam of coherent electromagnetic radiation having photon energy greater than the semiconductor bandgap energy, wherein intensity of the second beam is modulated over time and wherein a spot of the second beam overlaps at least one of two spots formed by the S polarized portion and the P polarized portion of the first beam;

using two photodetectors to measure a sum and a difference of intensities of the S and P polarized portions of the first beam reflected from the wafer; and synchronously detecting, at a frequency of modulation of intensity of the second beam and in phase thereof, an amplitude of a difference in signals detected by each of the two photodetectors.

24. The method of claim 23 wherein the predetermined frequency f is sufficiently small to avoid creation of a wave of charge carriers in a region of the wafer illuminated by the second beam.

25. An apparatus for evaluating a semiconductor wafer, the apparatus comprising a patterning tool, an ion implanter located adjacent to the patterning tool, and a measurement tool adjacent to the ion implanter, the measurement tool comprising:

a source of a beam of linearly polarized coherent electromagnetic radiation of absorption length less than a thickness of the wafer but greater than a depth of an interface in the wafer;

a polarizing beam splitter having a predetermined angle of separation between the S and P polarized portions of the beam, the polarizing beam splitter being located in a path of the beam from the source, the predetermined angle of separation being less than 20°;

an objective lens located between the polarizing beam splitter and the wafer, the objective lens having a focal length sufficient for the S portion and the P portion to respectively illuminate a first region and a second region on a front surface of the wafer;

means for rotating the linear polarization of the beam, the means for rotating being located in a path of the beam, between the polarizing beam splitter and the source; and a photodetector located in a path of reflection of the beam from the front surface of the wafer, the photodetector being sensitive to reflected radiation from the wafer.

26. The apparatus of claim 25 wherein:

the means for rotating comprises a half-wave plate and a motor rotatably connected to the half-wave plate.

27. The apparatus of claim 25 wherein:

the polarizing beam splitter comprises a Wollaston prism.

28. The apparatus of claim 25 wherein:

the polarizing beam splitter comprises a Rochon prism.

29. The apparatus of claim 25 further comprising:

a synchronous detector coupled to the photodetector to receive a first electrical signal generated by the photodetector, the synchronous detector being further coupled to the means for rotating by a cable carrying a predetermined frequency of said rotation, the synchronous detector measuring an amplitude of a portion of an electrical signal in the photodetector that fluctuates at the predetermined frequency and in phase with polarization rotation by said means.

30. The apparatus of claim 25 further comprising:

another laser mounted opposite to said mirror along a first line that is perpendicular to a second line passing through said source and said mirror.

31. An apparatus for evaluating a semiconductor wafer, the apparatus comprising a patterning tool, an ion implanter located adjacent to the patterning tool, and a measurement tool adjacent to the ion implanter, the measurement tool comprising:

a first source of a first beam of linearly or circularly polarized coherent electromagnetic radiation;

a second source of a second beam of linearly polarized coherent electromagnetic radiation with intensity modulated over time;

wherein the first beam and the second beam are both of absorption length less than a thickness of the wafer but greater than a depth of an interface in the wafer;

a first polarizing beam splitter having a predetermined angle of separation between the S and P polarized portions of the first beam, the first polarizing beam splitter being located in a path of each of the first beam and the second beam, the second beam passing through the first polarizing beam splitter without being split;

an objective lens located between the first polarizing beam splitter and the wafer, the objective lens having a focal length sufficient for the S polarized portion and the P polarized portion to respectively illuminate a first region and a second region on a front surface of the wafer;

a second polarizing beam splitter located in a path of reflection of the S and P polarized portions of the first beam from the front surface of the wafer;

a pair of photodetectors oriented relative to the second polarizing beam splitter so that one photodetector receives the sum and another photodetector receives the difference in intensities of the S and P polarized portions reflected from the wafer; and an amplifier coupled to each photodetector to generate a difference signal obtained by subtracting electrical signals generated by the two photodetectors.

32. The apparatus of claim 31 wherein:

the polarizing beam splitter comprises a Wollaston prism.

33. The apparatus of claim 31 wherein:

the polarizing beam splitter comprises a Rochon prism.

34. The apparatus of claim 31 wherein the intensity of the second beam is modulated at a predetermined frequency, the apparatus further comprising:

a synchronous detector coupled to the amplifier to receive the difference signal therefrom, the synchronous detector being further coupled to the second source by a cable carrying said predetermined frequency, the lock-in amplifier measuring an amplitude of a portion of the difference signal fluctuating at said predetermined frequency and in phase with intensity modulation of said second beam.

* * * * *